US011572373B2

(12) United States Patent
Kratz et al.

(10) Patent No.: US 11,572,373 B2
(45) Date of Patent: Feb. 7, 2023

(54) MAYTANSINOID-BASED DRUG DELIVERY SYSTEMS

(71) Applicant: LADRX CORPORATION, Los Angeles, CA (US)

(72) Inventors: Felix Kratz, Ehrenkirchen (DE); Khalid Abu Ajaj, Berlin (DE); Anna Warnecke, Freiburg (DE); Friederike I. Nollmann, Freiburg (DE); Stephan David Koester, Gundelfingen (DE); Javier Garcia Fernandez, Freiburg (DE); Lara Pes, Freiburg (DE); Heidi-Kristin Walter, Freiburg (DE); Johannes Pall Magnusson, Freiburg (DE); Serghei Chercheja, Freiburg (DE); Patricia Perez Galan, Freiburg (DE); Federico Medda, Freiburg (DE); Steffen Josef Daum, Emmendingen (DE)

(73) Assignee: LADRX CORPORATION, Los Angeles, CA (US)

( * ) Notice: Subject to any disclaimer, the term of this patent is extended or adjusted under 35 U.S.C. 154(b) by 0 days.

(21) Appl. No.: 16/768,418

(22) PCT Filed: Nov. 30, 2018

(86) PCT No.: PCT/US2018/063380
§ 371 (c)(1),
(2) Date: May 29, 2020

(87) PCT Pub. No.: WO2019/108975
PCT Pub. Date: Jun. 6, 2019

(65) Prior Publication Data
US 2020/0385403 A1      Dec. 10, 2020

Related U.S. Application Data

(60) Provisional application No. 62/593,184, filed on Nov. 30, 2017.

(51) Int. Cl.
| C07D 498/18 | (2006.01) |
| A61K 31/537 | (2006.01) |
| A61P 29/00 | (2006.01) |
| A61P 31/00 | (2006.01) |
| A61P 35/00 | (2006.01) |
| A61P 37/00 | (2006.01) |
| A61K 47/64 | (2017.01) |

(52) U.S. Cl.
CPC .......... *C07D 498/18* (2013.01); *A61K 47/643* (2017.08)

(58) Field of Classification Search
CPC ........ A61K 31/537; A61P 29/00; A61P 31/00; A61P 35/00; A61P 37/00; C07D 498/18
See application file for complete search history.

(56) References Cited

U.S. PATENT DOCUMENTS

| 4,125,704 A | 11/1978 | Henry |
| 4,699,880 A | 10/1987 | Goldstein |
| 4,816,397 A | 3/1989 | Boss |
| 4,816,567 A | 3/1989 | Cabilly |
| 4,946,778 A | 8/1990 | Ladner |
| 4,966,999 A | 10/1990 | Coughlin |
| 5,225,539 A | 7/1993 | Winter |
| 5,476,786 A | 12/1995 | Huston |
| 5,514,548 A | 5/1996 | Krebber |
| 6,884,869 B2 | 4/2005 | Senter |
| 7,387,771 B1 | 6/2008 | Kratz |
| 8,703,724 B2 | 4/2014 | Kratz |
| 2012/0195832 A1 | 8/2012 | Kratz |
| 2014/0221429 A1 | 8/2014 | Al-Resayes |
| 2020/0385421 A1 | 12/2020 | Kratz |

FOREIGN PATENT DOCUMENTS

| EP | 0239400 | 9/1987 |
| EP | 0125023 | 6/1991 |
| EP | 0519596 | 12/1992 |
| EP | 0120694 | 7/1993 |
| EP | 0194276 | 8/1993 |
| EP | 0451216 | 1/1996 |
| EP | 2289558 | 3/2011 |
| RU | 2586885 C2 | 6/2016 |
| WO | WO1986001533 | 3/1986 |
| WO | WO1993006213 | 4/1993 |
| WO | WO2001062726 | 8/2001 |
| WO | WO2002088172 | 11/2002 |
| WO | WO2005055939 | 6/2005 |
| WO | WO2013124068 | 8/2013 |
| WO | WO2014094353 A1 | 6/2014 |
| WO | WO2016205378 | 12/2016 |
| WO | WO2019108974 | 6/2019 |

OTHER PUBLICATIONS

Boothroyd et al., Why Do Some Molecules Form Hydrates or Solvates?, Crystal Growth and Design, vol. 18, pp. 1903-1908 (Year: 2018).*
Berge, et al., "Pharmaceutical Salts", J. Pharm. Sci. 66(1): 1-19 (1977).
Bird, et al., "Single-Chain Antigen-Binding Proteins", Science 242: 423-426 (1988).
Chari, et al., "Antibody-Drug Conjugates: An Emerging Concept in Cancer Therapy", Angewandte Reviews 53: 3796-3827 (2014).
Chen, et al., "Tubulin Inhibitor-Based Antibody-Drug Conjugates for Cancer Therapy," Molecules, 22(8):1281-1309 (2017).
Cross, et al., "Rules for the Nomenclature of Organic Chemistry—Section E: Stereochemistry", Pure and Applied Chemistry 45: 11-30 (1976).

(Continued)

*Primary Examiner* — Brenda L Coleman
(74) *Attorney, Agent, or Firm* — Haley Guiliano LLP; Karen Mangasarian; Mihaela Danca

(57) ABSTRACT

The present subject matter provides for albumin-binding prodrugs, maytansinoid-based compounds, and uses thereof.

29 Claims, 16 Drawing Sheets

(56) References Cited

OTHER PUBLICATIONS

Dao, et al., "Design, synthesis, and initial biological evaluation of a steroidal anti-estrogen-doxorubicin bioconjugate for targeting estrogen receptor-positive breast cancer cells", Bioconjugate Chemistry 23: 785-795 (2012).
Daugherty, et al., "Polymerase chain reaction facilitates the cloning, CDR-grafting, and rapid expression of a murine monoclonal antibody directed against the CD18 component of leukocyte integrins", Nucleic Acids Research 19(9): 2471-2476 (1991).
Kamman, et al., "Rapid insertional mutagenesis of DNA by polymerase chain reaction (PCR)", Nucleic Acids Research 17(13): 5404 (1989).
Kratz, et al., "Preparation, characterization and in vitro efficacy of albumin conjugates of doxorubicin", Biological & Pharmaceutical Bulletin 21(1): 56-61 (1998).
Kratz, et al., "Prodrug strategies in anticancer chemotherapy", ChemMedChem 3(1): 20-53 (2008).
Kratz, et al., "Transferrin conjugates of doxombicin: Synthesis, characterization, cellular uptake, and in vitro efficacy", J. Pharm. Sci. 87(3): 338-346 (1998).
Lau, et al., "Novel doxorubincon-monoclonal anti-carcinoembryonic antigen antibody immunoconjugate activity in vitro", Bioorganic & Medicinal Chemistry 3(10): 1305-1312 (1995).
Lewis, et al., "Immunoglobulin complementarity-determining region grafting by recombinant polymerase chain reaction to generate humanized monoclonal antibodies", Gene 101:297-302 (1991).
Newman, et al., ""Primatization" of Recombinant Antibodies for Immunotherapy of Human Diseases: A Macaque/Human Chimeric Antibody Against Human CD4", Biotechnology 10: 1455-1460 (1992).
Nollmann, et al., "Abstract 1657: Structure-activity relationship studies and biological evaluation of novel maytansinoids, a class of highly selective tubulin inhibitors," Cancer Research, 78(13) (2018) (4 pages).
Nollmann, et al., "Abstract 2661: Novel albumin-binding maytansinoids inducing long-term partial and complete tumor regressions in several human cancer xenograft models in nude mice," Cancer Research, 78(13) (2018) (4pages).
Panowski, et al., "Site-specific antibody drug conjugates for cancer therapy", mAbs 6(1): 34-45 (2014).
Ponta, et al., "Tumor-preferential sustained drug release enhances antitumor activity of block copolymer micelles", J. Drug Targeting 22(7): 619-628 (2014).
Rea, et al., "Site-specifically radioiodinated antibody for targeting tumors", Cancer Research (Suppl.) 50: 857s-861s (1990).
Rodrigues, et al., "Correlation of the acid-sensitivity of polyethylene glycol daunorubicin conjugates with their invitro antiproliferative activity", Bioorganic & Medicinal Chemistry 14(12): 4110-4117 (2006).
Sato, et al., "Reshaping a Human Antibody to Inhibit the Interleukin 6-dependent Tumor Cell Growth", Cancer Research 53: 851-856 (1993).
Temming, et al., "Evaluation of RGD-targeted albumin earners for specific delivery of auristatin E to tumor blood vessels," Bioconjugate Chemistry, 17(6):1385-1394 (2006).
U.S. Appl. No. 15/735,885, filed Dec. 12, 2017, Felix Kratz, Pending.
U.S. Appl. No. 16/768,436, filed May 29, 2020, Felix Kratz, Pending.
Kratz, "Albumin as a drug carrier: Design of prodrugs, drug conjugates and nanoparticles," J. Control. Release, 132:171-183 (2008).
Kratz, U. Beyer, "Serum Proteins as Drug Carriers of Anticancer Agents: A Review," Drug Delivery, 5:281-299 (1998).
Marks et al., "A Phase II Study of the Dolastatin 15 Analogue LU103793 in the Treatment of Advanced Non-Small-Cell Lung Cancer," Am. J. Clin. Oncol., 26:336-337 (2003).
Perez et al., "Phase II trial of dolastatin-10 in patients with advanced breast cancer," Invest. New Drugs, 23:257-261 (2005).
Pyataev, et al. "Targeted Delivery of Antitumor Chemotherapeutics: Advanced Technologies and Development Prospects," Povolzhskiy Onkologicheskiy Vestnik, 2012, No. 2, pp. 60-71. (English Abstract Only).
Von Mehren et al., "Phase II trial of dolastatin-10, a novel anti-tubulin agent, in metastatic soft tissue sarcomas," Sarcoma, 8:107-111 (2004).

* cited by examiner

MAYTANSINOID-BASED DRUG DELIVERY SYSTEMS

This application is a United States National Phase Application filed under 35 U.S.C. § 371 of International Patent Application No. PCT/US2018/063380, filed on Nov. 30, 2018, which claims the benefit of and priority from U.S. Provisional Application 62/593,184, filed Nov. 30, 2017, the disclosures of each of which are incorporated by reference herein in their entireties.

BACKGROUND

Many drugs, particularly cancer therapeutics, have a narrow therapeutic window, wherein their side effects limit their beneficial effects. Systemic administration of such drugs often results in a limited therapeutic effect because the dose required to elicit a more robust effect results in unacceptable side effects to the patient. This is particularly critical in the case of those drugs, which possess a high cytotoxic potential, such as cytostatic agents, virostatic agents or immunosuppressive agents. This is even more critical in the case of certain cytotoxic agents that inhibit tumor cell growth in the picomolar range. These agents are generally too toxic for being used as chemotherapeutics. For example, the tubulin-binding maytansine is highly effective in inhibiting tumor cell growth but had failed in various clinical trials due to an unacceptable toxicity profile.

Numerous research endeavors have looked into delivering a particular drug at a particular site of action. Often, this approach results in a higher concentration of the drug at the site of action than would be achieved by systemic administration, while limiting the side effects.

Drug delivery in oncology is of particular interest owing to the narrow therapeutic window of agents used in such indication. Numerous research efforts have concentrated on conjugating anticancer drugs with a wide spectrum of low- and high-molecular-weight carriers including sugars, growth factors, vitamins, peptides, antibodies, polysaccharides, lectins, serum proteins, and synthetic polymers. In most of these drug delivery systems, the drug is bound to the carrier through a spacer that incorporates a pre-determined breaking point that allows the bound drug to be released at the cellular target site (Kratz et al., ChemMedChem, 3:20-53 (2008)).

Conjugates are known in which cytostatic agents are bound to serum proteins, predominantly to specific carrier molecules such as human serum albumin and human serum transferrin, and then administered. In other instances, conjugates comprising a therapeutically effective substance, a spacer molecule and a protein-binding molecule, bind covalently to circulating serum albumin upon administration, which results in the transport of the therapeutically effective substance to the target site where it is released (U.S. Pat. No. 7,387,771). In yet other instances, antibody drug conjugates (ADC) can transport the drug to the target site for local release (Kratz et al., ChemMedChem, 3:20-53 (2008); Panowski et al., mAbs, 6, 34-45 (2014); Chari et al., Angewandte Chem. Int. Ed., 53, 3796-3827 (2014)).

However, when designing drug delivery systems, the appropriate balance should be struck between preserving the targeting properties of the drug carrier while enabling a controlled release of the drug. The drug delivery system should have sufficient stability in the bloodstream, and yet allow effective release of the drug at the tumor site by enzymatic cleavage, reduction or, in a pH-dependent manner (Kratz et al., ChemMedChem, 3:20-53 (2008)). For highly potent cytotoxic agents from the class of maytansinoids (derived from maytansine), only drug delivery systems wherein the maytansinoid-based active species is released non-specifically or reductively were reported. Among these only those using a monoclonal antibody as the carrier molecule have entered a clinical stage of development and merely one antibody-maytansinoid conjugate, namely T-DM1 (Kadcyla®) has gained market approval against certain subtypes of breast cancer. Therefore, there is still a need for efficient and less complex drug delivery and release systems that release highly potent cytotoxic maytansinoid-based agents in an effective manner.

SUMMARY

The present disclosure provides a compound having the structure of Formula (I):

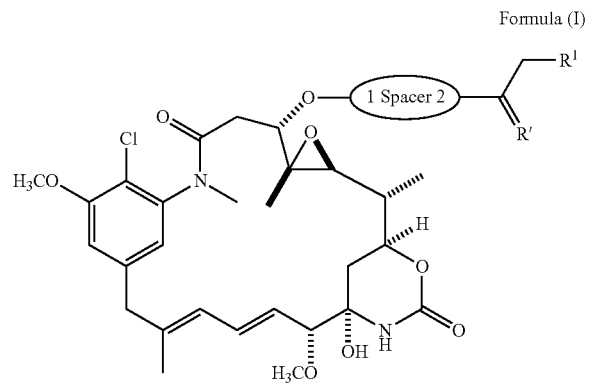

Formula (I)

or a pharmaceutically acceptable salt, hydrate, solvate, or isomer thereof, wherein:
$R^1$ is selected from —H and $C_1$-$C_4$ alkyl;
Spacer is selected from:

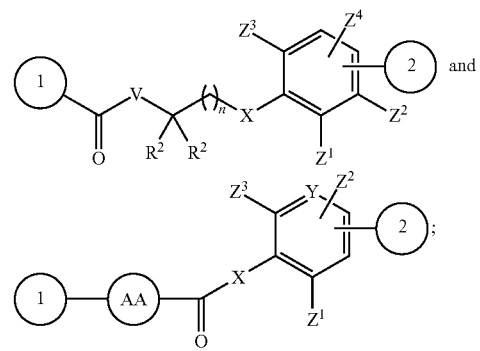

V is absent or selected from —$CH_2$—, —O— and —$NR^3$—, wherein $R^3$ is —H or $C_1$-$C_4$ alkyl;
each $R^2$ is independently selected from —H, halogen (e.g., —F, —Cl, —Br or —I), and $C_1$-$C_4$ alkyl or two $R^2$s taken together form a $C_3$-$C_6$ cycloalkyl;
n is 0-3;
X is absent or selected from —$CH_2$—, —O—, —S—, —Se—, and —$NR^4$—, wherein $R^4$ is —H or $C_1$-$C_4$ alkyl;
Y is selected from =CH— and =N—;
$Z^1$, $Z^2$, $Z^3$ and $Z^4$ are each independently selected from —H, halogen (e.g., —F, —Cl, —Br, or —I), —$CF_3$, —$OCH_3$, —CN, —$NO_2$, $C_1$-$C_4$ alkyl and $C_2$-$C_4$ alkoxy;

AA is an amino acid selected from glycine, D or L proline, sarcosine, N-ethyl-glycine, D or L alanine, D or L N-methyl-alanine, β-alanine, N-methyl-β-alanine, α-aminoisobutyric acid, and N-methyl-α-aminoisobutyric acid;

R' is selected from O and

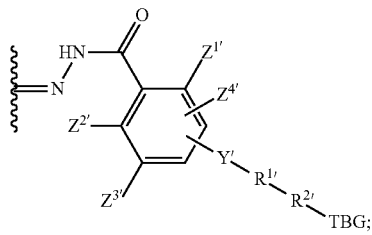

Y' is absent or selected from an optionally substituted $C_1$-$C_6$ alkyl, —NH—C(O)—, and —C(O)—NH—; or Y' is selected from the group consisting of:

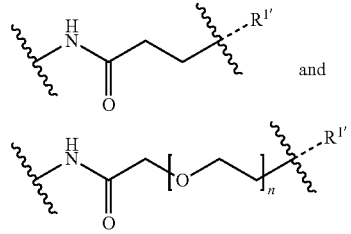

wherein n=0-6;
$R^{1'}$ is absent or selected from the group consisting of:

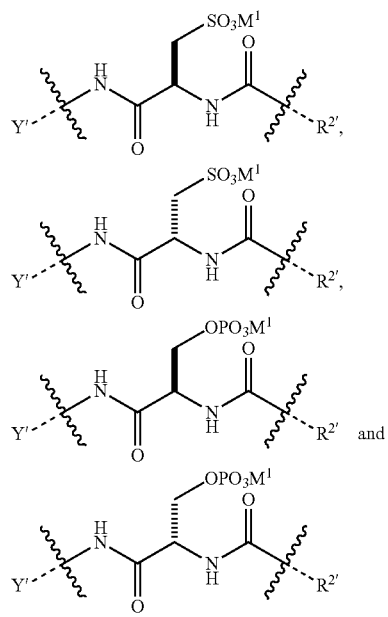

wherein $M^1$ is a pharmaceutically acceptable counter ion (e.g., $H^+$, $Na^+$, $K^+$, $Ca^+$, $NR_4^+$, and $NHR_3^+$; wherein R is H or $C_1$-$C_4$ alkyl);
$R^{2'}$ is optionally substituted $C_1$-$C_{18}$ alkyl wherein optionally up to six carbon atoms in said $C_1$-$C_{18}$ alkyl are each independently replaced with —OCH$_2$CH$_2$—;

$Z^{1'}$, $Z^{2'}$, $Z^{3'}$ and $Z^{4'}$ are each independently selected from —H, halogen (e.g., —F, —Cl, —Br or —I) —CF$_3$, —OCH$_3$, —CN, —NO$_2$, —SO$_3$M$^2$, and $C_1$-$C_4$ alkyl wherein M$^2$ is a pharmaceutically acceptable counter ion (e.g., H$^+$, Na$^+$, K$^+$, Ca$^{2+}$, Mg$^{2+}$, NR$_4^+$, and NHR$_3^+$; wherein R is H or $C_1$-$C_4$ alkyl);

TBG is a thiol-binding group selected from an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, an optionally substituted acetylene group, and an optionally substituted N-hydroxysuccinimide ester group;

wherein said TBG is optionally bound to a thiol-bearing macromolecular carrier or thiol-bearing tumor-specific carrier.

In some embodiments, the disclosure provides a compound having the structure of Formula (I):

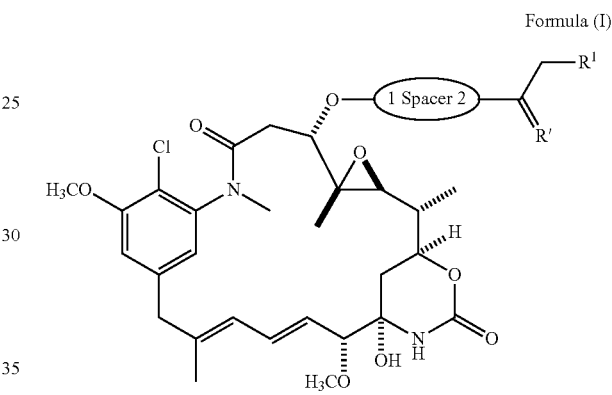

Formula (I)

or a pharmaceutically acceptable salt, hydrate, solvate, or isomer thereof, wherein:
$R^1$ is selected from —H and $C_1$-$C_4$ alkyl;
Spacer is selected from:

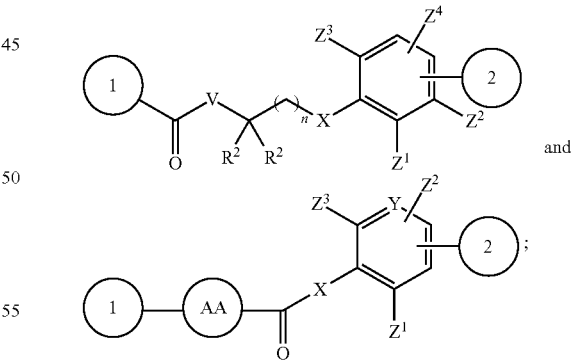

V is absent or selected from —CH$_2$—, —O— and —NR$^3$—, wherein R$^3$ is —H or $C_1$-$C_4$ alkyl;
each R$^2$ is independently selected from —H, halogen (e.g., —F, —Cl, —Br or —I), and $C_1$-$C_4$ alkyl or two R$^2$s taken together form a $C_3$-$C_6$ cycloalkyl;
n is 0-3;
X is absent or selected from —CH$_2$—, —O—, —S—, —Se—, and —NR$^4$—, wherein R$^4$ is —H or $C_1$-$C_4$ alkyl; Y is selected from =CH— and =N—;

$Z^1$, $Z^2$, $Z^3$ and $Z^4$ are each independently selected from —H, halogen (e.g., —F, —Cl, —Br, or —I), —CF$_3$, —OCH$_3$, —CN, —NO$_2$, C$_1$-C$_4$ alkyl and C$_2$-C$_4$ alkoxy;

AA is an amino acid selected from glycine, D or L proline, sarcosine, D or L alanine, D or L N-methylalanine, β-alanine, N-methyl-β-alanine, α-aminoisobutyric acid, and N-methyl-α-aminoisobutyric acid;

R' is selected from O and

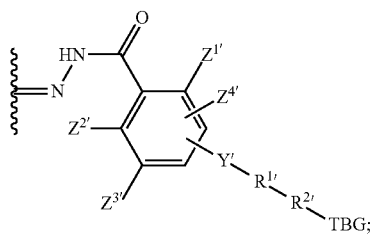

Y' is absent or selected from an optionally substituted C$_1$-C$_6$ alkyl, —NH—C(O)—, and —C(O)—NH—; or Y' is selected from the group consisting of:

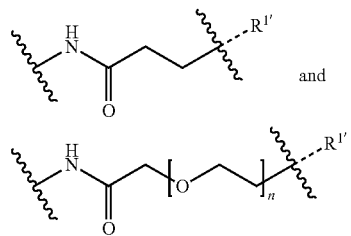

wherein n=0-6;
R$^{1'}$ is absent or selected from the group consisting of:

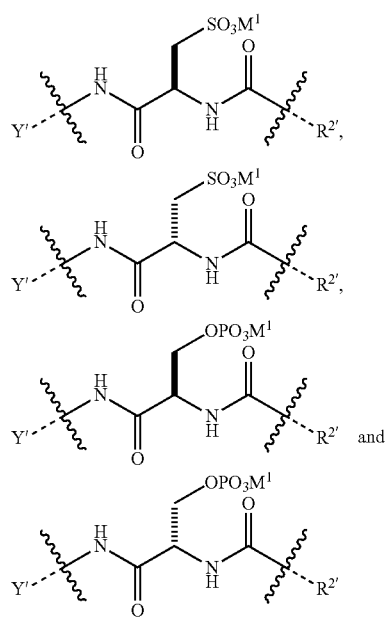

wherein M$^1$ is a pharmaceutically acceptable counter ion (e.g., H$^+$, Na$^+$, K$^+$, Ca$^{2+}$, Mg$^{2+}$, NR$_4^+$, and NHR$_3^+$; wherein R is H or C$_1$-C$_4$ alkyl);

R$^{2'}$ is optionally substituted C$_1$-C$_{18}$ alkyl wherein optionally up to six carbon atoms in said C$_1$-C$_{18}$ alkyl are each independently replaced with —OCH$_2$CH$_2$—;

$Z^{1'}$, $Z^{2'}$, $Z^{3'}$ and $Z^{4'}$ are each independently selected from —H, halogen (e.g., —F, —Cl, —Br or —I) —CF$_3$, —OCH$_3$, —CN, —NO$_2$, —SO$_3$M$^2$, and C$_1$-C$_4$ alkyl wherein M$^2$ is a pharmaceutically acceptable counter ion (e.g., H$^+$, Na$^+$, K$^+$, Ca$^{2+}$, Mg$^{2+}$, NR$_4^+$, and NHR$_3^+$; wherein R is H or C$_1$-C$_4$ alkyl);

TBG is a thiol-binding group selected from an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, an optionally substituted acetylene group, and an optionally substituted N-hydroxysuccinimide ester group;

wherein said TBG is optionally bound to a thiol-bearing macromolecular carrier or thiol-bearing tumor-specific carrier.

In some embodiments, the compound has a structure of Formula (II):

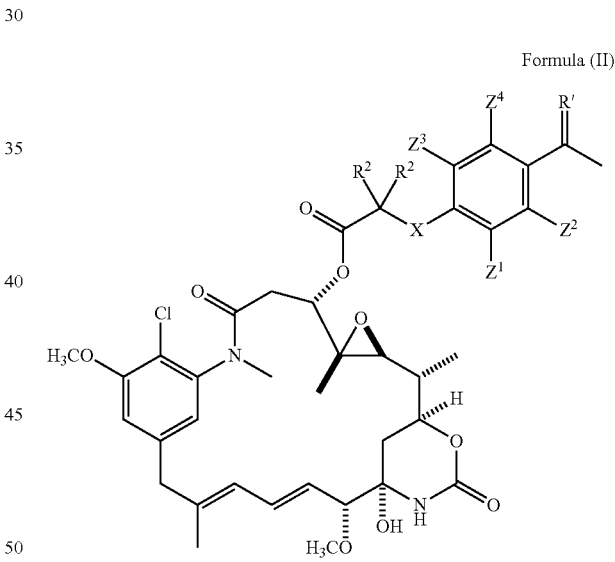

Formula (II)

or a pharmaceutically acceptable salt, hydrate, solvate, or isomer thereof, wherein:

each R$^2$ is independently selected from —H, and C$_1$-C$_4$ alkyl or two R$^2$s taken together form a C$_3$-C$_6$, cycloalkyl;

X is absent or selected from —CH$_2$—, —O—, —S— and —NR$^3$—, wherein R$^3$ is —H or C$_1$-C$_4$ alkyl;

$Z^1$, $Z^2$, $Z^3$ and $Z^4$ are each independently selected from —H, halogen (e.g., —F, —Cl, —Br or —I), —CF$_3$, —OCH$_3$, —NO$_2$ and —CH$_3$.

In some embodiments, the compound has a structure of Formula (III):

Formula (III)

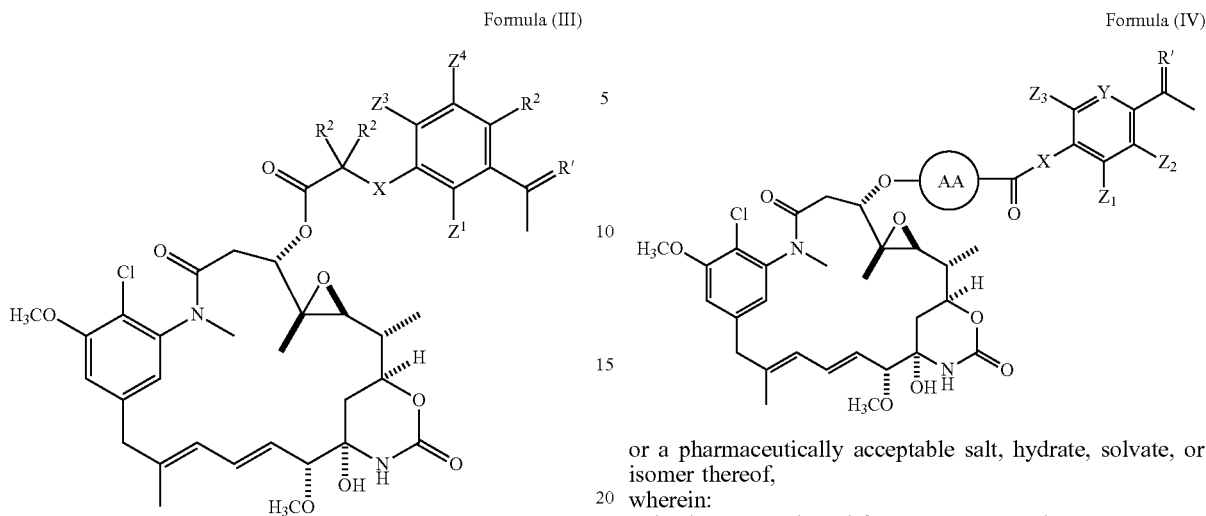

or a pharmaceutically acceptable salt, hydrate, solvate, or isomer thereof,
wherein:
each $R^2$ is independently selected from —H, and $C_1$-$C_4$ alkyl or two $R^2$s are taken together form a $C_3$-$C_6$, cycloalkyl;
X is absent or selected from —$CH_2$—, —O—, —S— and —$NR^3$—, wherein $R^3$ is —H or $C_1$-$C_4$ alkyl;
$Z^1$, $Z^2$, $Z^3$ and $Z^4$ are each independently selected from —H, halogen (e.g., —F, —Cl, —Br or —I), —$CF_3$, —$OCH_3$, —$NO_2$ and —$CH_3$.

In some embodiments, the compound has a structure of Formula (IV):

Formula (IV)

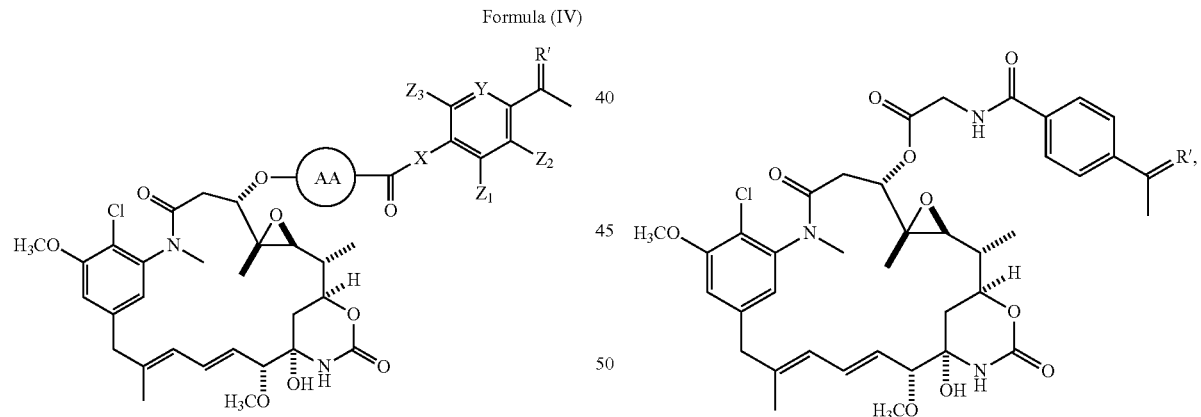

or a pharmaceutically acceptable salt, hydrate, solvate, or isomer thereof,
wherein:
X is absent or selected from —$CH_2$— and —NH—;
Y is =CH— or =N—;
$Z^1$, $Z^2$, $Z^3$ and $Z^3$ are each independently selected from —H, halogen (e.g., —F, —Cl, —Br or —I), —$CF_3$, —$OCH_3$, —$NO_2$ and —$CH_3$;
AA is an amino acid selected from glycine, D or L proline, sarcosine, N-ethyl-glycine, D or L alanine, D or L N-methylalanine, β-alanine, N-methyl-β-alanine, α-aminoisobutyric acid, and N-methyl-α-aminoisobutyric acid.

In some embodiments, the compound has a structure of Formula (IV):

Formula (IV)

or a pharmaceutically acceptable salt, hydrate, solvate, or isomer thereof,
wherein:
X is absent or selected from —$CH_2$— and —NH—;
Y is =CH— or =N—;
$Z^1$, $Z^2$, $Z^3$ and $Z^3$ are each independently selected from —H, halogen (e.g., —F, —Cl, —Br or —I), —$CF_3$, —$OCH_3$, —$NO_2$ and —$CH_3$;
AA is an amino acid selected from glycine, D or L proline, sarcosine, D or L alanine, D or L N-methylalanine, β-alanine, N-methyl-β-alanine, α-aminoisobutyric acid, and N-methyl-α-aminoisobutyric acid.

In some embodiments, $R^1$ is —H. In some embodiments, at least one of $Z^1$, $Z^2$, $Z^3$ and $Z^4$ is not H. In some embodiments, at least one of $Z^1$, $Z^2$, $Z^3$ and $Z^4$ is —F or —$NO_2$. In some embodiments, n is 0 and X is absent. In some embodiments, n is 0 and X is —$CH_2$—. In some embodiments, n is 0 and X is —O—, NHMe, or —S—. In some embodiments, the compound is selected from:

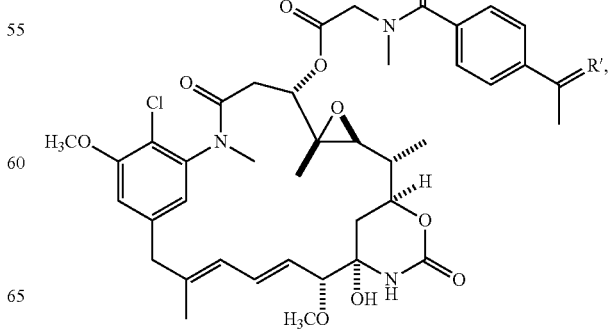

-continued

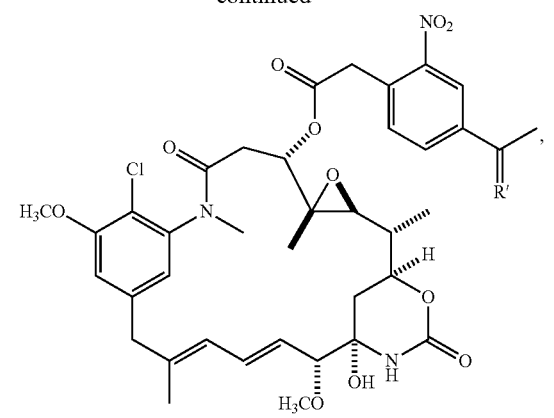
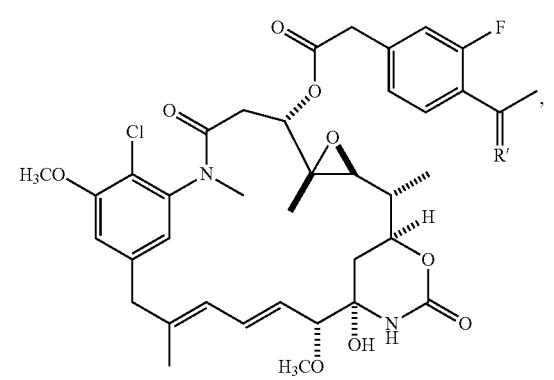
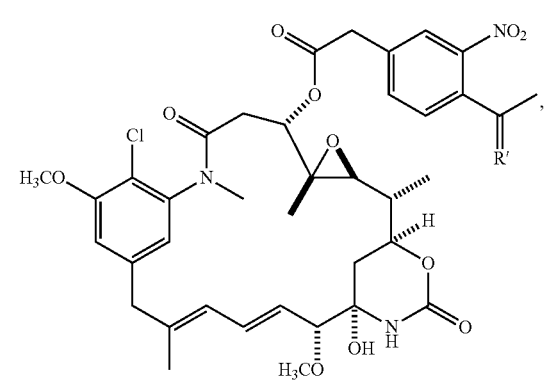
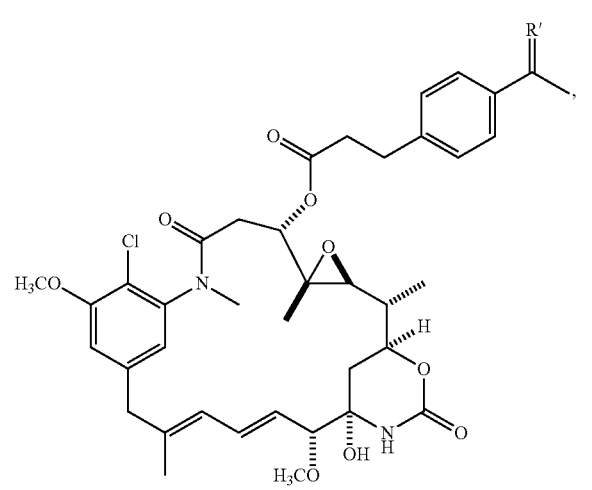
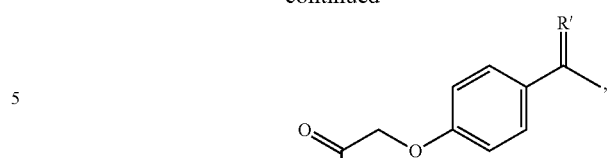
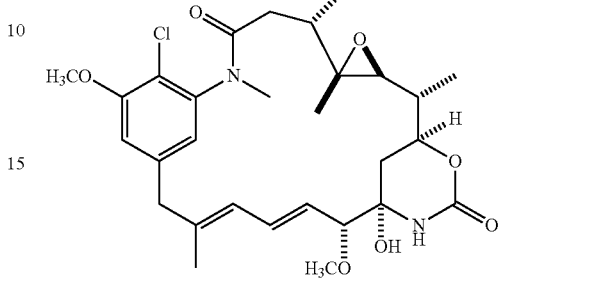
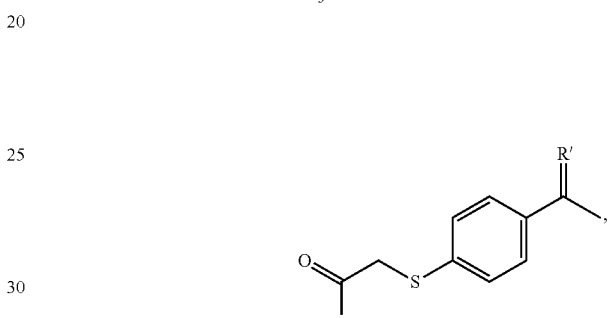
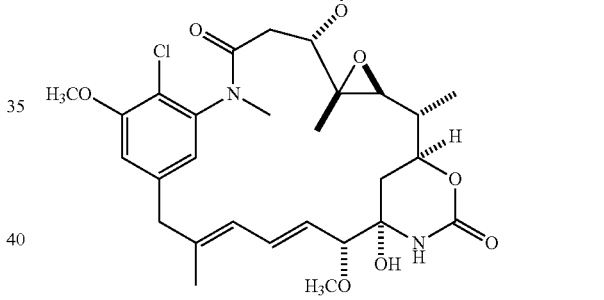
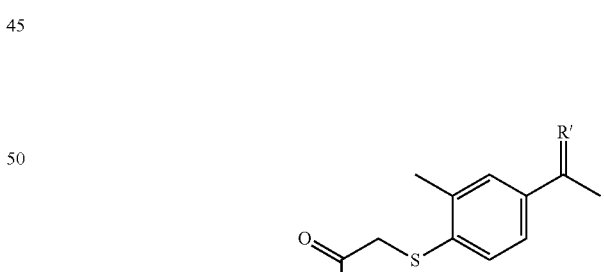
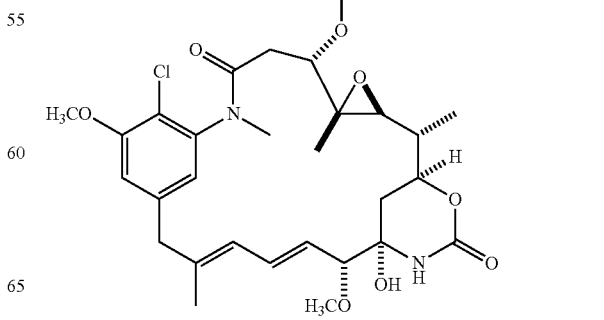

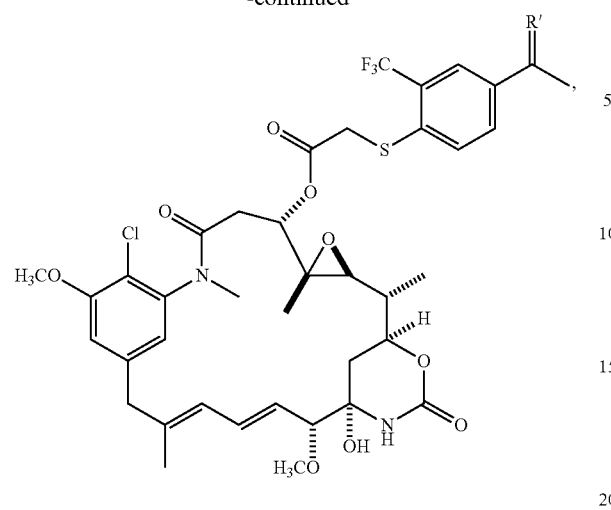
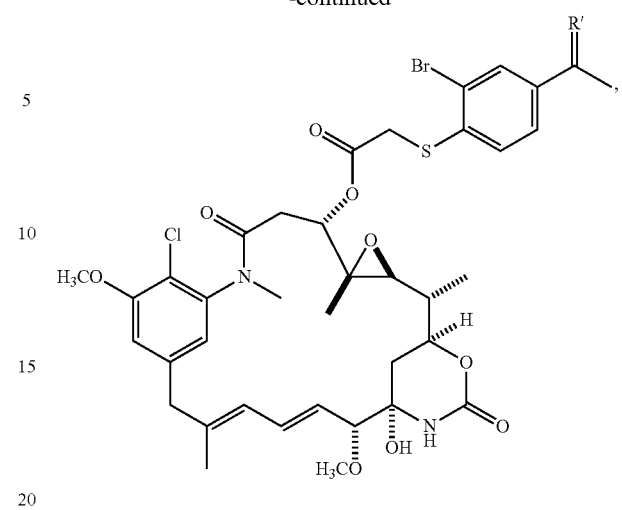
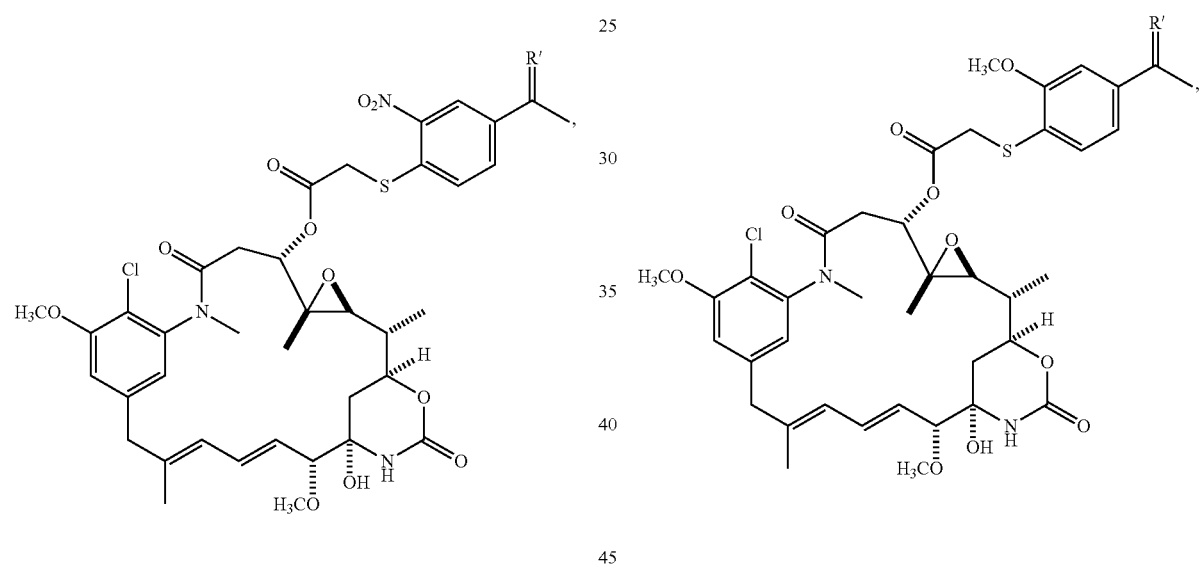
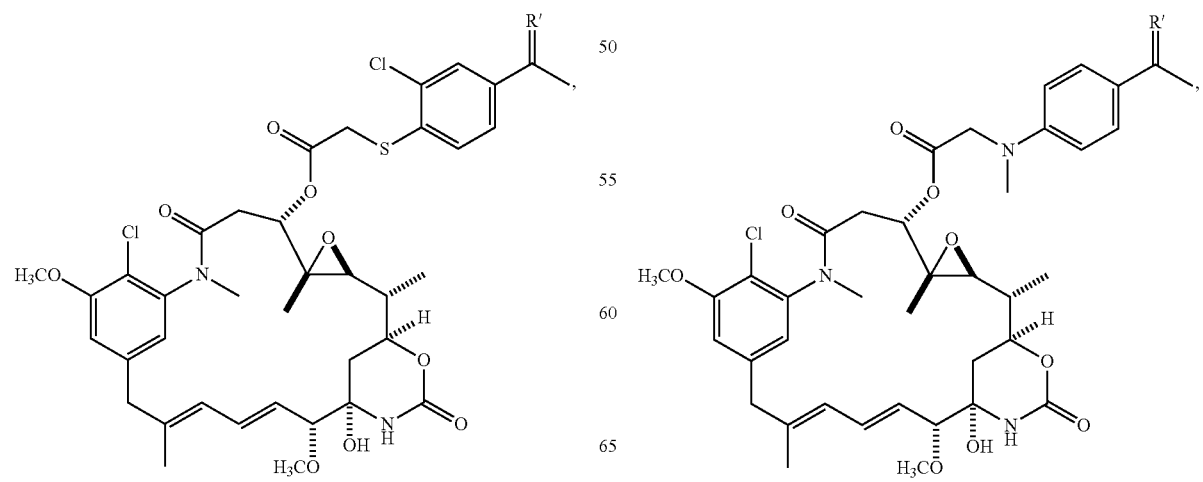

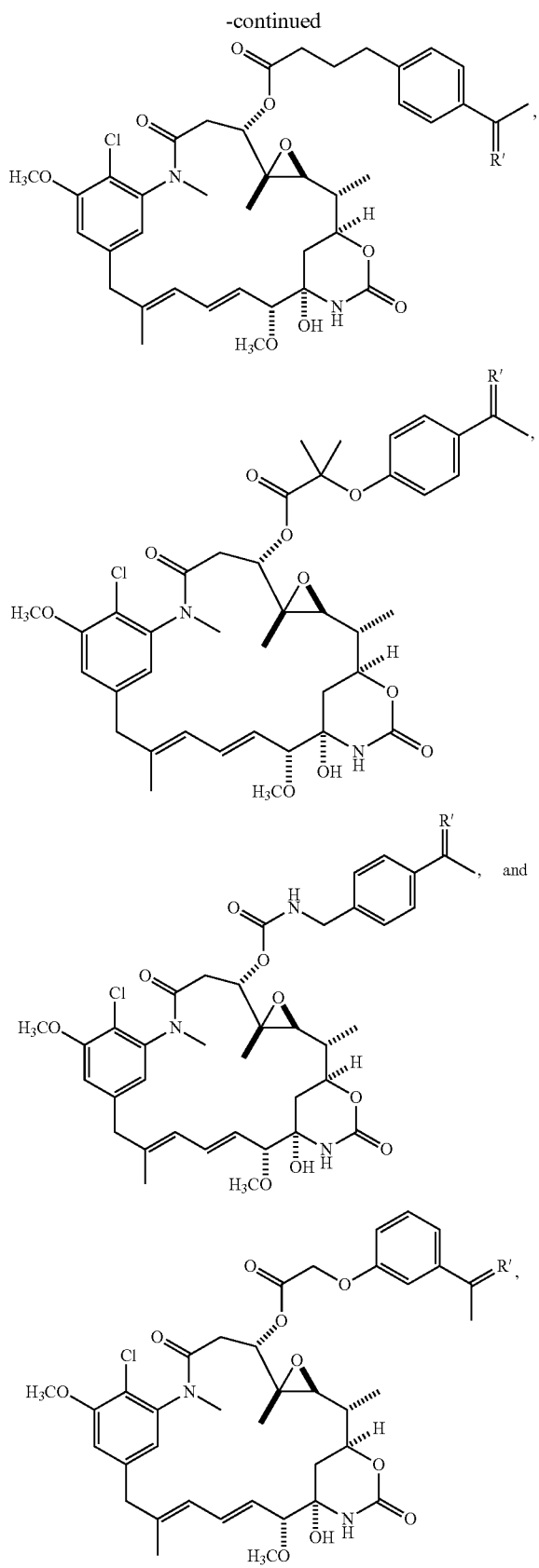

or a pharmaceutically acceptable salt, hydrate, solvate, or isomer thereof.

In some embodiments, the pharmaceutically acceptable counter ion is selected from $H^+$, $Na^+$, $K^+$, $Ca^{2+}$, $Mg^{2+}$, $NR_4^+$, and $NHR_3^+$; wherein R is H or $C_1$-$C_4$ alkyl.

In some embodiments, R' is O. In some embodiments, R' is:

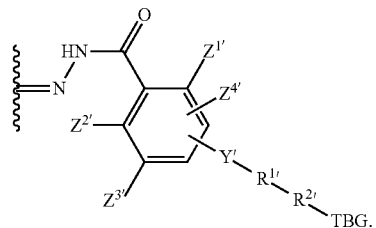

In some embodiments, the compound is not bound to a thiol-bearing macromolecular carrier or thiol-bearing tumor-specific carrier. In some embodiments, the compound is bound to a thiol-bearing macromolecular carrier or thiol-bearing tumor-specific carrier. In some embodiments, the thiol-bearing macromolecular carrier or thiol-bearing tumor-specific carrier is selected from endogenous albumin, exogenous albumin, an antibody, an antibody fragment, a peptide, a natural or synthetic polymer, a liposome and a nanoparticle. In some embodiments, TBG is an optionally substituted maleimide group. In some embodiments, Z" is selected from $-NO_2$ or $-SO_3M^2$;
and Y' is selected from $-NHC(O)-$ or

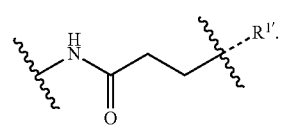

In some embodiments, $R^{1'}$ is

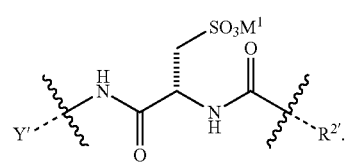

In some embodiments, R' is:

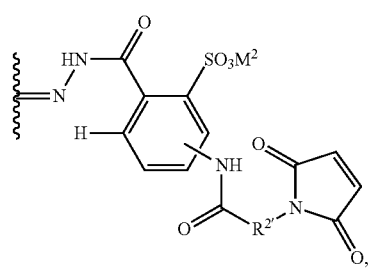

or a pharmaceutically acceptable salt, hydrate, solvate, or isomer thereof,
wherein $R^{2'}$ is selected from optionally substituted $C_1$-$C_{18}$ alkyl wherein optionally up to six carbon atoms in said $C_1$-$C_{18}$ alkyl are each independently replaced with $-OCH_2CH_2-$.

In some embodiments, R' is:
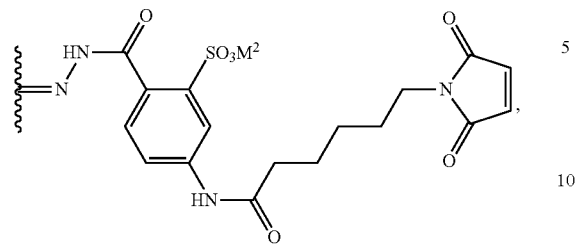
or a pharmaceutically acceptable salt, hydrate, solvate, or isomer thereof.
In some embodiments, the compound is selected from:
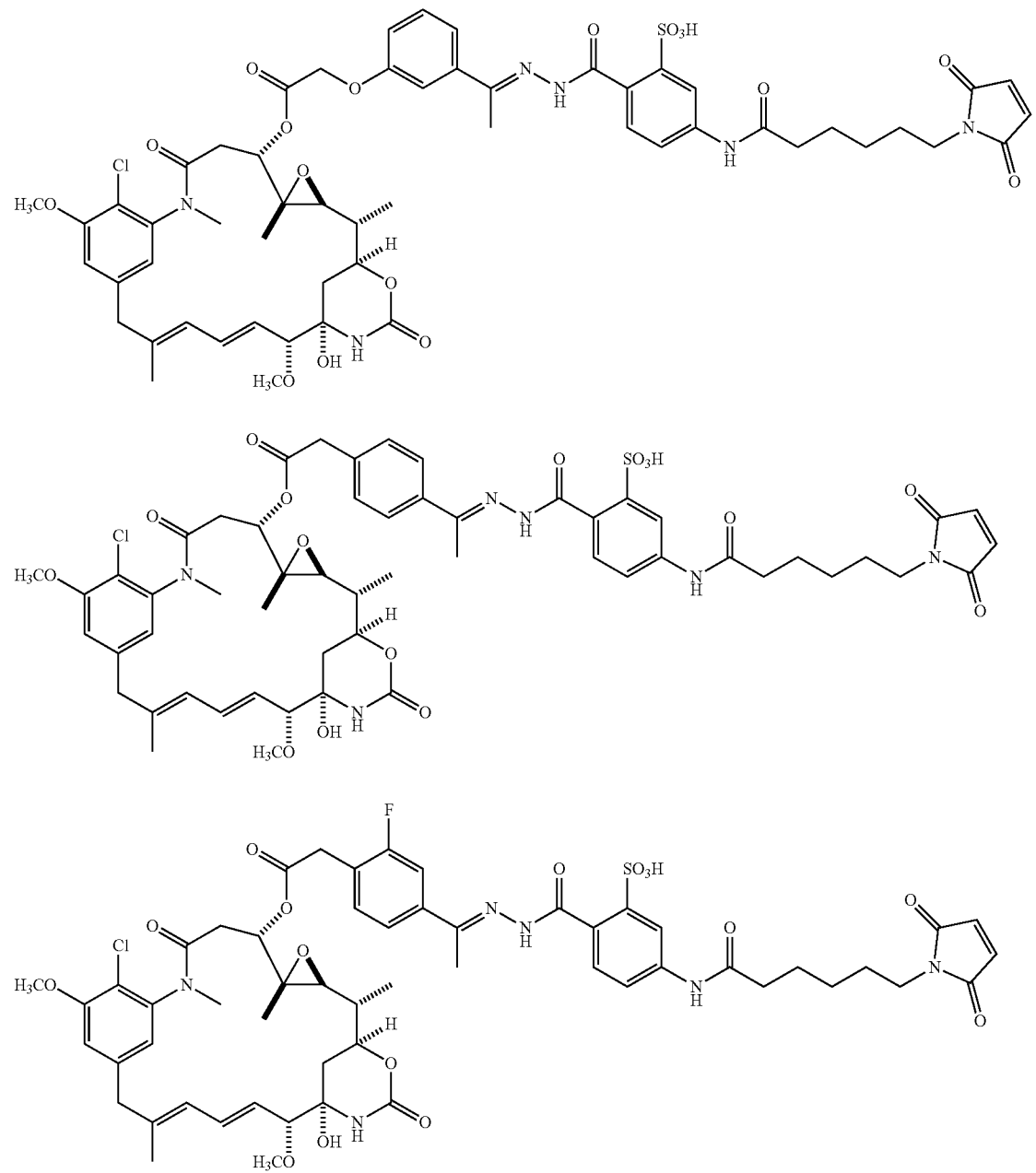

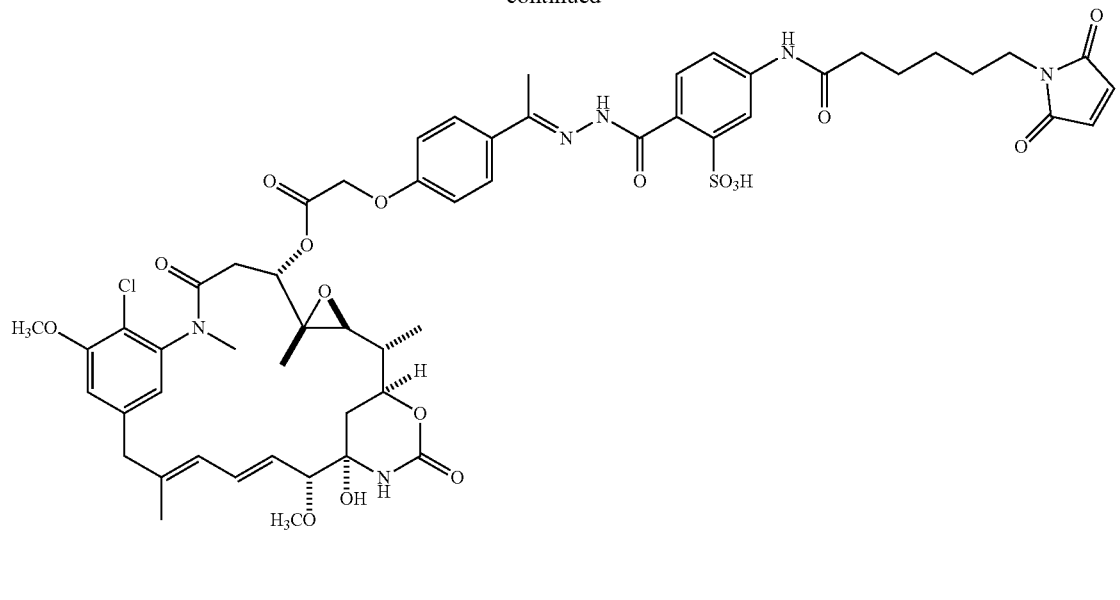
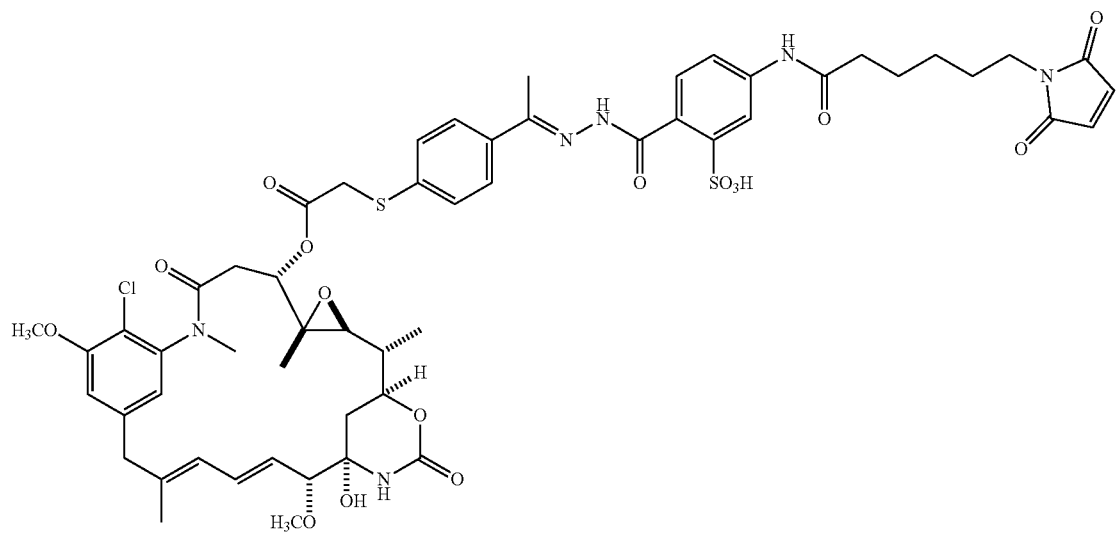
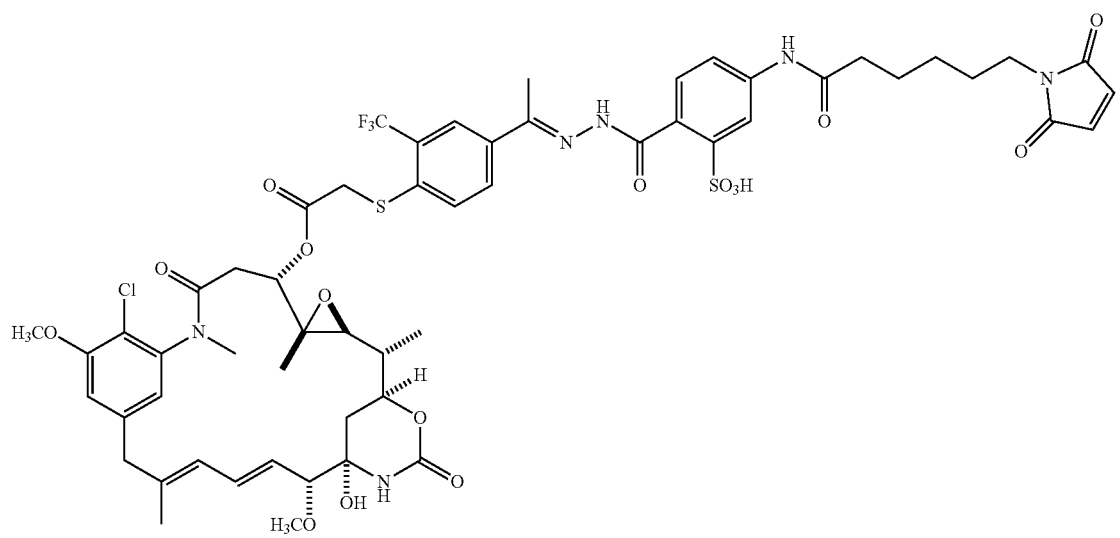

21
-continued
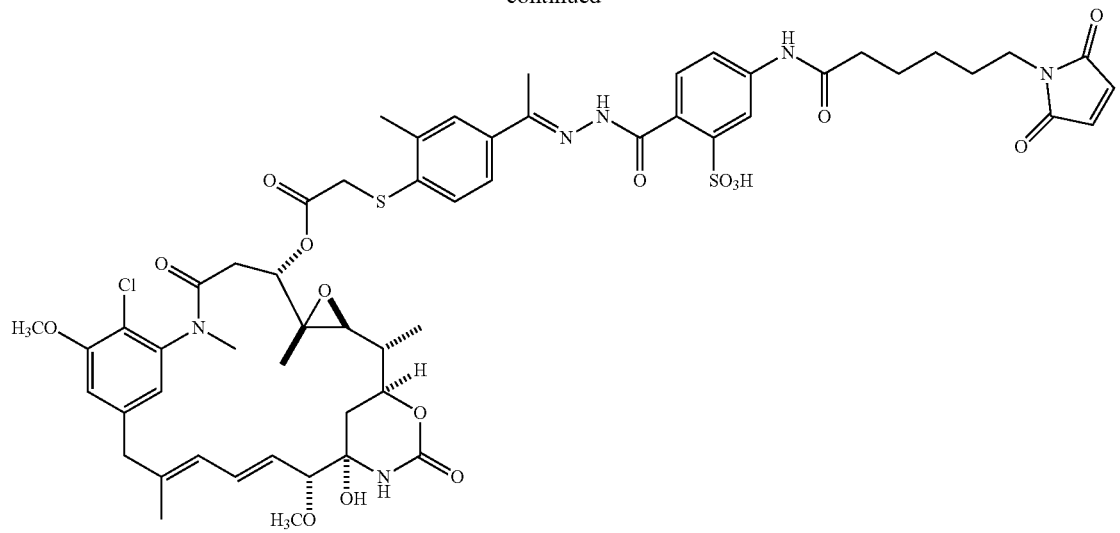
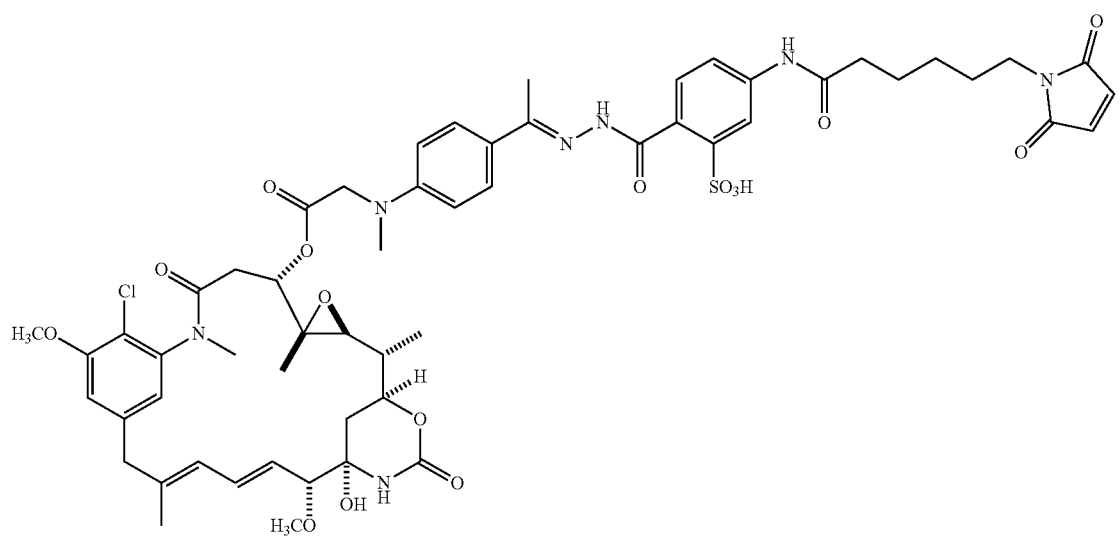
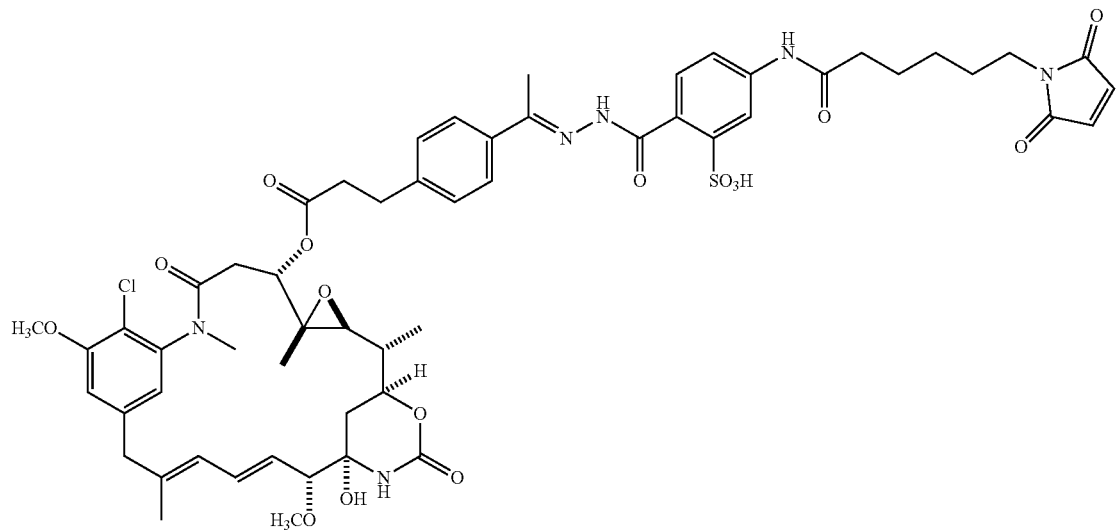
22 or a pharmaceutically acceptable salt, hydrate, solvate, or isomer thereof.

In some embodiments, R' is:

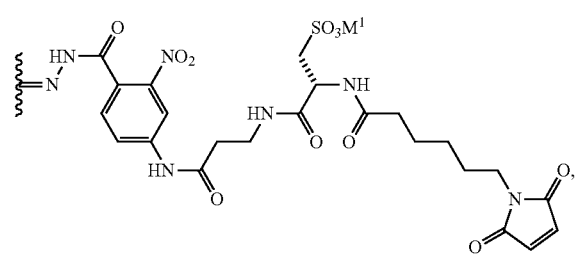

or a pharmaceutically acceptable salt, hydrate, solvate, or isomer thereof wherein $M^1$ is a pharmaceutically acceptable counter ion.

In some embodiments, the compound is selected from:

In some embodiments, the compound of any of claims 14-20, wherein R' is:

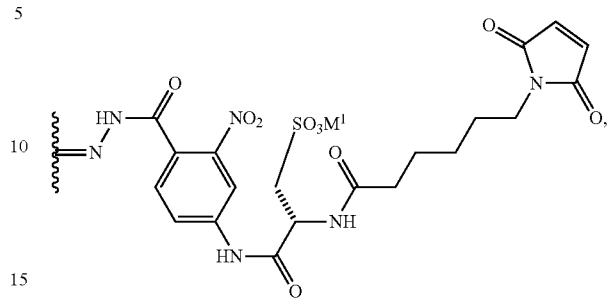

or a pharmaceutically acceptable salt, hydrate, solvate, or isomer thereof;

wherein $M^1$ is a pharmaceutically acceptable counter ion.

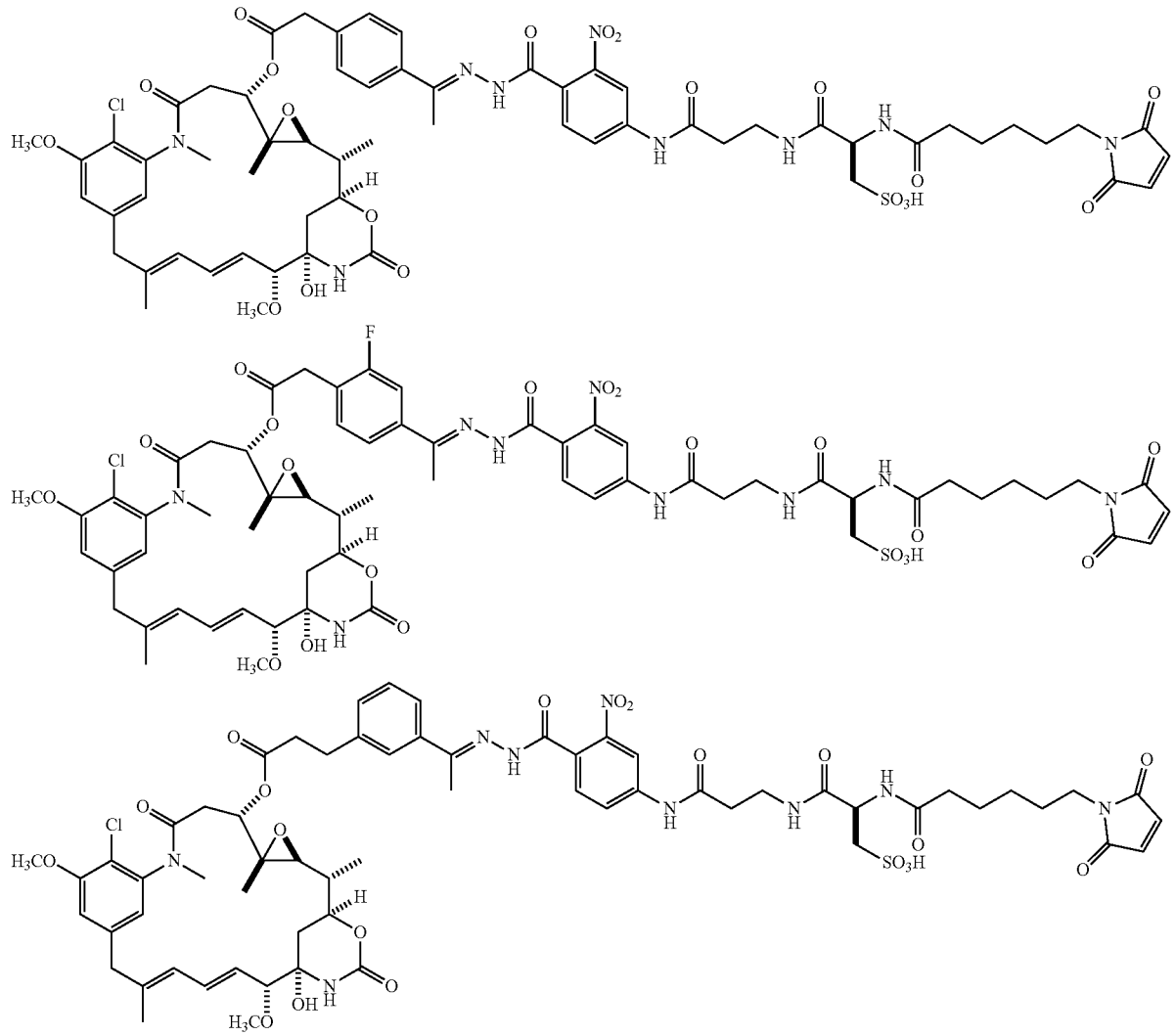

or a pharmaceutically acceptable salt, hydrate, solvate, or isomer thereof.

In some embodiments, the compound of claim 26, wherein the compound is:

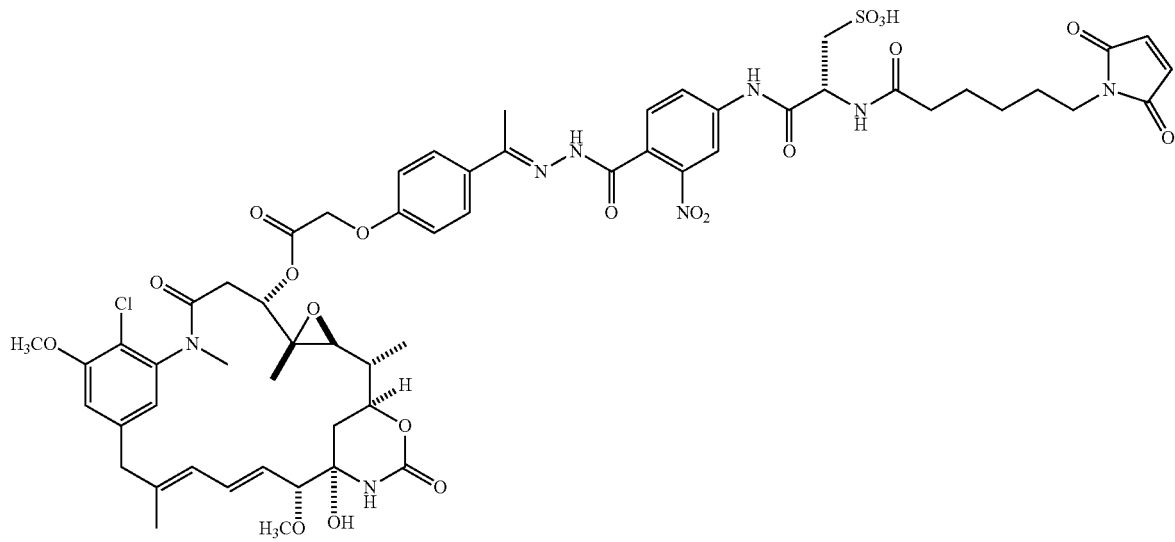

Other embodiments include a pharmaceutical composition comprising a compound as disclosed herein, and a pharmaceutically acceptable carrier.

Other embodiments include a method for treating a disease or condition selected from a cancer, a virus disease, autoimmune disease, acute or chronic inflammatory disease, and a disease caused by bacteria, fungi, or other micro-organisms, comprising administering to a patient in need thereof a therapeutically effective amount of a compound or a pharmaceutical composition as disclosed herein. In some embodiments, the disease is cancer, e.g., a cancer is selected from adenocarcinoma, uveal melanoma, acute leukemia, acoustic neuroma, ampullary carcinoma, anal carcinoma, astrocytoma, basalioma, pancreatic cancer, connective tissue tumor, bladder cancer, bronchial carcinoma, non-small cell bronchial carcinoma, breast cancer, Burkitt's lymphoma, corpus carcinoma, CUP syndrome, colon cancer, cancer of the small intestine, ovarian cancer, endometrial carcinoma, gallbladder cancer, gallbladder carcinoma, uterine cancer, cervical cancer, neck, nose and ear tumors, hematological neoplasia, hairy cell leukemia, urethral cancer, skin cancer, gliomas, testicular cancer, Kaposi's sarcoma, laryngeal cancer, bone cancer, colorectal carcinoma, head/neck tumors, colon carcinoma, craniopharyngeoma, liver cancer, leukemia, lung cancer, non-small cell lung cancer, Hodgkin's lymphoma, non-Hodgkin's lymphoma, stomach cancer, colon cancer, medulloblastoma, melanoma, meningioma, kidney cancer, renal cell carcinomas, oligodendroglioma, esophageal carcinoma, osteolytic carcinomas and osteoplastic carcinomas, osteosarcoma, ovarian carcinoma, pancreatic carcinoma, penile cancer, prostate cancer, tongue cancer, ovary carcinoma, and lymph gland cancer.

Other embodiments include a method of reducing cytotoxicity of a compound comprising administering a compound or a pharmaceutical composition as disclosed herein to a patient in need thereof, wherein the administration results in a reduction in cytotoxicity when compared to an equivalent dose of the unmodified active agent.

Other embodiments include a method of increasing the concentration of a metabolite of a compound in a tumor, comprising administering the compound or a pharmaceutical composition as disclosed herein to a patient in need thereof, wherein the increase is compared to an equivalent dose of the unmodified active agent.

Other embodiments include a compound as disclosed herein for use as a medicament.

Other embodiments include a compound as disclosed herein for use in treating a disease or condition selected from the group consisting of a cancer, a virus disease, autoimmune disease, acute or chronic inflammatory disease, and a disease caused by bacteria, fungi, or other micro-organisms.

Other embodiments include a use of a compound or a composition as disclosed herein in the preparation of a medicament for the treatment of a disease or condition selected from a cancer, a virus disease, autoimmune disease, acute or chronic inflammatory disease, and a disease caused by bacteria, fungi, or other micro-organisms.

DETAILED DESCRIPTION

Figure 1:
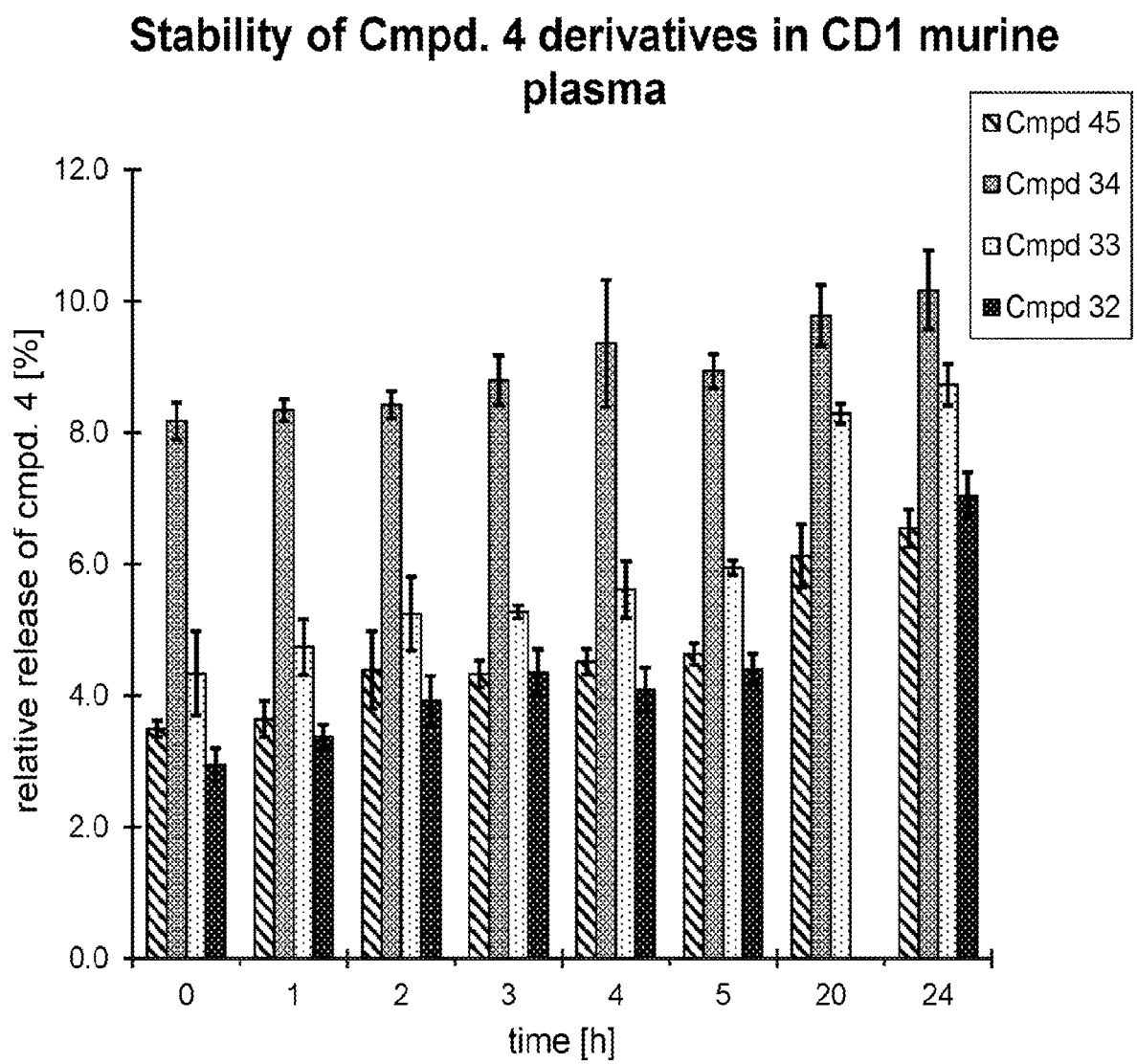
FIG. 1 shows the stability of different linkers with 4 in CD1 murine plasma.

Unless otherwise defined herein, scientific and technical terms used in this application shall have the meanings that are commonly understood by those of ordinary skill in the art. Generally, nomenclature relating to techniques of chemistry, molecular biology, cell and cancer biology, immunology, microbiology, pharmacology, and protein chemistry, described herein, are those well-known and commonly used in the art.

All publications, patents and published patent applications referred to in this application are specifically incorporated by reference herein. In case of conflict, the present specification, including its specific definitions, will control. Unless otherwise specified, it is to be understood that each embodiment disclosed herein may be used alone or in combination with any one or more other embodiments of the invention.

Definitions

Throughout this specification, the word "comprise" or variations such as "comprises" or "comprising" will be understood to imply the inclusion of a stated integer (or components) or group of integers (or components), but not the exclusion of any other integer (or components) or group of integers (or components).

Throughout the application, where a compound or composition is described as having, including, or comprising, specific components, it is contemplated that such compound or composition also may consist essentially of, or consist of, the recited components. Similarly, where methods or processes are described as having, including, or comprising specific process steps, the processes also may consist essentially of, or consist of, the recited processing steps. Further, it should be understood that the order of steps or order for performing certain actions is immaterial so long as the compounds, compositions and methods described herein remains operable. Moreover, two or more steps or actions can be conducted simultaneously.

The singular forms "a," "an," and "the" include the plurals unless the context clearly dictates otherwise.

The term "including" is used to mean "including but not limited to." "Including" and "including but not limited to" are used interchangeably.

The term "or" as used herein should be understood to mean "and/or", unless the context clearly indicates otherwise.

The terms "drug," "agent," "therapeutic agent", "therapeutically active agent", "cytotoxic agent or drug", "highly cytotoxic agent or drug", or "therapeutically effective substance" are used to mean any compound which brings about a pharmacological effect either by itself or after its conversion in the organism in question, and thus also includes the derivatives from these conversions. The pharmacological effect of the drugs of the composition according to the present disclosure can be a single effect only, e.g. a cytostatic and/or cytotoxic effect, or a broad pharmacological spectrum of actions, such as an immunosuppressive and antiphlogistic effect at the same time.

The terms "patient," "subject," or "individual" are used interchangeably and refer to either a human or a non-human animal. These terms include mammals such as humans, primates, livestock animals (e.g., bovines, porcines), companion animals (e.g., canines, felines) and rodents (e.g., mice and rats). In certain embodiments, the patient or subject is a human patient or subject, such as a human patient having a condition in need of treatment.

The term "pharmaceutical composition" refers to a composition suitable for pharmaceutical use in a subject animal, including humans and mammals, e.g., combined with one or more pharmaceutically acceptable carriers, excipients or solvents. Such a composition may also contain diluents, fillers, salts, buffers, stabilizers, solubilizers, protectants and other materials well known in the art. In certain embodiments, a pharmaceutical composition encompasses a composition comprising the active ingredient(s), and the inert ingredient(s) that make up the excipient, carrier or diluent, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and one or more pharmaceutically acceptable excipient(s), carrier(s) and/or diluent(s).

The term "pharmaceutically acceptable carrier" refers to a non-toxic carrier that may be administered to a patient, together with a therapeutically effective substance disclosed herein, and which does not destroy the pharmacological activity of the agent. The term "excipient" refers to an additive in a formulation or composition that is not a pharmaceutically active ingredient. In certain embodiments, a "pharmaceutically acceptable" substance is suitable for use in contact with cells, tissues or organs of animals or humans without excessive toxicity, irritation, allergic response, immunogenicity or other adverse reactions, in the amount used in the dosage form according to the dosing schedule, and commensurate with a reasonable benefit/risk ratio. In certain embodiments, a "pharmaceutically acceptable" substance that is a component of a pharmaceutical composition is, in addition, compatible with the other ingredient(s) of the composition. In certain embodiments, the terms "pharmaceutically acceptable excipient", "pharmaceutically acceptable carrier" and "pharmaceutically acceptable diluent" encompass, without limitation, pharmaceutically acceptable inactive ingredients, materials, compositions and vehicles, such as liquid fillers, solid fillers, diluents, excipients, carriers, solvents and encapsulating materials. Carriers, diluents and excipients also include all pharmaceutically acceptable dispersion media, coatings, buffers, isotonic agents, stabilizers, absorption delaying agents, antimicrobial agents, antibacterial agents, antifungal agents, adjuvants, etc. Except insofar as any conventional excipient, carrier or diluent is incompatible with the active ingredient; the present disclosure encompasses the use of conventional excipients, carriers and diluents in pharmaceutical compositions. See, e.g., Remington: The Science and Practice of Pharmacy, 21st Ed., Lippincott Williams & Wilkins (Philadelphia, Pa., 2005); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press LLC (Boca Raton, Fla., 2004).

The terms "pharmaceutically effective amount," "therapeutically effective amount," or "therapeutically effective dose" refer to an amount effective to treat a disease or condition in a patient, e.g., effecting a beneficial and/or desirable alteration in the general health of a patient suffering from a disease (e.g., cancer) or condition, treatment, healing, inhibition or amelioration of a physiological response or condition, etc. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of disease, the therapeutics or combination of therapeutics selected for administration, and the mode of administration. The skilled worker can readily determine the effective amount for a given situation by routine experimentation. The skilled worker will recognize that treating cancer includes, but is not limited to, killing cancer cells, preventing the growth of new cancer cells, causing tumor regression (a decrease in tumor size), causing a decrease in metastasis, improving vital functions of a patient, improving the well-being of the patient, decreasing pain, improving appetite, improving the patient's weight, and any combination thereof. The terms "pharmaceutically effective amount," "therapeutically effective amount," or "therapeutically effective dose" also refer to the amount required to improve the clinical symptoms of a patient. The therapeutic methods or methods of treating cancer described herein are not to be interpreted or otherwise limited to "curing" cancer.

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation, amelioration, or slowing the progression, of one or more symptoms or conditions associated with a condition, e.g., cancer, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Exemplary beneficial clinical results are described herein.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. When a method is part of a therapeutic regimen involving more than one agent or treatment modality, the disclosure contemplates that the agents may be administered at the same or differing times and via the same or differing routes of administration. Appropriate methods of administering a substance, a compound or an agent to a subject will also depend, for example, on the age of the subject, whether the subject is active or inactive at the time of administering, whether the subject is cognitively impaired at the time of administering, the extent of the impairment, and the chemical and biological properties of the compound or agent (e.g. solubility, digestibility, bioavailability, stability and toxicity).

The term "substituted" refers to moieties having substituents replacing hydrogen on one or more carbons of the backbone of a chemical compound. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the disclosure, the heteroatoms such as nitrogen may have hydrogen substituents, and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic (e.g., $C_6$-$C_{12}$ aryl) or heteroaromatic (e.g., heteroaryl) moiety.

"Optional" or "optionally" means that the subsequently described circumstance may or may not occur, so that the application includes instances where the circumstance occurs and instances where it does not. For example, the phrase "optionally substituted" means that a non-hydrogen substituent may or may not be present on a given atom, and, thus, the application includes structures wherein a non-hydrogen substituent is present and structures wherein a non-hydrogen substituent is not present.

Unless specifically stated as "unsubstituted," references to chemical moieties herein are understood to include substituted variants. For example, reference to an "alkyl" group or moiety implicitly includes both substituted and unsubstituted variants. Examples of substituents on chemical moieties include but is not limited to, halogen, hydroxyl, carbonyl (such as carboxyl, alkoxycarbonyl, formyl, or acyl), thiocarbonyl (such as thioester, thioacetate, or thioformate), alkoxyl, alkylthio, acyloxy, phosphoryl, phosphate, phosphonate, amino, amido, amidine, imine, cyano, nitro, azido, sulfhydryl, alkylthio, sulfate, sulfonate, sulfamoyl, sulfonamido, sulfonyl, heterocyclyl, aralkyl, or aryl or heteroaryl moiety.

"Aryl" indicates an aromatic carbon ring having the indicated number of carbon atoms, for example, 6 to 12 or 6 to 10 carbon atoms, in the ring. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl," as defined herein, regardless of the point of attachment (e.g., both quinolin-5-yl and quinolin-2-yl are heteroaryl groups).

"Heteroaryl" indicates an aromatic ring containing the indicated number of ring atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. 5-Membered heteroaryl is a heteroaryl having 5 ring atoms. 6-Membered heteroaryl is a heteroaryl having 6 ring atoms. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,3,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

The term "acyl" is art-recognized and refers to a group represented by the general formula hydrocarbyl-C(O)—, e.g., alkyl-C(O)—.

The term "alkyl" refers to the radical of saturated aliphatic groups, including straight-chain alkyl groups, and branched-chain alkyl groups. In some embodiments, a straight chain or branched chain alkyl has 30 or fewer carbon atoms in its backbone (e.g., $C_1$-$C_{30}$ for straight chains, $C_4$-$C_{30}$ for branched chains), and in other embodiments 20 or fewer. In certain embodiments, alkyl groups are lower alkyl groups, e.g., methyl, ethyl, n-propyl, i-propyl, n-butyl and n-pentyl. Moreover, the term "alkyl" as used throughout the specification, examples, and claims is intended to include both "unsubstituted alkyls" and "substituted alkyls", the latter of which refers to alkyl moieties having substituents replacing hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In some embodiments, the chain has ten or fewer carbon ($C_1$-$C_{10}$) atoms in its backbone. In other embodiments, the chain has six or fewer carbon ($C_1$-$C_6$) atoms in its backbone.

The terms "hydrazone moiety" or "hydrazone" refer to E and/or Z hydrazones, e.g.,

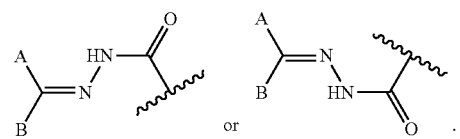

The stereochemistry of the hydrazone moiety can be E or Z. The term hydrazone as used herein includes both E and Z isomers. The hydrazone moieties disclosed herein are generally drawn in one configuration, but it is understood that this disclosure can include both E and/or Z.

At various places in the present specification substituents of compounds of the disclosure are disclosed in groups or in ranges. It is specifically intended that the disclosure include each and every individual sub-combination of the members of such groups and ranges. For example, the term "$C_1$-$C_6$ alkyl" is specifically intended to disclose individually methyl, ethyl, propyl, isopropyl, n-butyl, sec-butyl, isobutyl, etc.

A "pharmaceutically acceptable salt" is a salt of a compound that is suitable for pharmaceutical use, including but not limited to metal salts (e.g., sodium, potassium, magnesium, calcium, etc.), acid addition salts (e.g., mineral acids, carboxylic acids, etc.), and base addition salts (e.g., ammonia, organic amines, etc.). The acid addition salt form of a compound that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like (see, e.g., WO 01/062726. Some pharmaceutically acceptable salts listed by Berge et al., *Journal of Pharmaceutical Sciences*, 66: 1-19 (1977), incorporated herein by reference in its entirety). Compounds containing acidic protons may be converted into their therapeutically active, non-toxic base addition salt form, e.g. metal or amine salts, by treatment with appropriate organic and inorganic bases. Appropriate base salt forms include, for example, ammonium salts, alkali and earth alkaline metal salts or ions, e. g., lithium, sodium, potassium, magnesium, calcium salts and the like, salts with organic bases, e. g. N-methyl-D-glucamine, hydrabamine salts, and salts with amino acids such as, for example, arginine, lysine and the like. Conversely, said salt forms can be converted into the free forms by treatment with an appropriate base or acid. Compounds and their salts can be in the form of a solvate, which is included within the scope of the present disclosure. Such solvates include for example hydrates, alcoholates and the like (see, e.g., WO 01/062726).

The disclosure further provides pharmaceutical compositions comprising one or more compounds of the disclosure together with a pharmaceutically acceptable carrier or excipient. Compounds or pharmaceutical compositions of the disclosure may be used in vitro or in vivo.

The term "isomer" as used herein includes, but is not limited to, tautomers, cis- and trans-isomers (E (entgegen), Z (zusammen)), R- and S-enantiomers (said R and S notation is used in correspondence with the rules described in Pure Appl. Chem. (1976), 45, 11-30), diastereomers, (D)-isomers, (L)-isomers, stereoisomers, the racemic mixtures thereof, and other mixtures thereof. All such isomers, as well as mixtures thereof, are intended to be included in this disclosure. Tautomers, while not explicitly indicated in the formulae described herein, are intended to be included within the scope of the present disclosure.

The disclosure further includes isotopically-labeled or enriched compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, and $^{77}$Br. The radionuclide that is incorporated in the instant radio-labeled compounds will depend on the specific application of that radio-labeled compound. For example, for in vitro metalloprotease labeling and competition assays, compounds that incorporate $^{3}$H, $^{14}$C, $^{82}$Br, $^{35}$S or will generally be most useful. For radio-imaging applications $^{11}$C, $^{18}$F, $^{75}$Br, $^{76}$Br or $^{77}$Br will generally be most useful. Tritium ($^{3}$H) and $^{14}$C may be useful for ADME studies. In some embodiments, each alkyl, cycloalkyl, alkene, alkylene, and alkoxy is optionally substituted by one or more -D or -F.

Compounds of the Disclosure

Embodiments of the present disclosure provide a compound having the structure represented by Formula (I):

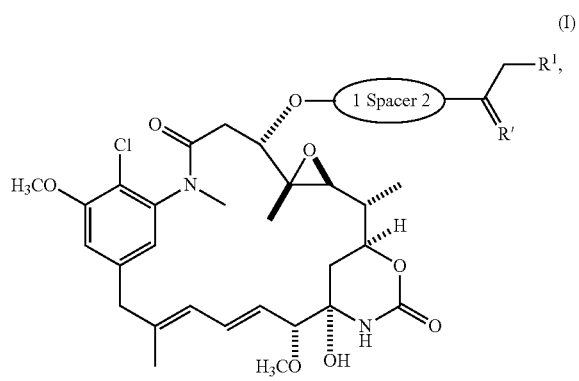

(I)

or a pharmaceutically acceptable salt, hydrate, solvate, or isomer thereof, wherein:

$R^1$ is selected from —H and $C_1$-$C_4$ alkyl;

Spacer is selected from:

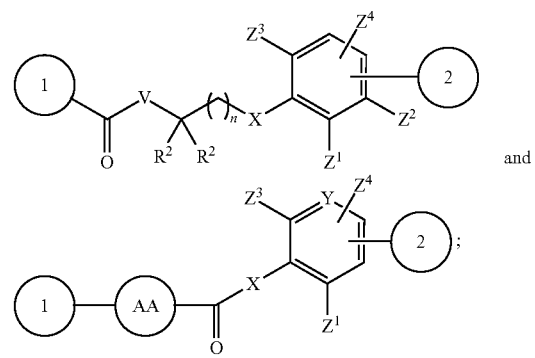

and

V is absent or selected from —$CH_2$—, —O— and —$NR^3$—, wherein $R^3$ is —H or $C_1$-$C_4$ alkyl;

each $R^2$ is independently selected from —H, halogen (e.g., —F, —Cl, —Br or —I) and $C_1$-$C_4$ alkyl or two $R^2$s taken together form a $C_3$-$C_6$, cycloalkyl;

n is 0-3;

X is absent or selected from —$CH_2$—, —O—, —S—, —Se—, and —$NR^4$—, wherein $R^4$ is —H or $C_1$-$C_4$ alkyl;

Y is selected from =CH— and =N—;

$Z^1$, $Z^2$, $Z^3$ and $Z^4$ are each independently selected from —H, halogen (e.g., —F, —Cl, —Br or —I), —$CF_3$, —$OCH_3$, —CN, —$NO_2$, $C_1$-$C_4$ alkyl and $C_2$-$C_4$ alkoxy;

AA is an amino acid selected from glycine, D or L proline, sarcosine, N-ethyl-glycine, D or L alanine, D or L N-methyl-alanine, β-alanine, N-methyl-β-alanine, α-aminoisobutyric acid, and N-methyl-α-aminoisobutyric acid;

R' is selected from O and

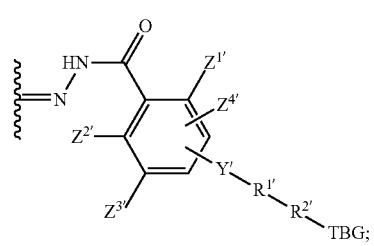

Y' is absent or selected from an optionally substituted $C_1$-$C_6$ alkyl, —NH—C(O)—, and —C(O)—NH—; or Y' is selected from the group consisting of:

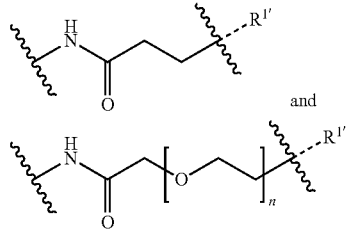

and wherein n=0-6;
R$^{1'}$ is absent or selected from the group consisting of:

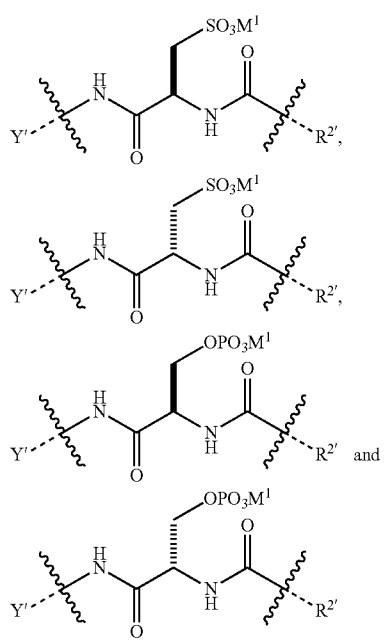

wherein M$^1$ is a pharmaceutically acceptable counter ion (e.g., H$^+$, Na$^+$, K$^+$, Ca$^{2+}$, Mg$^{2+}$, NR$_4^+$, and NHR$_3^+$; wherein R is H or $C_1$-$C_4$ alkyl);
R$^{2'}$ is optionally substituted $C_1$-$C_{18}$ alkyl wherein optionally up to six carbon atoms in said $C_1$-$C_{18}$ alkyl are each independently replaced with —OCH$_2$CH$_2$—;
Z$^{1'}$, Z$^{2'}$, Z$^{3'}$ and Z$^{4'}$ are each independently selected from —H, halogen (e.g., —F, —Cl, —Br or —I), —CF$_3$, —OCH$_3$, —CN, —NO$_2$, —SO$_3$M$^2$, and $C_1$-$C_4$ alkyl wherein M$^2$ is a pharmaceutically acceptable counter ion (e.g., H$^+$, Na$^+$, K$^+$, Ca$^{2+}$, Mg$^{2+}$, NR$_4^+$, and NHR$_3^+$; wherein R is H or $C_1$-$C_4$ alkyl);
TBG is a thiol-binding group selected from an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, an optionally substituted acetylene group, and an optionally substituted N-hydroxysuccinimide ester group;
wherein said TBG is optionally bound to a thiol-bearing macromolecular carrier or thiol-bearing tumor-specific carrier.

In some embodiments, in the compound of Formula (I), R$^1$ is selected from —H and $C_1$-$C_4$ alkyl;

Spacer is selected from:

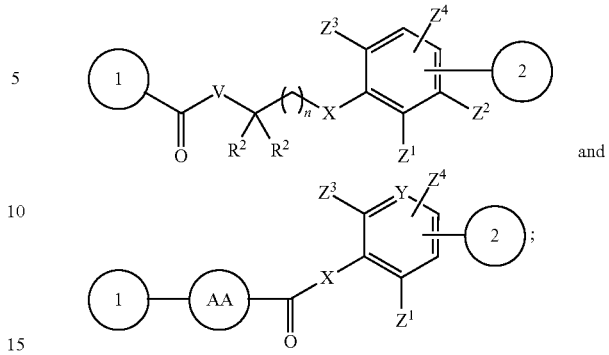

and

V is absent or selected from —CH$_2$—, —O— and —NR$^3$—, wherein R$^3$ is —H or $C_1$-$C_4$ alkyl;
each R$^2$ is independently selected from —H, halogen (e.g., —F, —Cl, —Br or —I) and $C_1$-$C_4$ alkyl or two R$^2$s taken together form a $C_3$-$C_6$, cycloalkyl;
n is 0-3;
X is absent or selected from —CH$_2$—, —O—, —S—, —Se—, and —NR$^4$—, wherein R$^4$ is —H or $C_1$-$C_4$ alkyl;
Y is selected from =CH— and =N—;
Z$^1$, Z$^2$, Z$^3$ and Z$^4$ are each independently selected from —H, halogen (e.g., —F, —Cl, —Br or —I), —CF$_3$, —OCH$_3$, —CN, —NO$_2$, $C_1$-$C_4$ alkyl and $C_2$-$C_4$ alkoxy;
AA is an amino acid selected from glycine, D or L proline, sarcosine, D or L alanine, D or L N-methylalanine, β-alanine, N-methyl-β-alanine, α-aminoisobutyric acid, and N-methyl-α-aminoisobutyric acid;
R' is selected from O and

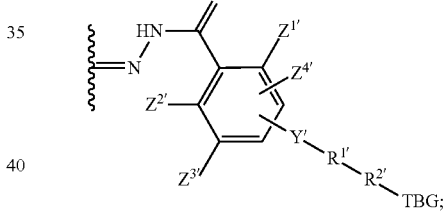

Y' is absent or selected from an optionally substituted $C_1$-$C_6$ alkyl, —NH—C(O)—, and —C(O)—NH—; or Y' is selected from the group consisting of:

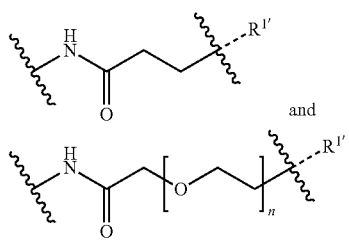

and wherein n=0-6;
R$^{1'}$ is absent or selected from the group consisting of:

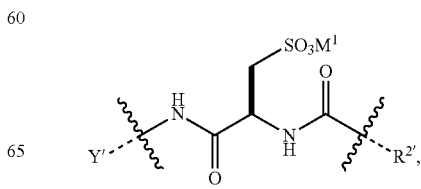

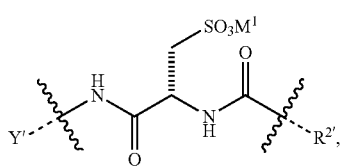

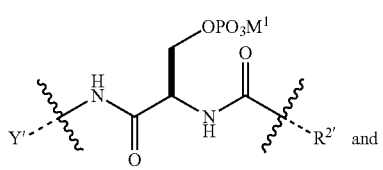

and

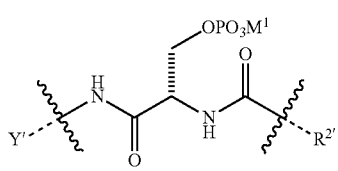

wherein M¹ is a pharmaceutically acceptable counter ion (e.g., H⁺, Na⁺, K⁺, Ca²⁺, Mg²⁺, NR₄⁺, and NHR₃⁺; wherein R is H or $C_1$-$C_4$ alkyl);

$R^{2'}$ is optionally substituted $C_1$-$C_{18}$ alkyl wherein optionally up to six carbon atoms in said $C_1$-$C_{18}$ alkyl are each independently replaced with —OCH₂CH₂—;

$Z^{1'}$, $Z^{2'}$, $Z^{3'}$ and $Z^{4'}$ are each independently selected from —H, halogen (e.g., —F, —Cl, —Br or —I), —CF₃, —OCH₃, —CN, —NO₂, —SO₃M², and $C_1$-$C_4$ alkyl wherein M² is a pharmaceutically acceptable counter ion (e.g., H⁺, Na⁺, K⁺, Ca²⁺, Mg²⁺, NR₄⁺, and NHR₃⁺; wherein R is H or $C_1$-$C_4$ alkyl);

TBG is a thiol-binding group selected from an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, an optionally substituted acetylene group, and an optionally substituted N-hydroxysuccininide ester group;

wherein said TBG is optionally bound to a thiol-bearing macromolecular carrier or thiol-bearing tumor-specific carrier.

In some embodiments, R' is O. These novel compounds can represent active species, and may be, e.g., the active component of a drug delivery system or an active metabolite that is released from a drug delivery system.

In certain embodiments, the compound of Formula (I) where R' is 0 has a structure of any one of Formulae (II'), (III') and (IV'):

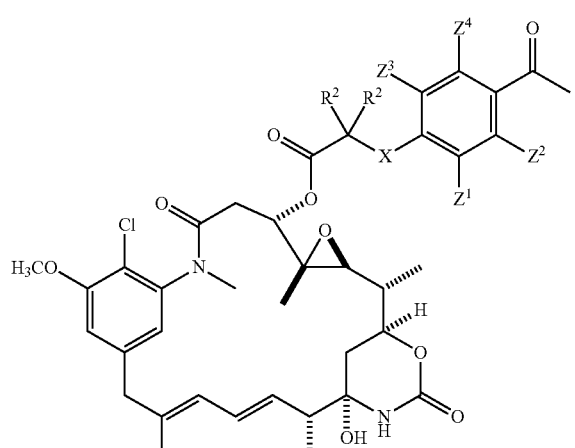

Formula (II')

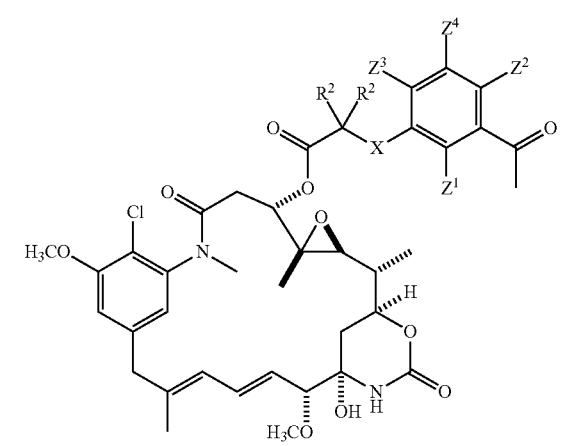

Formula (III')

or a pharmaceutically acceptable salt, hydrate, solvate, or isomer thereof,
wherein:
each R² is independently selected from —H, and $C_1$-$C_4$ alkyl or two R²s taken together form a $C_3$-$C_6$, cycloalkyl;
X is absent or selected from —CH₂—, —O—, —S— and —NR³—, wherein R³ is —H or $C_1$-$C_4$ alkyl;
$Z^1$, $Z^2$, $Z^3$ and $Z^4$ are each independently selected from —H, halogen (e.g., —F, —Cl, —Br or —I), —CF₃, —OCH₃, —NO₂ and —CH₃;

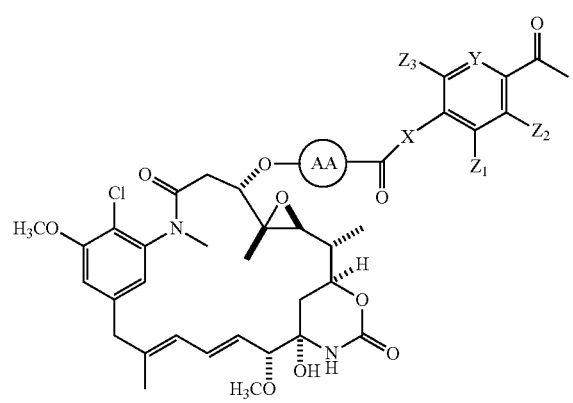

Formula (IV')

or a pharmaceutically acceptable salt, hydrate, solvate, or isomer thereof, wherein:

X is absent or selected from —CH$_2$— and —NH—;

Y is =CH— or =N—;

Z$^1$, Z$^2$, Z$^3$ and Z$^3$ are each independently selected from —H, halogen (e.g., —F, —Cl, —Br or —I), —CF$_3$, —OCH$_3$, —NO$_2$ and —CH$_3$;

AA is an amino acid selected from glycine, D or L proline, sarcosine, N-ethyl-glycine, D or L alanine, D or L N-methyl-alanine, β-alanine, N-methyl-β-alanine, α-aminoisobutyric acid, and N-methyl-α-aminoisobutyric acid.

In yet other embodiments, in the compounds of Formula (IV'):

X is absent or selected from —CH$_2$— and —NH—; Y is =CH— or =N—;

Z$^1$, Z$^2$, Z$^3$ and Z$^3$ are each independently selected from —H, halogen (e.g., —F, —Cl, —Br or —I), —CF$_3$, —OCH$_3$, —NO$_2$ and —CH$_3$;

AA is an amino acid selected from glycine, D or L proline, sarcosine, D or L alanine, D or L N-methylalanine, β-alanine, N-methyl-β-alanine, α-aminoisobutyric acid, and N-methyl-α-aminoisobutyric acid.

In some embodiments, the compound is selected from the following specific compounds:

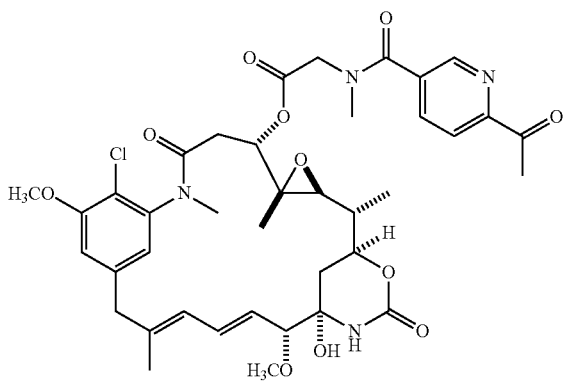

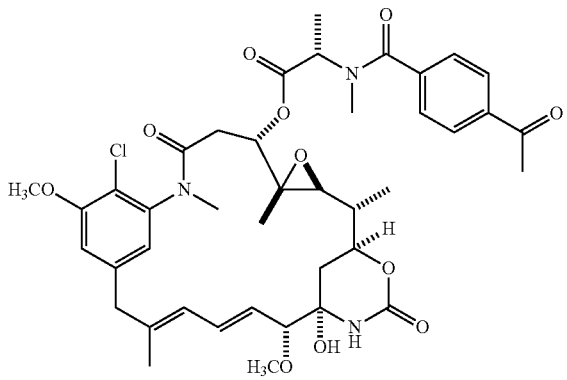

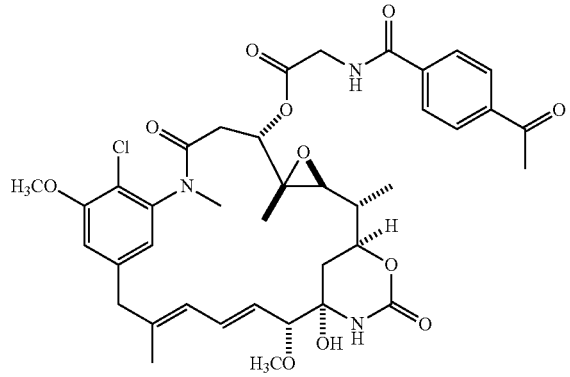

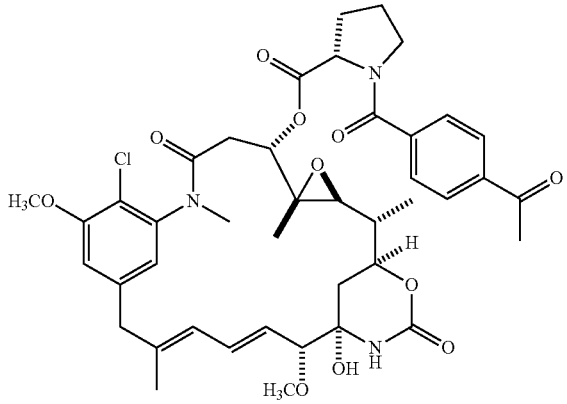

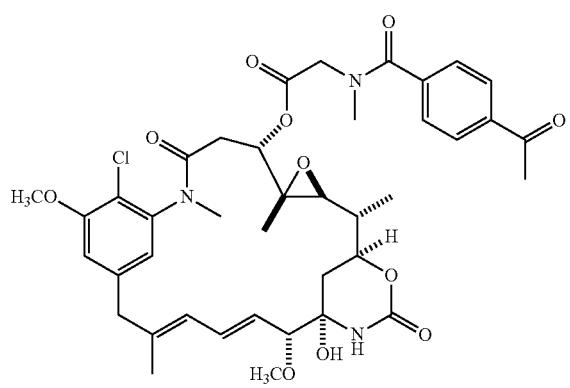

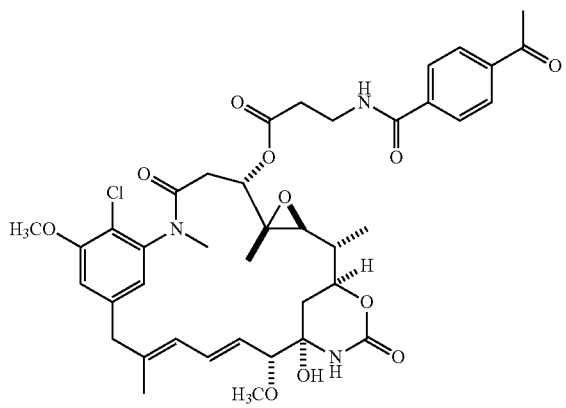

-continued
41
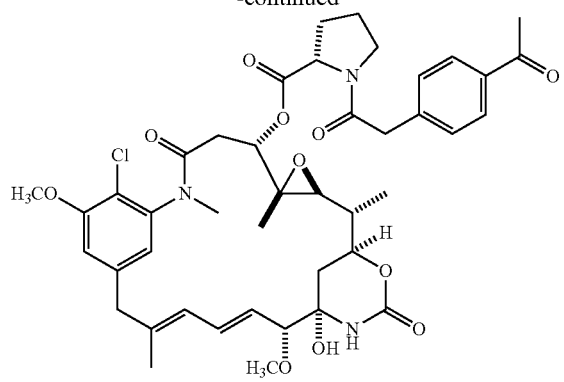
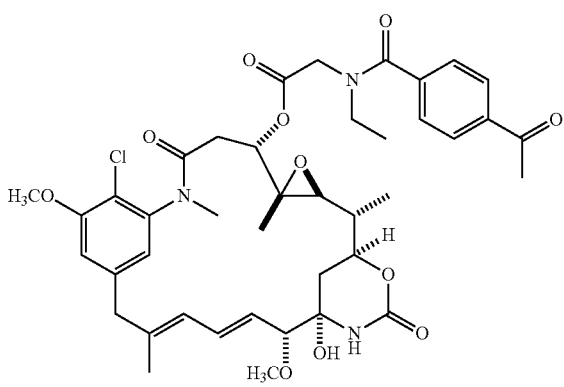
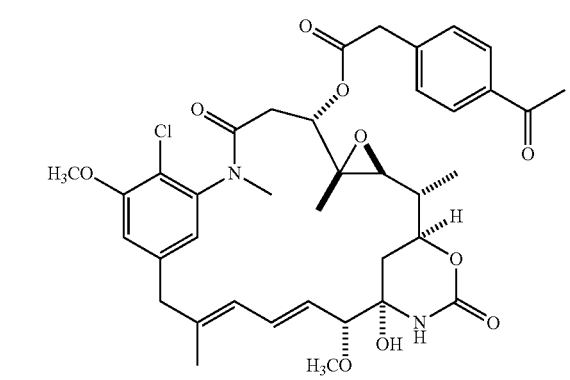
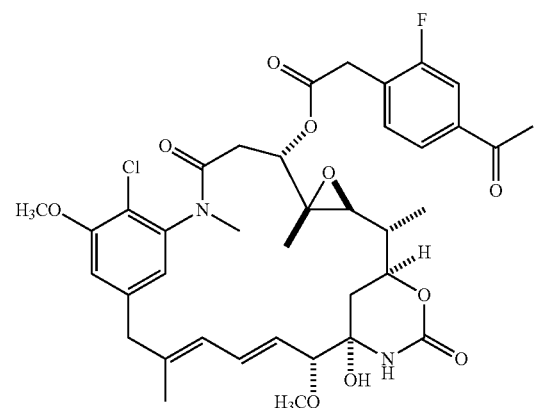
-continued
42
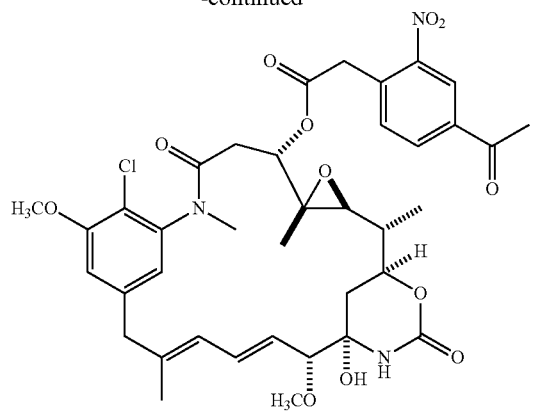
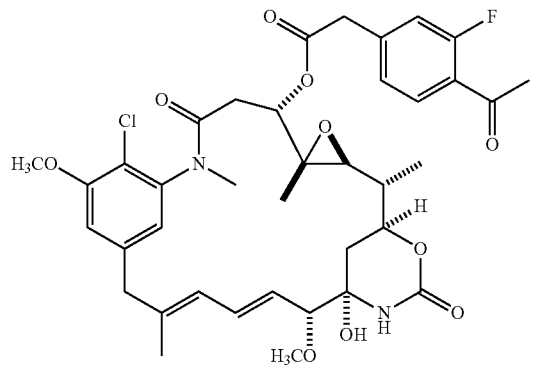
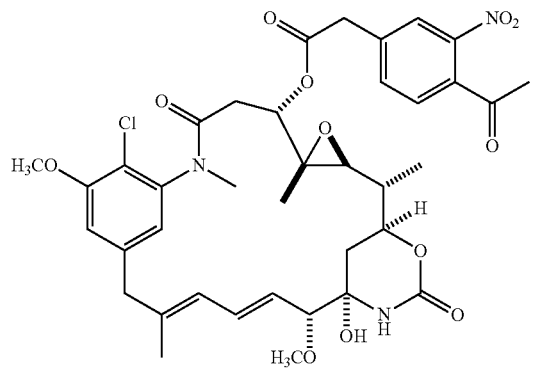
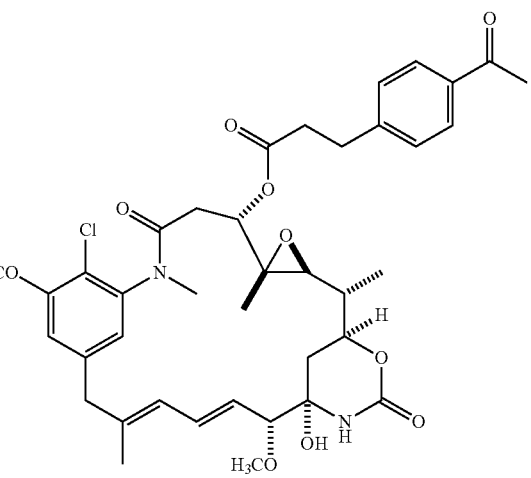

43
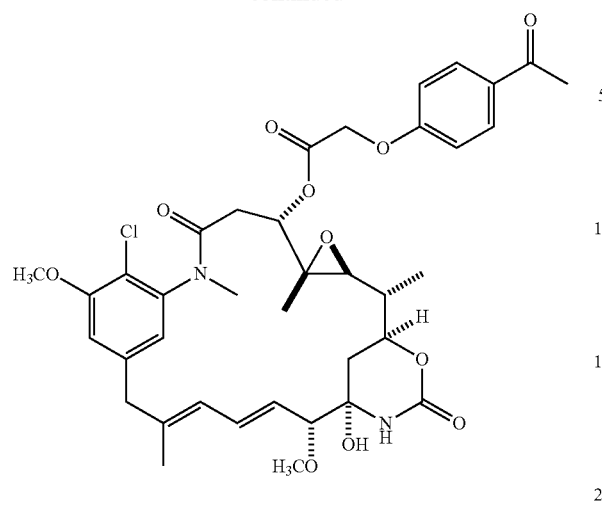
44
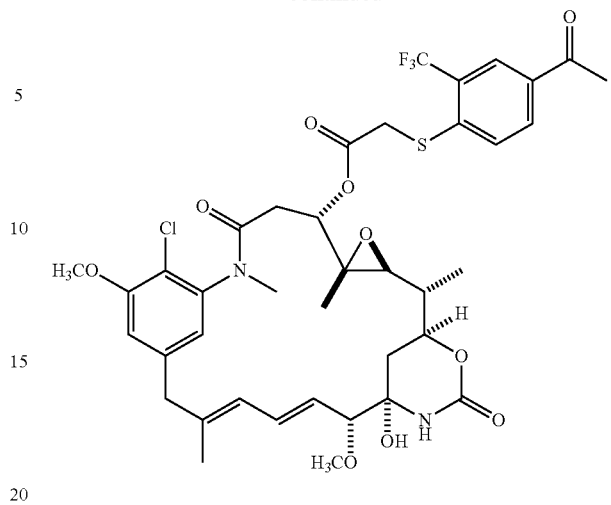
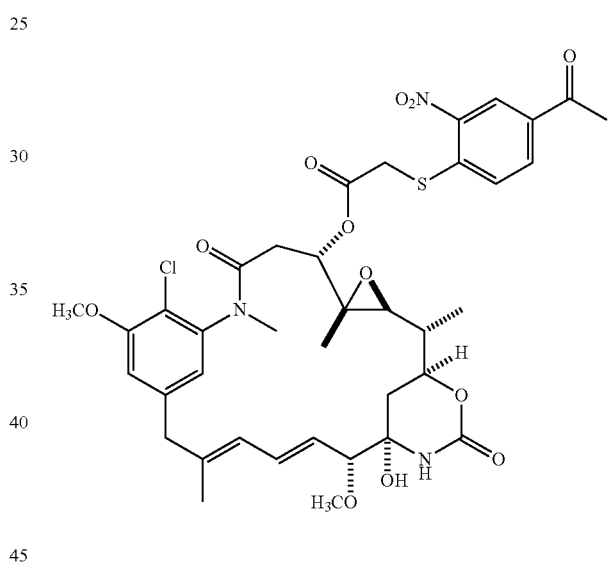
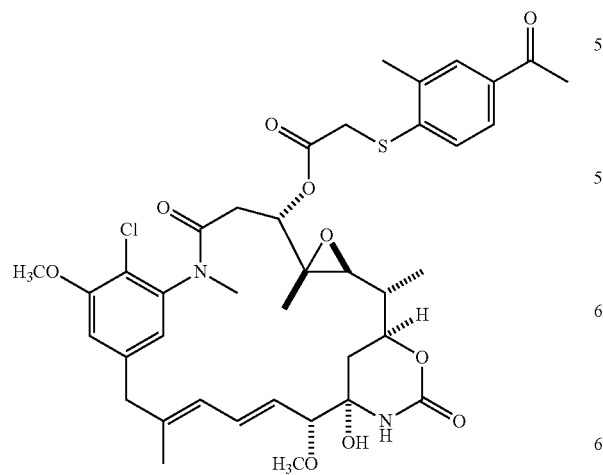
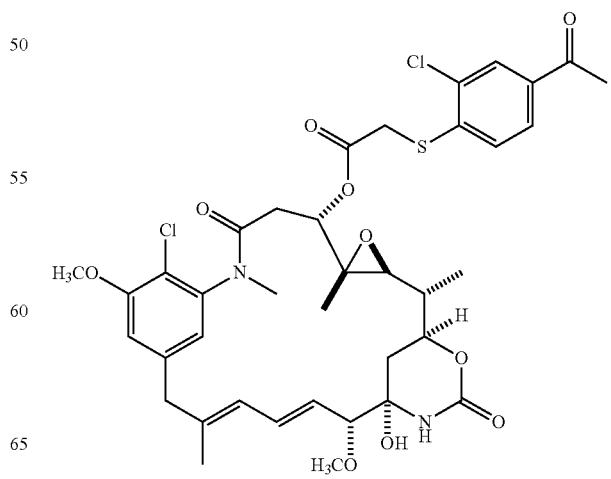

45
-continued
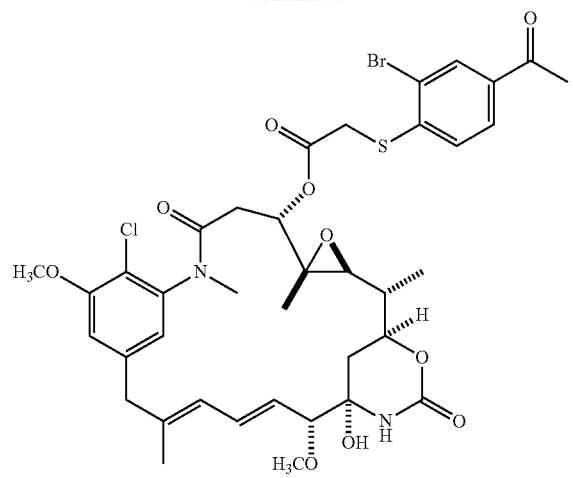
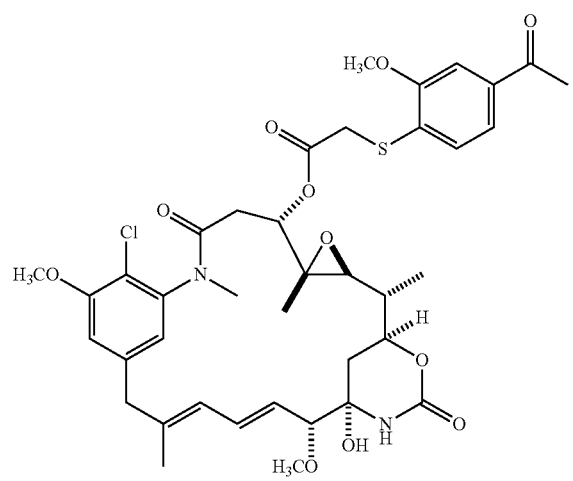
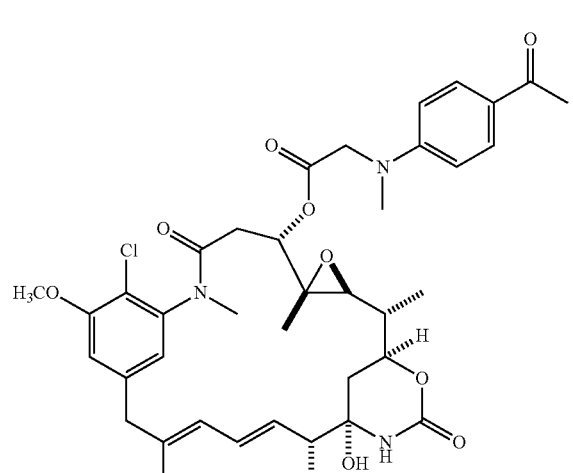
46
-continued
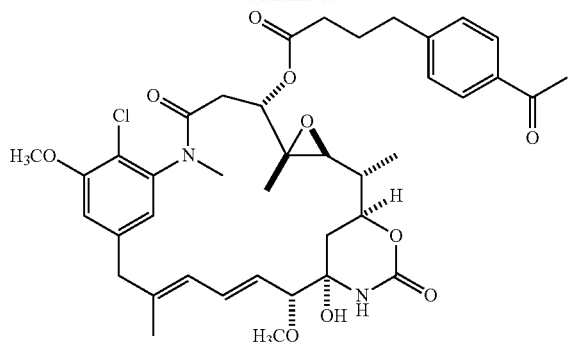
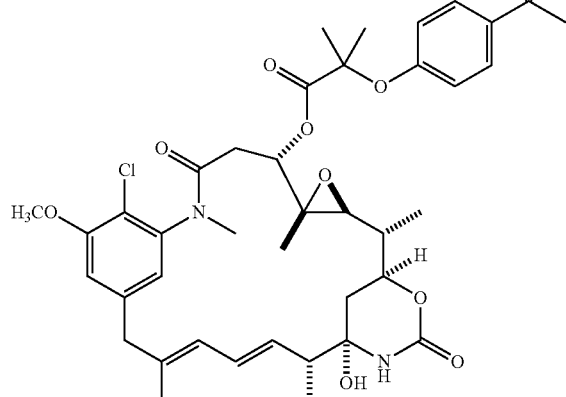
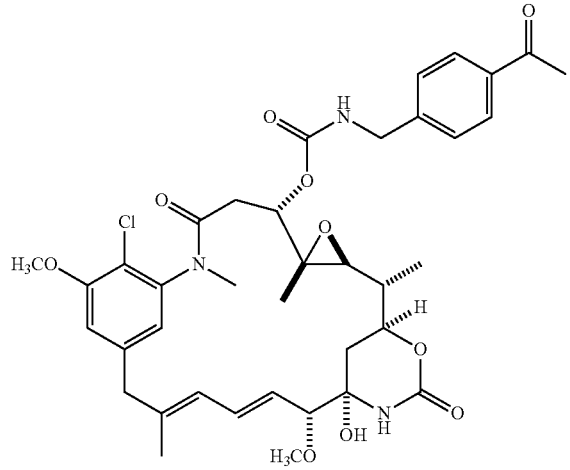
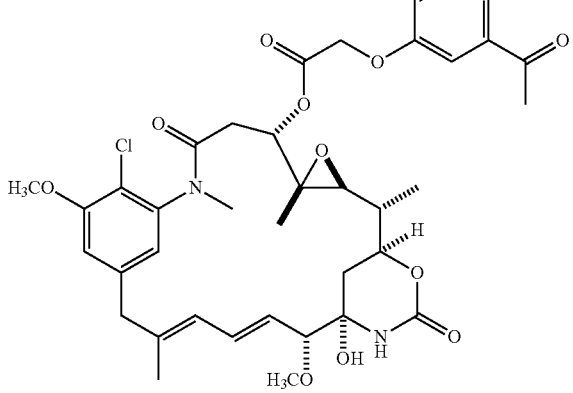

or a pharmaceutically acceptable salt, hydrate, solvate, or isomer thereof.

Other embodiments include prodrugs, e.g., those represented by Formula (I) where R' is:

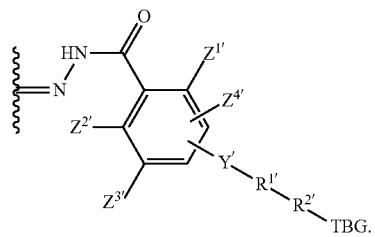

These novel compounds can represent a drug delivery system whereby an active metabolite is released selectively from a drug delivery system. These include, e.g., albumin-binding prodrugs.

In certain embodiments, these compounds have a structure of any one of Formulae (II), (III), and (IV):

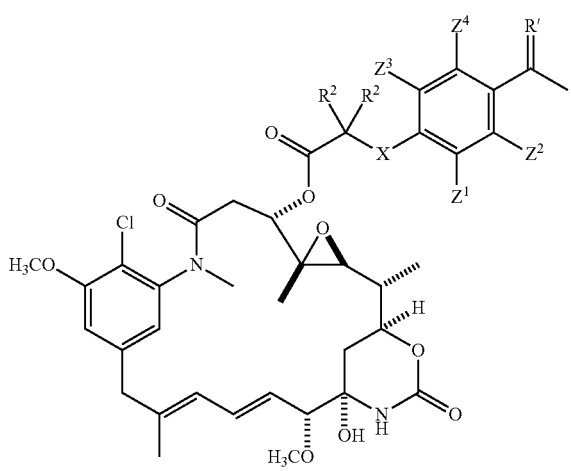
Formula (II)

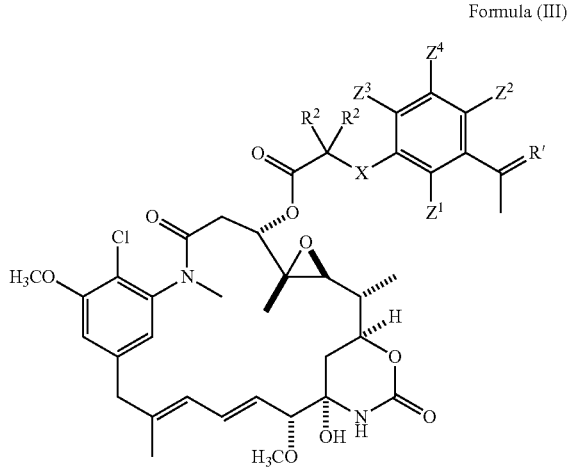
Formula (III)

or a pharmaceutically acceptable salt, hydrate, solvate, or isomer thereof,
wherein:
each $R^2$ is independently selected from —H, and $C_1$-$C_4$ alkyl or two $R^2$s taken together form a $C_3$-$C_6$-cycloalkyl;

X is absent or selected from —$CH_2$—, —O—, —S— and —$NR^3$—, wherein $R^3$ is —H or $C_1$-$C_4$ alkyl;

$Z^1$, $Z^2$, $Z^3$ and $Z^4$ are each independently selected from —H, halogen (e.g., —F, —Cl, —Br or —I), —$CF_3$, —$OCH_3$, —$NO_2$ and —$CH_3$;

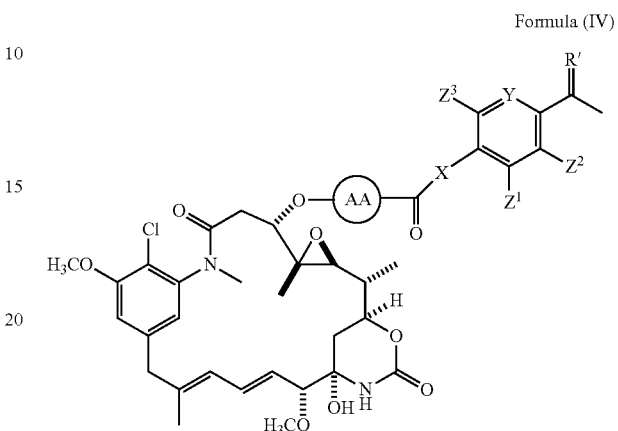
Formula (IV)

or a pharmaceutically acceptable salt, hydrate, solvate, or isomer thereof,
wherein:
X is absent or selected from —$CH_2$— and —NH—;
Y is =CH— or =N—;
$Z^1$, $Z^2$, $Z^3$ and $Z^3$ are each independently selected from —H, halogen (e.g., —F, —Cl, —Br or —I), —$CF_3$, —$OCH_3$, —$NO_2$ and —$CH_3$;
AA is an amino acid selected from glycine, D or L proline, sarcosine, N-ethyl-glycine, D or L alanine, D or L N-methylalanine, β-alanine, N-methyl-β-alanine, α-aminoisobutyric acid, and N-methyl-α-aminoisobutyric acid; and
where R' is:

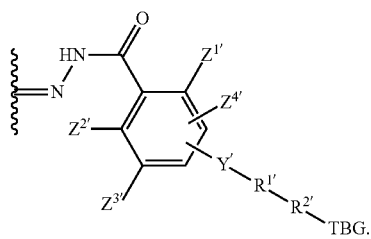

In yet other embodiments, in the compounds of Formula (IV'):
X is absent or selected from —$CH_2$— and —NH—;
Y is =CH— or =N—;
$Z^1$, $Z^2$, $Z^3$ and $Z^3$ are each independently selected from —H, halogen (e.g., —F, —Cl, —Br or —I), —$CF_3$, —$OCH_3$, —$NO_2$ and —$CH_3$;
AA is an amino acid selected from glycine, D or L proline, sarcosine, D or L alanine, D or L N-methylalanine, β-alanine, N-methyl-β-alanine, α-aminoisobutyric acid, and N-methyl-α-aminoisobutyric acid; and where R' is:

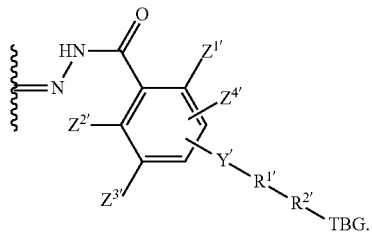

In some embodiments, $R^1$ is —H. In other embodiments, at least one of $Z^1$, $Z^2$, $Z^3$ and $Z^4$ is not H and/or at least one of $Z^1$, $Z^2$, $Z^3$ and $Z^4$ is —F or —NO$_2$. In some embodiments, when n is 0, X is absent. In other embodiments, when n is 0, X is —CH$_2$—. In some embodiments, n is 0 and X is —O— or —S—. Additional embodiments include pharmaceutically acceptable salts, solvates, hydrates, tautomers, and solid forms of the disclosed compounds.

In some embodiments, the compound is selected from the following specific compounds:

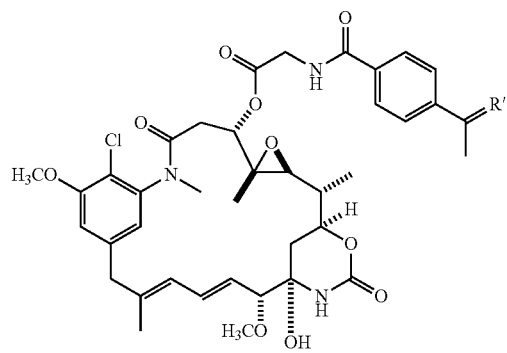

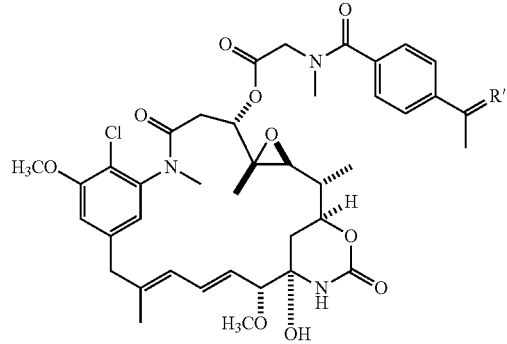

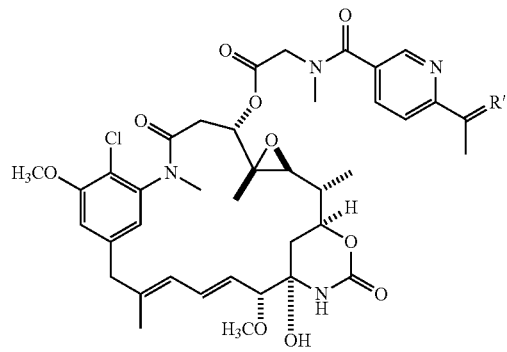

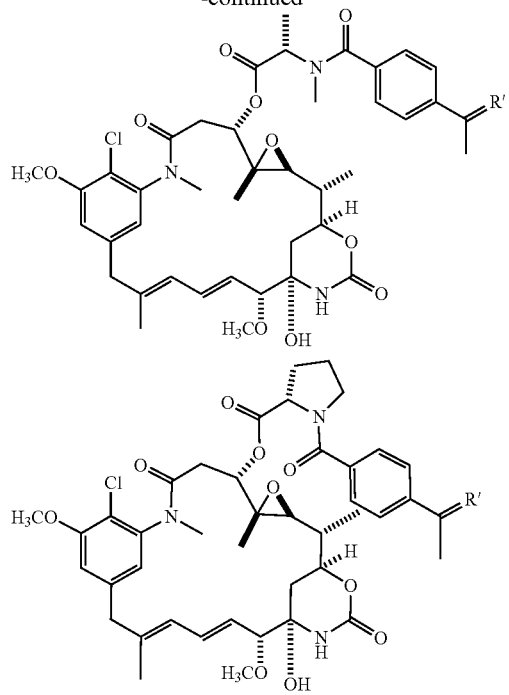

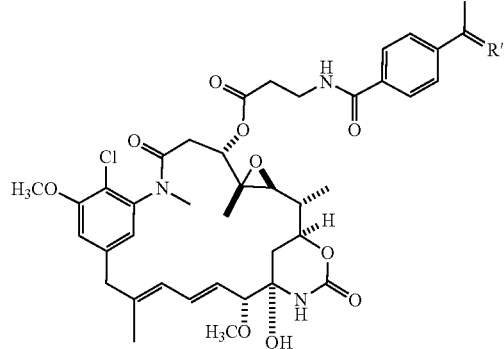

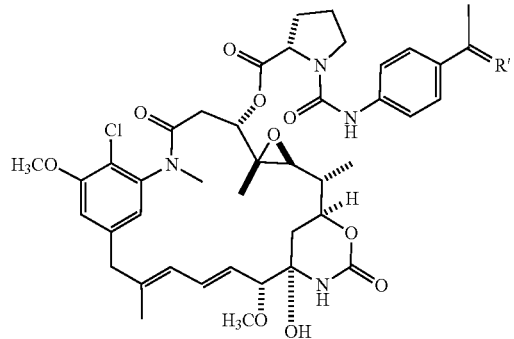

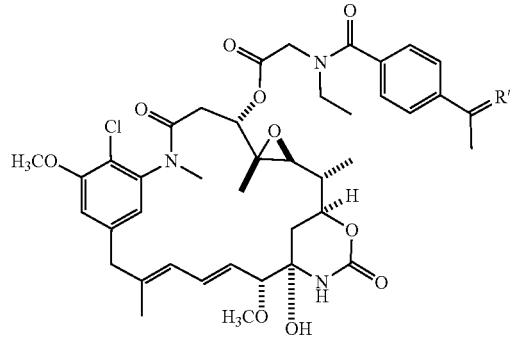

51
-continued
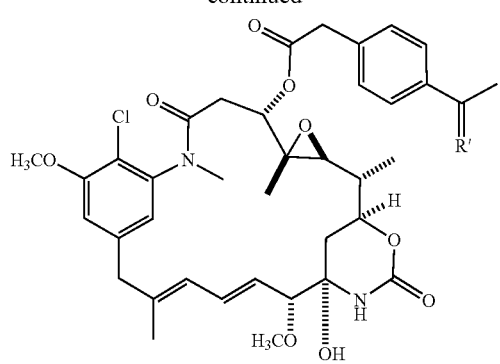
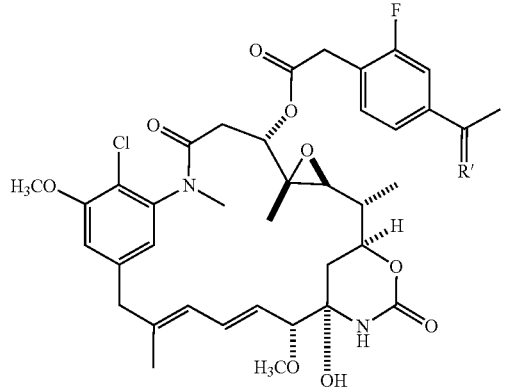
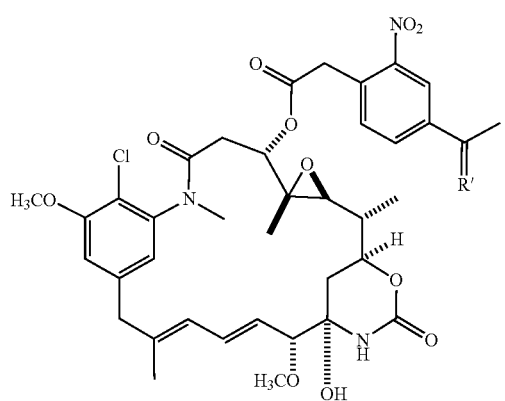
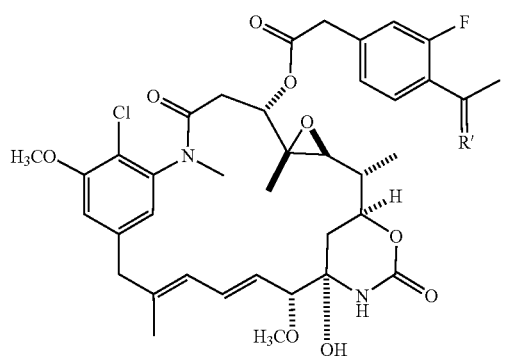
52
-continued
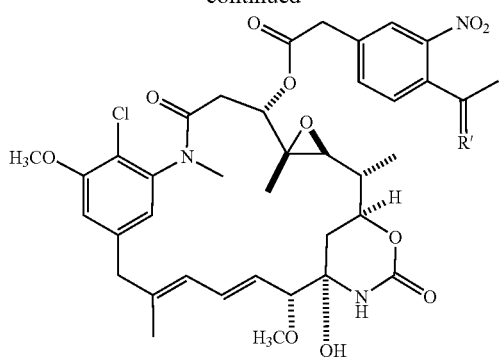
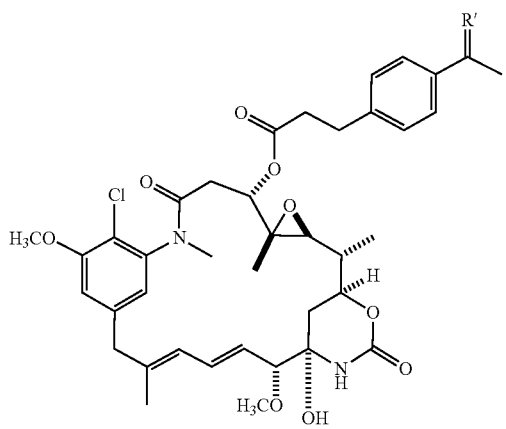
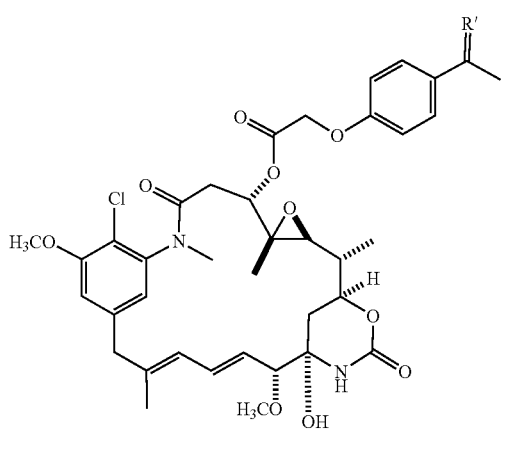
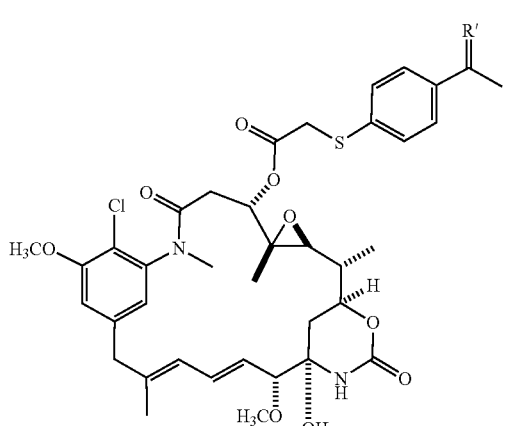

53
-continued
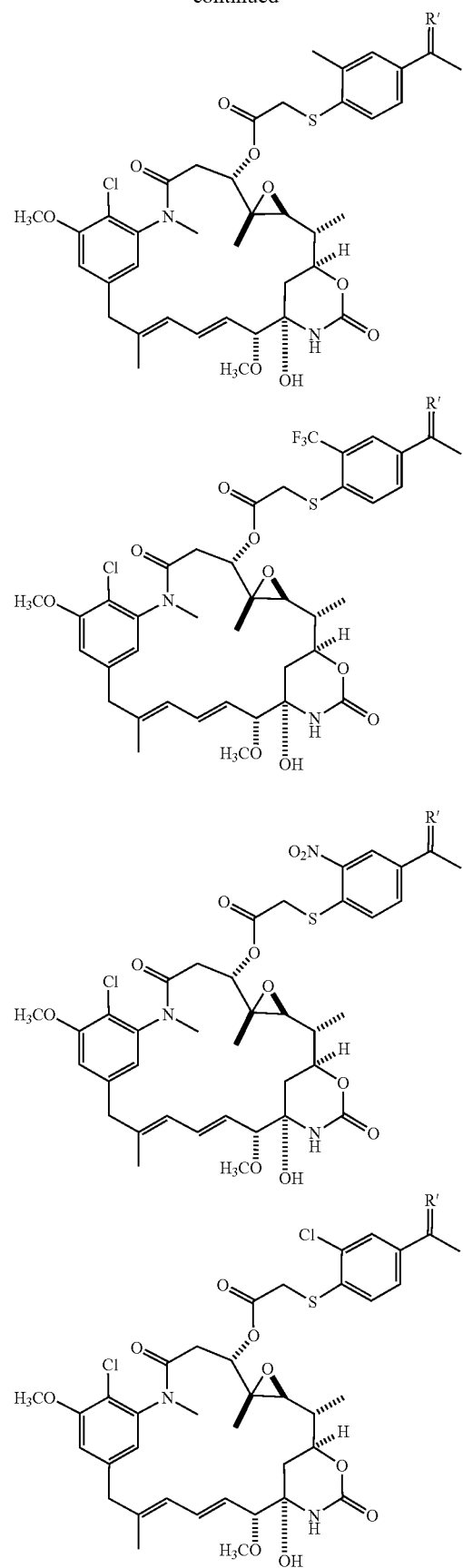
54
-continued
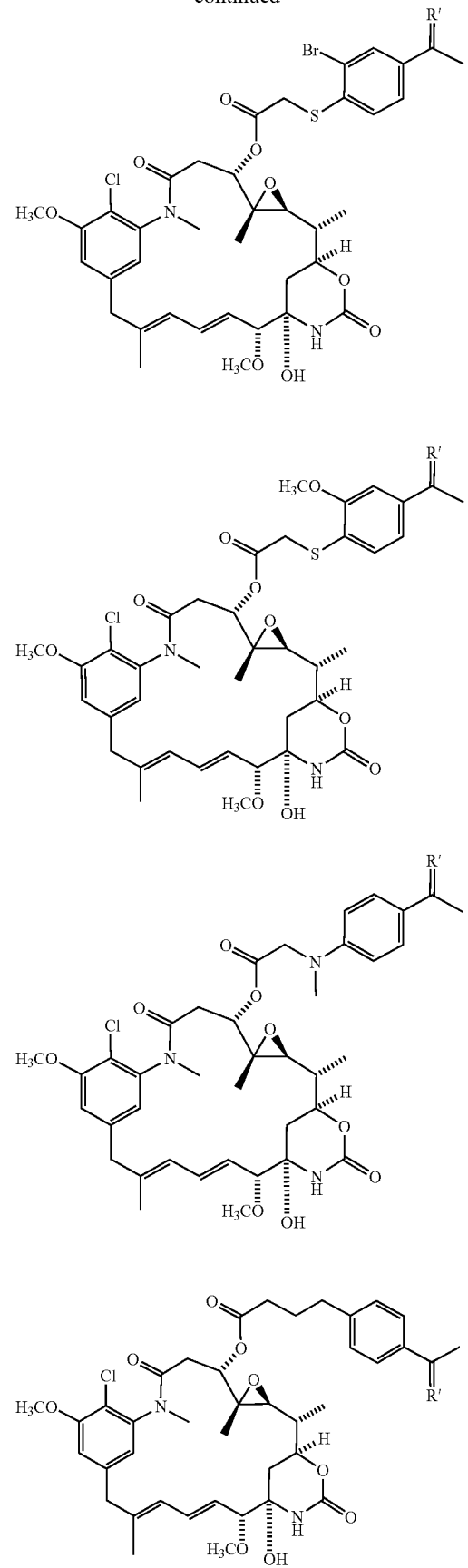

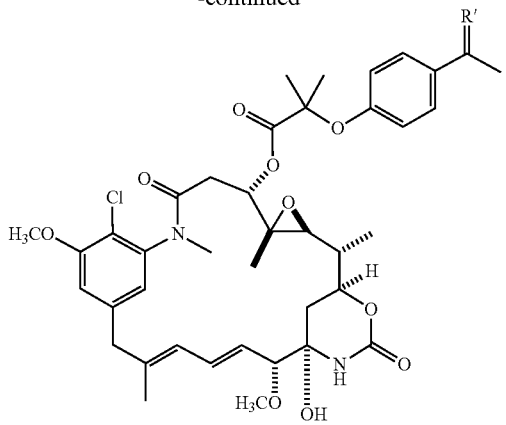

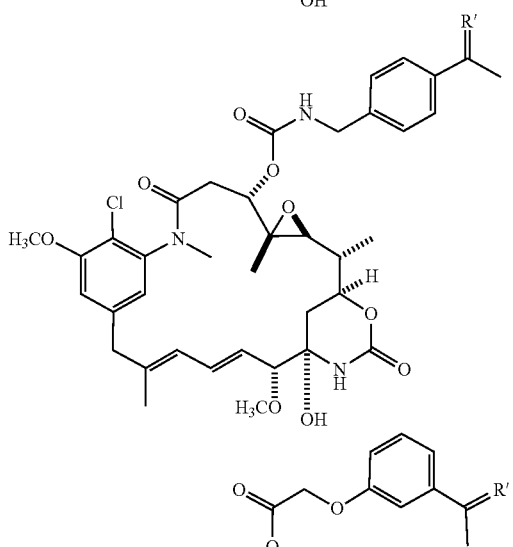

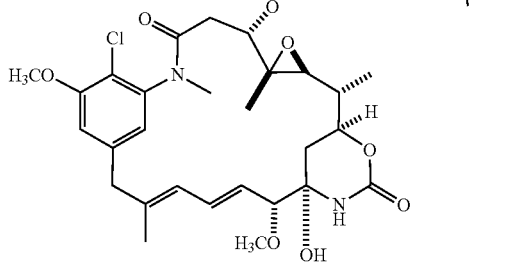

or a pharmaceutically acceptable salt, hydrate, solvate, or isomer thereof.

In certain embodiments, the compound is not bound to a thiol-bearing macromolecular carrier or thiol-bearing tumor-specific carrier. In other embodiments, the compound is bound to a thiol-bearing macromolecular carrier or thiol-bearing tumor-specific carrier. For example, the thiol-bearing macromolecular carrier or thiol-bearing tumor-specific carrier is selected from endogenous albumin, exogenous albumin, an antibody, an antibody fragment, a peptide, a natural or synthetic polymer, a liposome and a nanoparticle.

In some embodiments, the TBG is an optionally substituted maleimide group, for example, an unsubstituted maleimide group. In some embodiments, the maleimide group binds rapidly and selectively to the cysteine-34 of albumin after administration to a subject, such as a human.

In some embodiments, Z" is selected from —$NO_2$ or —$SO_3M^2$ and/or and Y' is selected from —NHC(O)— or

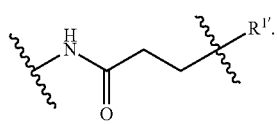

In some embodiments, $R^{1'}$ is

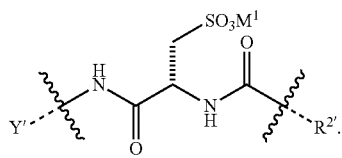

In some embodiments, $R^{2'}$ is selected from optionally substituted $C_1$-$C_{18}$ alkyl wherein optionally up to six carbon atoms in said $C_1$-$C_{18}$ alkyl are each independently replaced with —$OCH_2CH_2$— (e.g., 1, 2, 3, 4, 5 or 6 six carbon atoms are replaced with —$OCH_2CH_2$—).

In some embodiments, R' is:

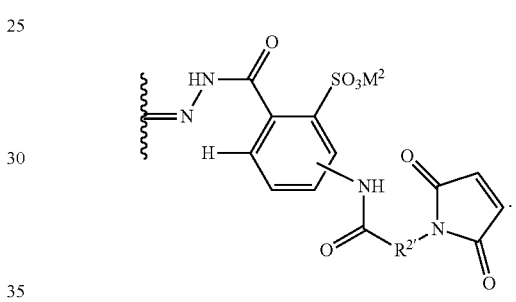

For example, R' may be:

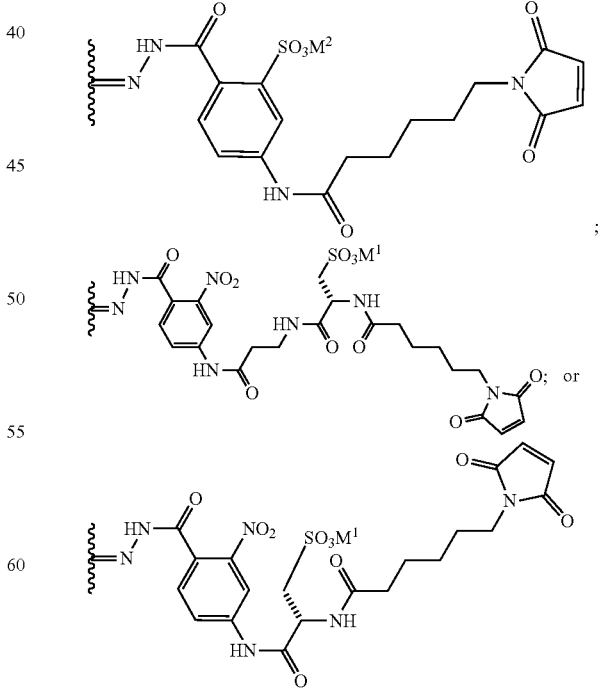

Specific compounds within the present disclosure include the following:

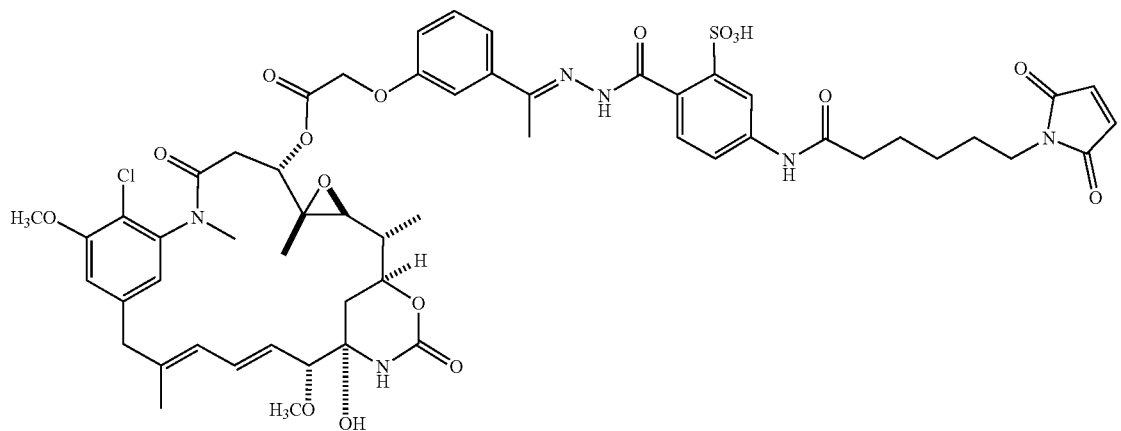
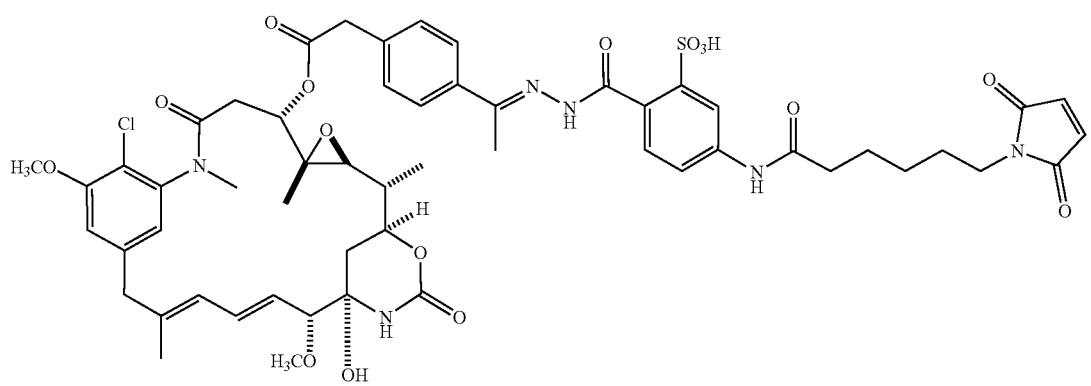
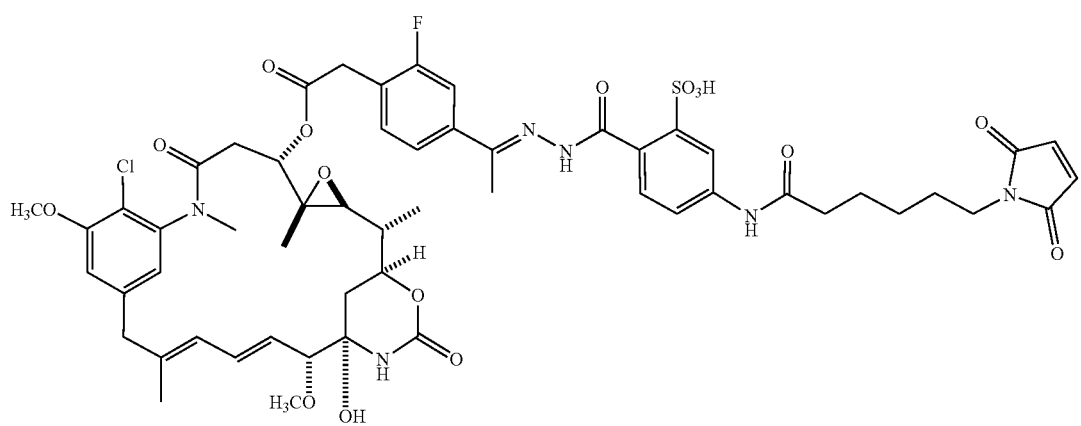

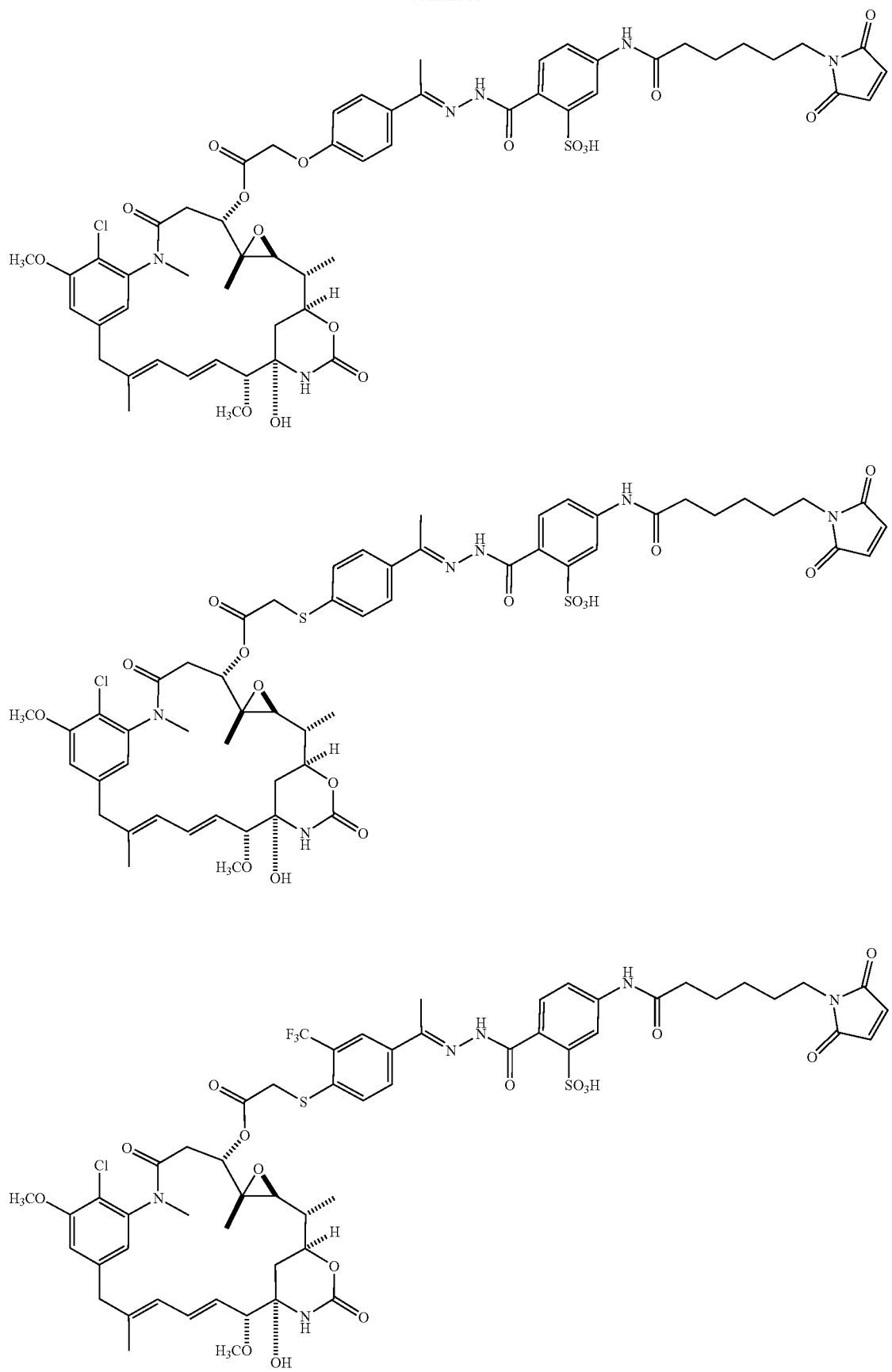

-continued
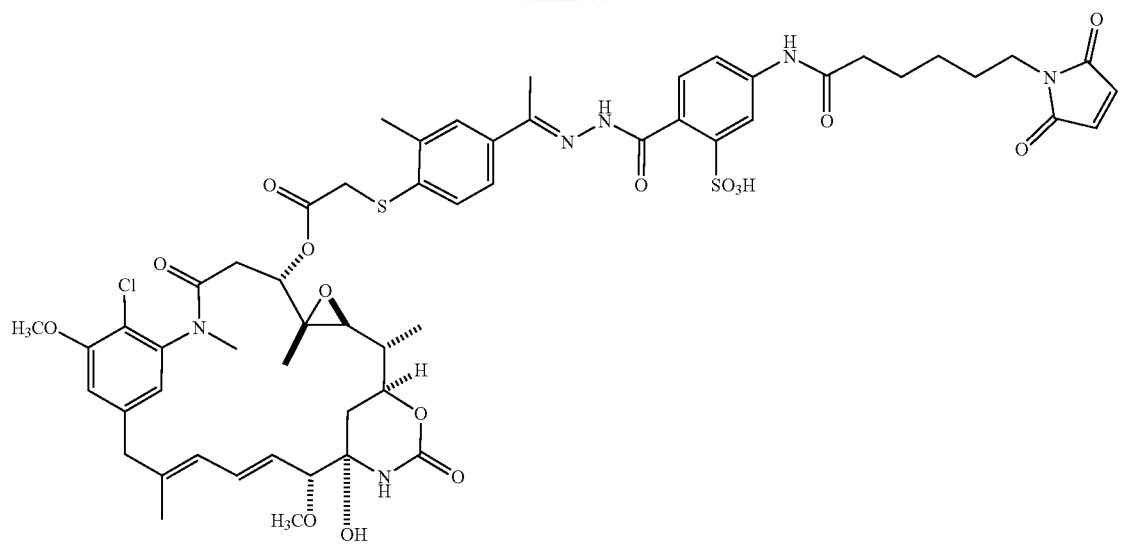
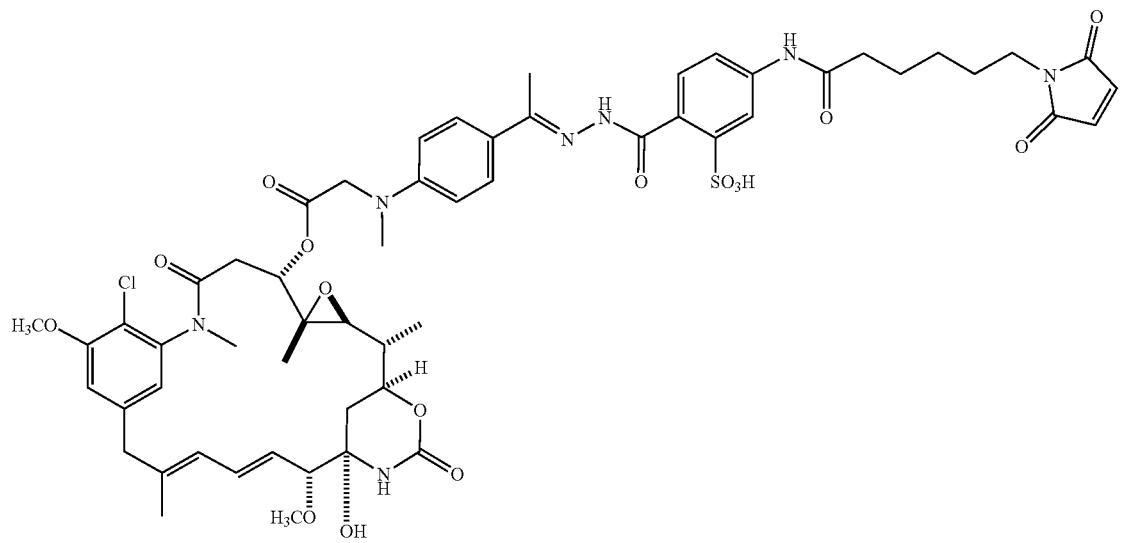
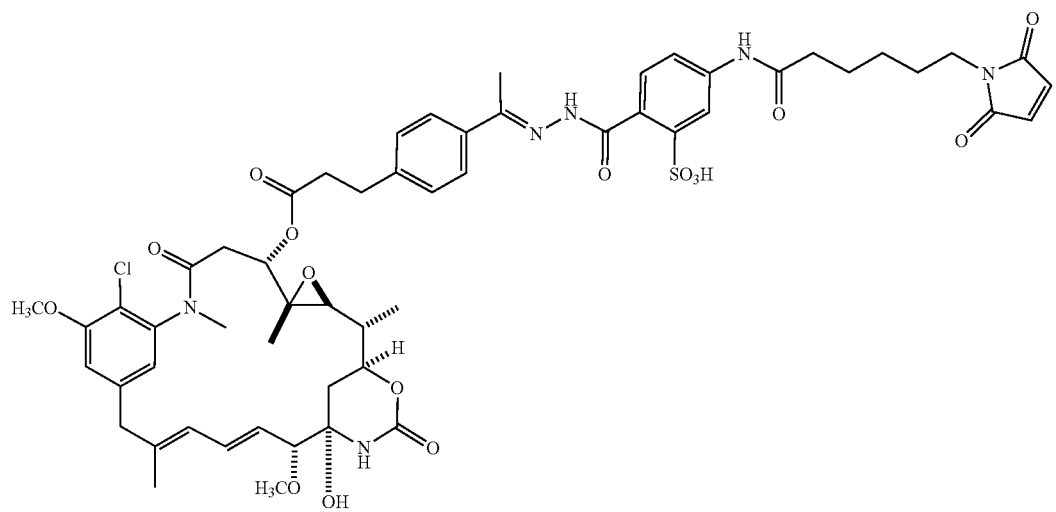

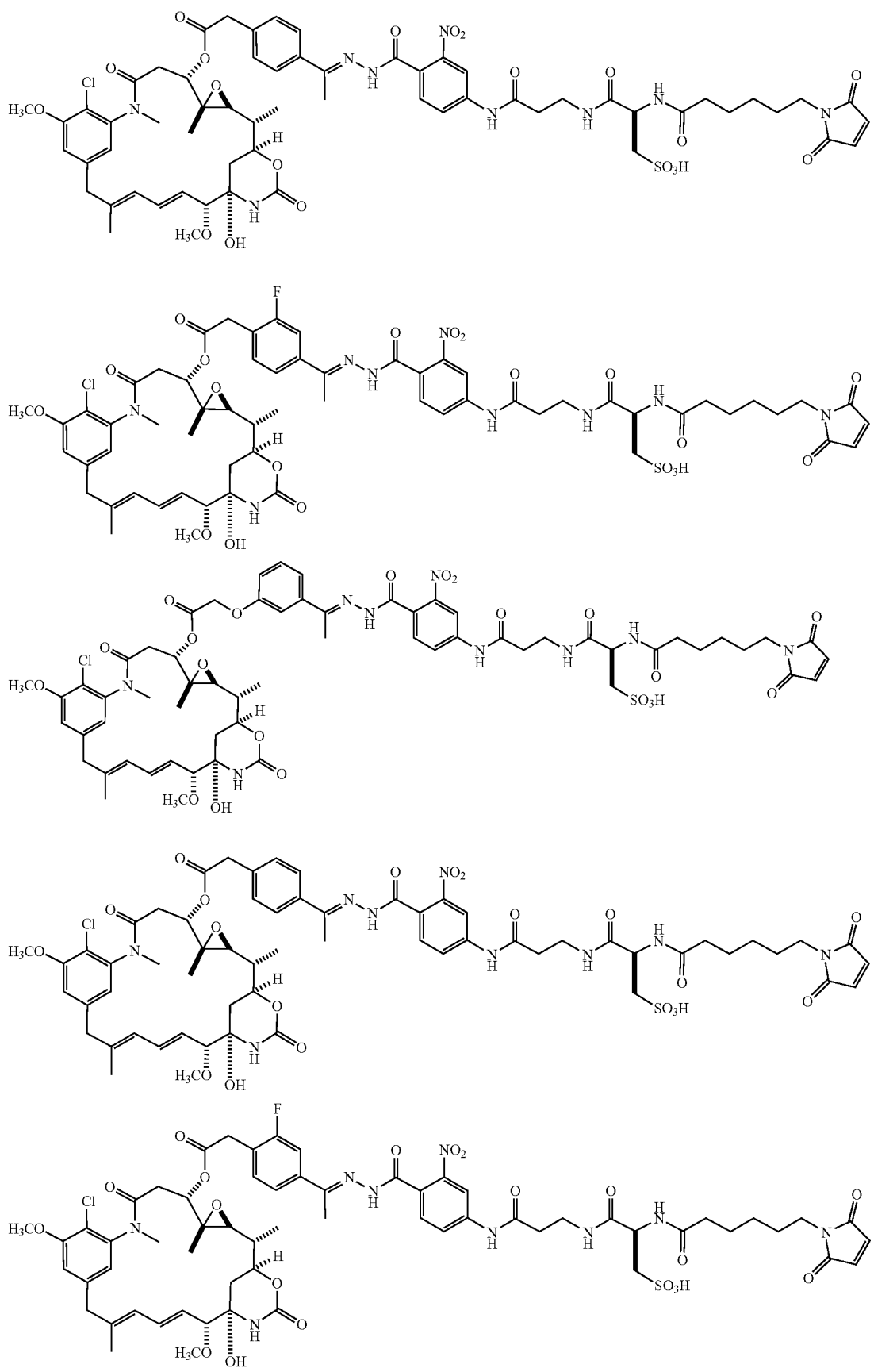

-continued

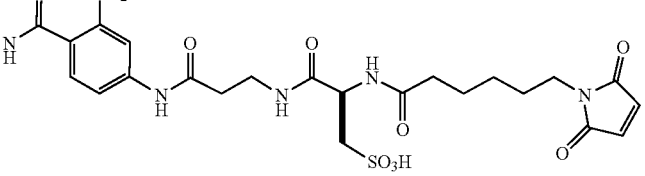
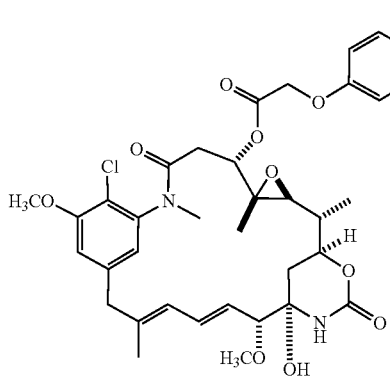

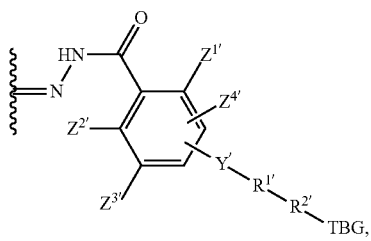
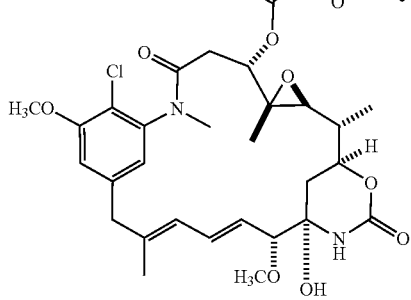

or a pharmaceutically acceptable salt, hydrate, solvate, or isomer thereof.

Pharmaceutical Compositions

In some embodiments, the disclosure provides a pharmaceutical composition comprising a compound described herein. In some embodiments, the composition includes a compound of Formula (I) where R' is:

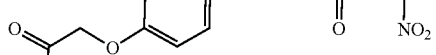

or the various embodiments disclosed herein.

The total amount of a compound in a composition to be administered to a patient is one that is suitable for that patient. One of skill in the art would appreciate that different individuals may require different total amounts of the therapeutically effective substance. In some embodiments, the amount of the compound is a pharmaceutically effective amount. The skilled worker would be able to determine the amount of the compound in a composition needed to treat a patient based on factors such as, for example, the age, weight, and physical condition of the patient. The concentration of the compound depends on its solubility in the intravenous administration solution and the volume of fluid that can be administered. For example, the concentration of the compound may be from about 0.1 mg/ml to about 50 mg/ml in the injectable composition. In some embodiments, the concentration of the compound may be in the range of about 0.1 mg/ml to about 40 mg/mL.

The pharmaceutical compositions and kits of the present disclosure may also contain diluents, fillers, salts, buffers, stabilizers, solubilizers, protectants and other materials well known in the art. The term "pharmaceutically acceptable" means a non-toxic material that does not interfere with the effectiveness of the biological activity of the active ingredient(s). The characteristics of the carrier will depend on the route of administration.

The compositions may be administered in a variety of conventional ways. Exemplary routes of administration that can be used include oral, parenteral, intravenous, intra-arterial, cutaneous, subcutaneous, intramuscular, topical, intracranial, intraorbital, ophthalmic, intravitreal, intraventricular, intracapsular, intraspinal, intracisternal, intraperitoneal, intranasal, aerosol, central nervous system (CNS) administration, or administration by suppository. In some embodiments, the compositions are suitable for parenteral administration. These compositions may be administered, for example, intraperitoneally, intravenously, or intrathecally. In some embodiments, the compositions are injected intravenously. In some embodiments, a reconstituted formulation can be prepared by reconstituting a lyophilized compound composition in a reconstitution liquid comprising e.g. an alcohol, DMSO, and/or polyethylene glycol and water and/or a salt buffer. Such reconstitution may comprise adding the reconstitution liquid and mixing, for example, by swirling or vortexing the mixture. The reconstituted formulation then can be made suitable for injection by mixing e.g., Lactated Ringer's solution, 5% Glucose solution, isotonic saline or a suitable salt buffer with the formulation to create an injectable composition. One of skill in the art would appreciate that a method of administering a therapeutically effective substance formulation or composition would depend on factors such as the age, weight, and physical condition of the patient being treated, and the disease or condition being treated. The skilled worker would, thus, be able to select a method of administration optimal for a patient on a case-by-case basis.

In some embodiments, the compounds and compositions disclosed herein are for use in treating a cancer, a virus disease, autoimmune disease, acute or chronic inflammatory disease, and a disease caused by bacteria, fungi, or other micro-organisms.

In some embodiments, the compound disclosed herein may be used in the manufacture of a medicament for treating a disease selected from a cancer, a virus disease, autoimmune disease, acute or chronic inflammatory disease, and a disease caused by bacteria, fungi, or other micro-organisms.

In some embodiments, the cancer is a blood cancer or a solid tumor cancer. In some embodiments, the cancer is selected from carcinoma, sarcoma, leukemia, lymphoma, multiple myeloma, and melanoma.

In some embodiments, the cancer is adenocarcinoma, uveal melanoma, acute leukemia, acoustic neuroma, ampullary carcinoma, anal carcinoma, astrocytoma's, basalioma, pancreatic cancer, connective tissue tumor, bladder cancer, bronchial carcinoma, non-small cell bronchial carcinoma, breast cancer, Burkitt's lymphoma, corpus carcinoma, CUP syndrome, colon cancer, cancer of the small intestine, ovarian cancer, endometrial carcinoma, gallbladder cancer, gallbladder carcinoma, uterine cancer, cervical cancer, neck, nose and ear tumors, hematological neoplasia's, hairy cell leukemia, urethral cancer, skin cancer, gliomas, testicular cancer, Kaposi's sarcoma, laryngeal cancer, bone cancer, colorectal carcinoma, head/neck tumors, colon carcinoma, craniopharyngeoma, liver cancer, leukemia, lung cancer, non-small cell lung cancer, Hodgkin's lymphoma, non-Hodgkin's lymphoma, stomach cancer, colon cancer, medulloblastoma, melanoma, meningioma, kidney cancer, renal cell carcinomas, oligodendroglioma, esophageal carcinoma, osteolytic carcinomas and osteoplastic carcinomas, osteosarcoma, ovarian carcinoma, pancreatic carcinoma, penile cancer, prostate cancer, tongue cancer, ovary carcinoma or lymph gland cancer.

In some embodiments, the present disclosure provides a kit comprising a compound as described herein and, a pharmaceutically acceptable excipient, a carrier, and/or a diluent.

In some embodiments, one or more excipients may be included in the composition. One of skill in the art would appreciate that the choice of any one excipient may influence the choice of any other excipient. For example, the choice of an excipient may preclude the use of one or more additional excipients because the combination of excipients would produce undesirable effects. One of skill in the art would empirically be able to determine which excipients, if any, to include in the compositions. Excipients may include, but are not limited to, co-solvents, solubilizing agents, buffers, pH adjusting agents, bulking agents, surfactants, encapsulating agents, tonicity-adjusting agents, stabilizing agents, protectants, and viscosity modifiers. In some embodiments, it may be beneficial to include a pharmaceutically acceptable carrier in the compositions.

In some embodiments, a solubilizing agent may be included in the compositions. Solubilizing agents may be useful for increasing the solubility of any of the components of the composition, including a compound or an excipient. The solubilizing agents described herein are not intended to constitute an exhaustive list, but are provided merely as exemplary solubilizing agents that may be used in the compositions. In certain embodiments, solubilizing agents include, but are not limited to, ethyl alcohol, tert-butyl alcohol, polyethylene glycol, glycerol, propylene glycol, methylparaben, propylparaben, polyethylene glycol, polyvinyl pyrrolidone, cyclodextrins such as dimethyl-β-cyclodextrin, hydroxyethyl-β-cyclodextrin, hydroxypropyl-β-cyclodextrin, and trimethyl-β-cyclodextrin, and combinations thereof, and any pharmaceutically acceptable salts and/or combinations thereof The pH of the compositions may be any pH that provides desirable properties for the formulation or composition. Desirable properties may include, for example, compound stability, increased compound retention as compared to compositions at other pH values, and improved filtration efficiency. In some embodiments, the pH value of the compositions may be from about 3.0 to about 9.0, e.g., from about 5.0 to about 7.0. In particular embodiments, the pH value of the compositions may be 5.5±0.1, 5.6±0.1, 5.7±0.1, 5.8±0.1, 5.9±0.1, 6.0±0.1, 6.1±0.1, 6.2±0.1, 6.3±0.1, 6.4±0.1, 6.5±0.1, 6.6±0.1, 6.7±0.1, 6.8±0.1, 6.9±0.1, 7.0±0.1, 7.1±0.1, and 7.2±0.1.

In some embodiments, it may be beneficial to buffer the pH by including one or more buffers in the compositions. In certain embodiments, a buffer may have a pKa of, for example, about 5.5, about 6.0, or about 6.5. One of skill in the art would appreciate that an appropriate buffer may be chosen for inclusion in compositions based on its pKa and other properties. Buffers are well known in the art. Accordingly, the buffers described herein are not intended to constitute an exhaustive list, but are provided merely as exemplary buffers that may be used in the formulations or compositions of the present disclosure. In certain embodiments, a buffer includes, but is not limited to Tris, Tris-HCl, potassium phosphate, sodium phosphate, sodium citrate, sodium ascorbate, combinations of sodium and potassium phosphate, Tris/Tris-HCl, sodium bicarbonate, arginine phosphate, arginine hydrochloride, histidine hydrochloride, cacodylate, succinate, 2-(N-morpholino)ethanesulfonic acid (MES), maleate, bis-tris, phosphate, carbonate, and any pharmaceutically acceptable salts and/or combinations thereof.

In some embodiments, a pH-adjusting agent may be included in the compositions. Modifying the pH of a composition may have beneficial effects on, for example, the stability or solubility of a compound, or may be useful in making a composition suitable for parenteral administration. pH-adjusting agents are well known in the art. Accordingly, the pH-adjusting agents described herein are not intended to constitute an exhaustive list, but are provided merely as exemplary pH-adjusting agents that may be used in the compositions. pH-adjusting agents may include, for example, acids and bases. In some embodiments, a pH-adjusting agent includes, but is not limited to, acetic acid, hydrochloric acid, phosphoric acid, sodium hydroxide, sodium carbonate, and combinations thereof.

In some embodiments, a bulking agent may be included in the compositions. Bulking agents are commonly used in lyophilized compositions to provide added volume to the composition and to aid visualization of the composition, especially in instances where the lyophilized pellet would otherwise be difficult to see. Bulking agents also may help prevent a blowout of the active component(s) of a pharmaceutical composition and/or to aid cryoprotection of the composition. Bulking agents are well known in the art. Accordingly, the bulking agents described herein are not intended to constitute an exhaustive list, but are provided merely as exemplary bulking agents that may be used in the compositions.

Exemplary bulking agents may include carbohydrates, monosaccharides, disaccharides, polysaccharides, sugar alcohols, amino acids, and sugar acids, and combinations thereof. Carbohydrate bulking agents include, but are not limited to, mono-, di-, or poly-carbohydrates, starches, aldoses, ketoses, amino sugars, glyceraldehyde, arabinose, lyxose, pentose, ribose, xylose, galactose, glucose, hexose, idose, mannose, talose, heptose, glucose, fructose, methyl α-D-glucopyranoside, maltose, lactone, sorbose, erythrose, threose, arabinose, allose, altrose, gulose, idose, talose, erythrulose, ribulose, xylulose, psicose, tagatose, glucosamine, galactosamine, arabinans, fructans, fucans, galactans, galacturonans, glucans, mannans, xylans, inulin, levan, fucoidan, carrageenan, galactocarolose, pectins, amylose, pullulan, glycogen, amylopectin, cellulose, pustulan, chitin, agarose, keratin, chondroitin, dermatan, hyaluronic acid, xanthin gum, sucrose, trehalose, dextran, and lactose. Sugar alcohol bulking agents include, but are not limited to, alditols, inositols, sorbitol, and mannitol. Sugar acid bulking agents include, but are not limited to, aldonic acids, uronic acids, aldaric acids, gluconic acid, isoascorbic acid, ascorbic acid, glucaric acid, glucuronic acid, gluconic acid, glucaric acid, galacturonic acid, mannuronic acid, neuraminic acid, pectic acids, and alginic acid. Amino acid bulking agents include, but are not limited to, glycine, histidine, and proline.

In some embodiments, a surfactant may be included in the compositions. Surfactants, in general, reduce the surface tension of a liquid composition. This may provide beneficial properties such as improved ease of filtration. Surfactants also may act as emulsifying agents and/or solubilizing agents. Surfactants are well known in the art. Accordingly, the surfactants described herein are not intended to constitute an exhaustive list, but are provided merely as exemplary surfactants that may be used in the formulations or compositions of the present disclosure. Surfactants that may be included include, but are not limited to, sorbitan esters such as polysorbates (e.g., polysorbate 20 and polysorbate 80), lipopolysaccharides, polyethylene glycols (e.g., PEG 400 and PEG 3000), poloxamers (i.e., pluronics), ethylene oxides and polyethylene oxides (e.g., Triton X-100), saponins, phospholipids (e.g., lecithin), and combinations thereof.

In some embodiments, an encapsulating agent may be included in the compositions. Encapsulating agents can sequester molecules and help stabilize or solubilize them. Encapsulating agents are well known in the art. Accordingly, the encapsulating agents described herein are not intended to constitute an exhaustive list, but are provided merely as exemplary encapsulating agents that may be used in the compositions. Encapsulating agents that may be included in compositions include, but are not limited to α-cyclodextrins, β-cyclodextrins, γ-cyclodextrin and combinations thereof (e.g., α-cyclodextrin, dimethyl-α-cyclodextrin, hydroxyethyl-α-cyclodextrin, hydroxypropyl-α-cyclodextrin, trimethyl-α-cyclodextrin, β-cyclodextrin, dimethyl-β-cyclodextrin, hydroxyethyl-β-cyclodextrin, hydroxypropyl-β-cyclodextrin, trimethyl-β-cyclodextrin, γ-cyclodextrin, dimethyl-γ-cyclodextrin, hydroxyethyl-γ-cyclodextrin, hydroxypropyl-γ-cyclodextrin, trimethyl-γ-cyclodextrin, and combinations thereof.

In some embodiments, a tonicity-adjusting agent may be included in the compositions. The tonicity of a liquid composition is an important consideration when administering the composition to a patient, for example, by parenteral administration. Tonicity-adjusting agents, thus, may be used to help make a composition suitable for administration. Tonicity-adjusting agents are well known in the art. Accordingly, the tonicity-adjusting agents described herein are not intended to constitute an exhaustive list, but are provided merely as exemplary tonicity-adjusting agents that may be used in the compositions. Tonicity-adjusting agents may be ionic or non-ionic and include, but are not limited to, inorganic salts, amino acids, carbohydrates, sugars, sugar alcohols, and carbohydrates. Exemplary inorganic salts may include sodium chloride, potassium chloride, sodium sulfate, and potassium sulfate. An exemplary amino acid is glycine. Exemplary sugars may include sugar alcohols such as glycerol, propylene glycol, glucose, sucrose, lactose, dextrose, and mannitol.

In some embodiments, a stabilizing agent may be included in the compositions. Stabilizing agents help increase the stability of a compound in the compositions. This may occur by, for example, reducing degradation or preventing aggregation of a compound. Without wishing to be bound by theory, mechanisms for enhancing stability may include sequestration of the compound from a solvent or inhibiting free radical oxidation of the therapeutically effective substance. Stabilizing agents are well known in the art. Accordingly, the stabilizing agents described herein are not intended to constitute an exhaustive list, but are provided merely as exemplary stabilizing agents that may be used in the compositions. Stabilizing agents may include, but are not limited to, emulsifiers and surfactants.

In some embodiments, a protectant may be included in the compositions. Protectants are agents that protect a pharmaceutically active ingredient (e.g., a therapeutically effective substance or compound) from an undesirable condition (e.g., instability caused by freezing or lyophilization, or oxidation). Protectants can include, for example, cryoprotectants, lyoprotectants, and antioxidants. Cryoprotectants are useful in preventing loss of potency of an active pharmaceutical ingredient (e.g., an anthracycline compound) when a composition is exposed to a temperature below its freezing point. For example, a cryoprotectant could be included in a reconstituted lyophilized formulation so that the formulation could be frozen before dilution for intravenous administration. Cryoprotectants are well known in the art. Accordingly, the cryoprotectants described herein are not intended to constitute an exhaustive list, but are provided merely as exemplary cryoprotectants that may be used in the compositions. Cryoprotectants include, but are not limited to, solvents, surfactants, encapsulating agents, stabilizing agents, viscosity modifiers, and combinations thereof. Cryoprotectants may include, for example, disaccharides (e.g., sucrose, lactose, maltose, and trehalose), polyols (e.g., glycerol, mannitol, sorbitol, and dulcitol), glycols (e.g., ethylene glycol, polyethylene glycol and propylene glycol).

Lyoprotectants are useful in stabilizing the components of a composition subjected to lyophilization. For example, a therapeutically effective substance could be lyophilized with a lyoprotectant prior to reconstitution. Lyoprotectants are well known in the art. Accordingly, the lyoprotectants described herein are not intended to constitute an exhaustive list, but are provided merely as exemplary lyoprotectants that may be used in the compositions. Lyoprotectants include, but are not limited to, solvents, surfactants, encapsulating agents, stabilizing agents, viscosity modifiers, and combinations thereof. Exemplary lyoprotectants may be, for example, sugars and polyols. Trehalose, sucrose, dextran, and hydroxypropyl-beta-cyclodextrin are non-limiting examples of lyoprotectants.

Antioxidants are useful in preventing oxidation of the components of a composition. Oxidation may result in aggregation of a drug product or other detrimental effects to the purity of the drug product or its potency. Antioxidants are well known in the art. Accordingly, the antioxidants described herein are not intended to constitute an exhaustive list, but are provided merely as exemplary antioxidants that may be used in the compositions. Antioxidants may be, for example, sodium ascorbate, citrate, thiols, metabisulfite, and combinations thereof.

In some embodiments, a viscosity-modifying agent may be included in the composition. Viscosity modifiers change the viscosity of liquid compositions. This may be beneficial because viscosity plays an important role in the ease with which a liquid composition is filtered. A composition may be filtered prior to lyophilization and reconstitution, or after reconstitution. Viscosity modifiers are well known in the art. Accordingly, the viscosity modifiers described herein are not intended to constitute an exhaustive list, but are provided merely as exemplary viscosity modifiers that may be used in the compositions. Viscosity modifiers include solvents, solubilizing agents, surfactants, and encapsulating agents. Exemplary viscosity modifiers that may be included in compositions include, but are not limited to, N-acetyl-DL-tryptophan and N-acetyl-cysteine.

Antitumor Activity in Human Tumor Xenograft Mice Models

The albumin-binding maytansinoids 30 and 31 demonstrated exceptional antitumor activity in five human tumor xenograft models in nude mice inducing partial and complete tumor regressions in all human tumor xenograft evaluated (see FIGS. 3-16). This included starting tumor volumes in the range of approximately 80-110 mm$^3$ but also initial starting tumor volumes of up to approximately 400 mm$^3$. Furthermore, in most cases therapy with albumin-binding maytansinoids 30 and 31 induced long-term remissions and a decrease in Relative Tumor Volume (RTV). The parent compound maytansine was principally inactive in the tested models or only showed marginal tumor inhibition. Experimental procedure and the results in the tumor-bearing mice models are described in detail in Examples 11-19 and FIGS. 3-16.

Methods of Treatment

The compounds and compositions described herein are useful for a variety of clinical applications. In embodiments, the methods of treatment utilize a compound of composition that includes a compound of Formula (I) where R' is:

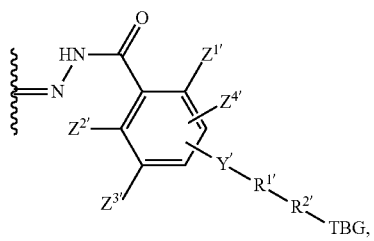

or the various embodiments disclosed herein.

The compounds and compositions described herein can induce prolonged or long-term inhibition of tumor growth.

In certain embodiments, the prolonged or long-term inhibition of tumor growth is without any loss in body weight or any or merely marginal bone marrow toxicity.

In some embodiments, the present disclosure provides a method for treating a malignant disease comprising administering to a patient in need thereof a therapeutically effective amount of a pharmaceutical composition containing a compound described herein. For example, some embodiments include a method for treating a patient suffering from a disease or condition selected from a cancer, a virus disease, autoimmune disease, acute or chronic inflammatory disease, and a disease caused by bacteria, fungi, and other micro-organisms, comprising administering to the patient in need thereof a therapeutically effective amount of a compound according to the present disclosure.

The disclosure provides for methods of treating a condition or disease in a patient, said condition or disease selected from a cancer, a virus disease, autoimmune disease, acute or chronic inflammatory disease, and a disease caused by bacteria, fungi, or other micro-organisms, comprising administering to the patient a compound or a pharmaceutical composition as described herein.

In some embodiments, the cancer comprises a vascularized tumor. In some embodiments, the cancer is a blood cancer or a solid tumor cancer. In some embodiments, the cancer is selected from carcinoma, sarcoma, leukemia, lymphoma, multiple myeloma, and melanoma.

In some embodiments, the cancer is selected from adenocarcinoma, uveal melanoma, acute leukemia, acoustic neuroma, ampullary carcinoma, anal carcinoma, astrocytoma, basalioma, pancreatic cancer, connective tissue tumor, bladder cancer, bronchial carcinoma, non-small cell bronchial carcinoma, breast cancer, Burkitt's lymphoma, corpus carcinoma, CUP syndrome, colon cancer, cancer of the small intestine, ovarian cancer, endometrial carcinoma, gallbladder cancer, uterine cancer, cervical cancer, neck, nose and ear tumors, hematological neoplasia, hairy cell leukemia, urethral cancer, skin cancer, gliomas, testicular cancer, Kaposi's sarcoma, laryngeal cancer, bone cancer, colorectal carcinoma, head/neck tumors, colon carcinoma, craniopharyngeoma, liver cancer, leukemia, lung cancer, non-small cell lung cancer, Hodgkin's lymphoma, non-Hodgkin's lymphoma, stomach cancer, colon cancer, medulloblastoma, melanoma, meningioma, kidney cancer, renal cell carcinomas, oligodendroglioma, esophageal carcinoma, osteolytic carcinomas and osteoplastic carcinomas, osteosarcoma, ovarian carcinoma, pancreatic carcinoma, penile cancer, prostate cancer, tongue cancer, ovary carcinoma, and lymph gland cancer.

Some embodiments include a method of increasing the concentration of a metabolite of a compound in a tumor, comprising administering the compound according to the present disclosure. In embodiments the compound is a compound of Formula (I) where R' is:

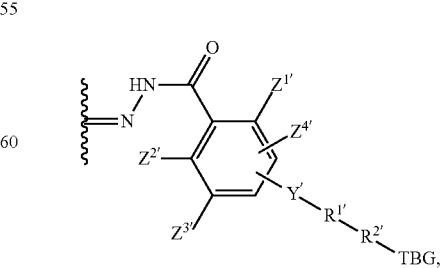

or the various embodiments disclosed herein. In some embodiments, the increase is compared to an equivalent dose of the unmodified active agent, e.g., the "unmodified active agent" may be the same compound of Formula (I) where R' is O.

Some embodiments include a method of reducing cytotoxicity of a compound comprising administering a compound or a pharmaceutical composition of the disclosure to a patient in need thereof, wherein the administration results in a reduction in cytotoxicity when compared to an equivalent dose of the unmodified active agent. For example, in some embodiments, the method of reducing cytotoxicity comprises administering a compound of Formula (I) where R' is:

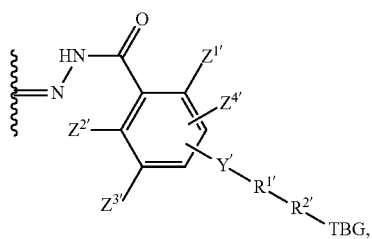

or the various embodiments disclosed herein, and the "unmodified active agent" is the same compound of Formula (I) where R' is O.

Exemplification

With aspects of the present disclosure now being generally described, these will be more readily understood by reference to the following examples, which are included merely for purposes of illustration of certain features and embodiments of the present disclosure and are not intended to be limiting.

Equivalents

Those skilled in the art will recognize or be able to ascertain using no more than routine experimentation, numerous equivalents to the compounds, compositions, and methods of use thereof described herein. Such equivalents are considered to be within the scope of the present disclosure.

EXAMPLES

The following examples demonstrate the various embodiments and the aspects of the invention.

Abbreviations

The following is a list of abbreviations used in the Examples, with their full chemical names. If not defined, the terms have their generally accepted meanings.
aq.=aqueous
Boc=N-tert-butoxycarbonyl
calcd.=calculated
DCM=dichloromethane
DIC=N,N'-diisopropylcarbodiimide
DMAP=N,N-dimethyl-4-aminopyridine
DMF=N,N-dimethylformamide
DMSO=dimethylsulfoxide
CV=column volume
EDC=1-ethyl-3-(3-dimethylaminopropyl)carbodiimide
eq=equivalents
ESI=electrospray ionization
Fmoc=fluorenylmethyloxycarbonyl
HATU=(1-[bis(dimethylamino)methylene]-1H-1,2,3-triazolo[4,5-b]pyridinium 3-oxid hexafluorophosphate)
HOAt=1-hydroxy-7-azabenzotriazole
HOBt=N-hydroxybenzotriazole
HPLC=high-performance liquid chromatography
HRMS=high resolution mass spectrometry
HSA=human serum albumin
IC=ion chromatography
LC-MS=liquid chromatography mass spectroscopy
LRMS=low resolution mass spectrometry
MeCN=acetonitrile
MeOH=methanol
NMR=nuclear magnetic resonance spectroscopy
NP=normal phase
Np=4-nitrophenoxycarbonyl
nd=not detectable
na=not available
PBS=phosphate buffered saline, pH 7
RP=reverse phase
TFA=trifluoroacetic acid
TRIS=2-amino-2-(hydroxymethyl)-1,3-propanediol Example 1

Preparation of Linker 1

Linker 1 may be prepared as described below and shown in Scheme 1.

Scheme 1

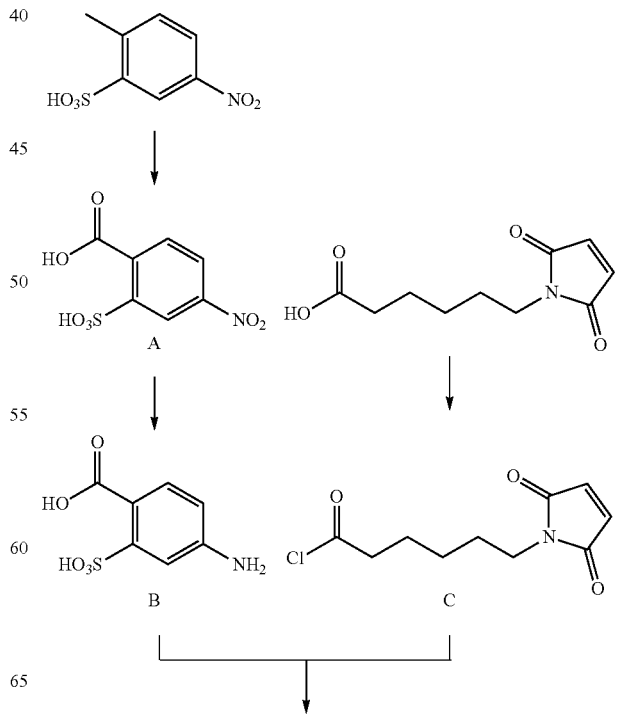

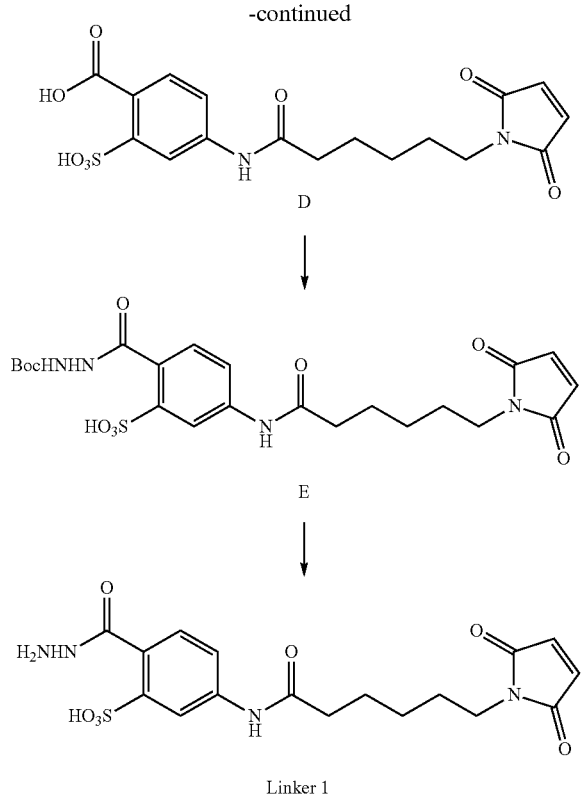

Linker 1

Synthesis of 4-nitro-2-sulfobenzoic Acid (A)

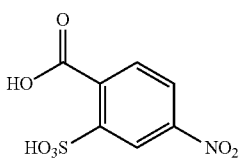

To a stirred solution of potassium permanganate (72 g, 460 mmol, 4.5 eq) in water (450 mL) was added within 10 s a solution of 4-nitro-2-sulfonic acid hydrate (26 g, 102 mmol, 1.0 eq) in Millipore water (100 mL). The resulting purple mixture was stirred at 115° C. for 5 h and turned brown after this time. HPLC analysis (PDA 220 nm) confirmed that the reaction was finished after 5 h (>90% conversion). The reaction mixture was cooled down to room temperature. The brown solid formed during the reaction was removed through suction filtration on a Celite pad, washed with Millipore water (300 mL) and the brown/yellow filtrate solution was concentrated to ca. 125 mL, with a rotary evaporator at 40° C., acidified slowly with a 5 M HCl (ca. 2 mL) solution until a white suspension was formed (ca. pH 1.0). The white suspension was then heated at 100° C. until a clear solution was obtained which was left to stand in an ice bath for 10 min, until a white solid formed. The white solid was obtained by suction filtration using a fritted filter. The white solid was then dried under high vacuum to give 4-nitro-2-sulfobenzoic acid. Yield: 18 g (72%). Purity by RP-HPLC, 220 nm, >95%. LRMS-ESI (m/z) calcd. for $C_7H_4NO_7S$ [M–H]$^-$: 245.98. Found: 245.83.

Synthesis of 4-amino-2-sulfobenzoic Acid (B)

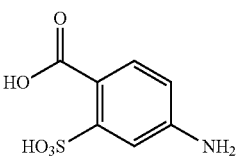 [SMILES: Nc1ccc(C(=O)O)c(S(=O)(=O)O)c1]

A stirred suspension of 4-nitro-2-sulfobenzoic acid (13 g, 51 mmol, 1.0 eq) in water (75 mL) was heated at reflux until complete dissolution of the 4-nitro-2-sulfobenzoic acid. At that temperature was then added acetic acid (7.2 mL) followed by iron powder (9.5 g, 180 mmol, 3.5 eq) that was added portion wise (~1 g/min) over 10 min to avoid exothermic reaction. The reaction mixture was then left stirring under reflux for 1 h. During this time, a brown solid formed and HPLC analysis (PDA 220 nm) confirmed that the reaction was finished (>95% conversion). The brown solid was removed by suction filtration directly on a Celite pad (when still hot) and was further washed with hot water. The filtrate was re-filtered. The resulting filtrate was concentrated with a rotary evaporator at 40° C. to a final volume of 100 mL. Concentrated HCl was added dropwise until pH 1 was reached, and a white/yellow solid precipitated. The suspension was left at 4° C. for 1 h. The solid was collected by suction filtration using a fritted filter and was dried under high vacuum to afford 4-amino-2-sulfobenzoic acid as a white solid. Yield: 9 g (81%). Purity by RP-HPLC, 220 nm, >95%. LRMS-ESI (m/z) calcd. for $C_7H_4NO_5S$ [M–H]$^-$: 216.00. Found: 216.16.

Synthesis of 6-maleimidohexanoyl Chloride or EMC-Cl (C)

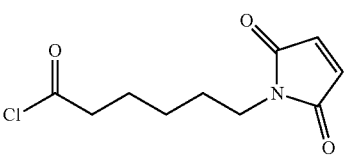 [SMILES: O=C(Cl)CCCCCN1C(=O)C=CC1=O]

To a stirring yellow solution of 6-maleimido caproic acid (EMC) (33 g, 156 mmol, 1.0 eq) in dry DCM (150 mL) at room temperature and under $N_2$ atmosphere, was added within 30 min (~0.5 mL/min) oxalyl chloride (15 mL, 171 mmol, 1.1 eq) using a dropping funnel. The reaction was stirred at room temperature for 5 h. The color of the reaction solution changed to dark yellow during the reaction time and HPLC analysis (PDA 220 nm) confirmed that the reaction was finished after 5 h (>95% conversion). Solvent was removed with a rotary evaporator at 40° C. to obtain an oil. This residual oil was dried under high vacuum overnight (solidified overnight). The obtained light brownish solid was crushed and dried for further 20 h under high vacuum to give 6-maleimidohexanoyl chloride as a yellow microcrystalline solid. The compound was used in the next reaction without further purification. Yield: 34 g (95%). Purity by RP-HPLC, 220 nm, >95% as the methyl ester. LRMS-ESI (m/z) calcd. for $C_{11}H_{16}NO_4$ (as methyl ester) [M+H]$^+$: 226.10. Found: 225.97.

Synthesis of 4-(6-maleimidohexanamido)-2-sulfobenzoic Acid (D)

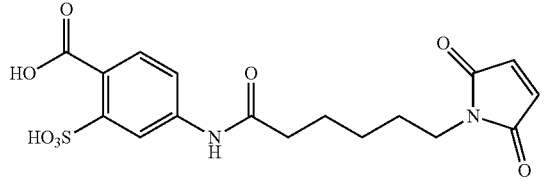 [SMILES: O=C(CCCCCN1C(=O)C=CC1=O)Nc1ccc(C(=O)O)c(S(=O)(=O)O)c1]

4-Amino-2-sulfobenzoic acid (18.5 g, 85.0 mmol, 1.0 eq) was dissolved in anhydrous DMF (300 mL) under $N_2$ atmosphere. The solution was cooled down to 4° C., and left stirring for 10 min. Then, 4-N-methylmorpholine (18.7 mL, 170 mmol, 2.0 eq) was added dropwise (~0.3 mL/min), within 1 h using a dropping funnel to the cooled solution. To this dark brown mixture was added dropwise (~0.5 g/min), within 1 h using a dropping funnel, a solution of EMC-Cl (29.3 g, 127 mmol, 1.5 eq) in anhydrous DMF (200 mL). The reaction mixture was stirred overnight and then allowed to reach room temperature over 10 h. After completion of the reaction as indicated by HPLC analysis (PDA 220 nm, >95% conversion), the reaction solution was dispensed in 8×50 mL falcon tubes.

The samples were centrifuged for 20 minutes at 10° C. and 4.000 rpm. The supernatants were removed by decantation, and the solids were re-suspended in 10 mL of DMF per each tube and centrifuged again for 20 min at 10° C. and 4.000 rpm. All the DMF supernatants were combined and concentrated under reduced pressure at 50° C. for 3 h to obtain a light orange solid. The solid was re-suspended in methanol (250 mL) and transferred to 8×50 mL falcon tubes. The samples were centrifuged for 20 minutes at 10° C. and 4.000 rpm. The supernatants were removed by decantation, and the solids were re-suspended in 5 mL of methanol per each tube and centrifuged again for 20 min at 10° C. and 4.000 rpm. All the solids were combined and dried under high vacuum for 24 h to obtain a crystalline yellow solid. Yield: 17 g (48%). Purity by RP-HPLC reverse phase, 220 nm, 80%. LRMS-ESI (m/z) calcd. for $C_{17}H_{17}N_2O_8S$ [M−H]⁻: 409.08. Found: 409.13.

Synthesis of 2-(2-(tert-butoxycarbonyl)hydrazine-1-carbonyl)-5-(6-maleimidohexanamido)benzenesulfonic Acid or Boc-Protected Linker 1 (E)

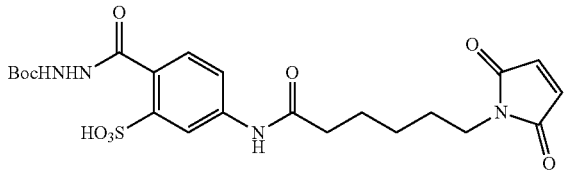

To a solution of 4-(6-maleimidohexanamido)-2-sulfobenzoic acid (17.0 g, 41.4 mmol, 1.0 eq) in anhydrous DMF (350 mL) under $N_2$ atmosphere were added EDC-HCl (8.72 g, 45.5 mmol, 1.1 eq) and 1HOBt (6.15 g, 45.5 mmol, 1.1 eq). The reaction mixture was left to stir 30 min at room temperature, and then tert-butyl-carbazate (7.12 g, 53.9 mmol, 1.3 eq) was added and the solution turns from clear yellow to reddish. The reaction mixture was stirred at room temperature overnight. After this time, completion of the reaction was confirmed by HPLC (PDA 220 nm, >95% conversion). The solvent was removed with a rotary evaporator at 40° C. and under high vacuum for 1 h, to afford purple-brown oil, which was purified with a Biotage Isolera One flash purification System, with two pre-packed SNAP ULTRA 340 g cartridge, with Biotage® HP-Sphere™ spherical silica. The tubes containing the desired product were combined and dried with a rotary evaporator and under high vacuum for 10 h to obtain 2-(2-(tert-butoxycarbonyl)hydrazine-1-carbonyl)-5-(6-maleimidohexanamido)benzenesulfonic acid as a foamy yellow solid. Yield: 9 g (42%). RP-HPLC (220 nm)>95%. LRMS-ESI (m/z) calcd. for $C_{22}H_{27}N_4O_9S$ [M−H]⁻: 523.16. Found: 523.15.

Synthesis of Linker 1

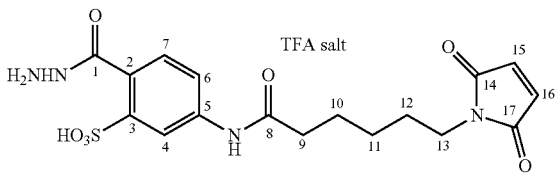

To a cooled (4-5° C.) solution of Boc-protected Linker 1 (10.2 g, 19.4 mmol, 1.0 eq) in anhydrous DCM (30 mL) was added dropwise (~0.5 mL/min) TFA (15 mL) within 30 min. After the addition, the cold bath was removed, and the reaction mixture was left to stir at room temperature for 3 h. After this time, completion of the reaction was confirmed by HPLC analysis (PDA 220 nm). The reaction mixture was poured dropwise in six falcon tubes, each of them with ca. 35 mL cold diethyl ether. A white precipitate formed immediately. The tubes were left at 4° C. for 3 h. After centrifugation of the falcon tubes (4000 rpm, 20 min, 10° C.), the supernatants were removed by decantation and the solids were re-suspended in 5 mL of diethyl ether per each tube and centrifuged again (4000 rpm, 20 min, 10° C.). The supernatants were removed again by decantation and the solids collected and dried under high vacuum to afford the Linker 1 as white microcrystalline solid as a TFA salt. Yield: 10 g (96%). RP-HPLC (220 nm)>95%. LRMS-ESI (m/z) calcd. for $C_{17}H_{21}N_4O_7S$ [M+H]⁺: 425.11. Found: 425.07. LRMS-ESI (m/z) calcd. for $C_{17}H_{19}N_4O_7S$ [M−H]⁻: 423.11. Found: 423.12. HRMS-ESI (m/z) calcd. for $C_{17}H_{21}N_4O_7S$ [M+H]⁺: 425.1125. Found: 425.1125. HRMS-ESI (m/z) calcd. for $C_{17}H_{19}N_4O_7S$ [M−H]⁻: 423.0978. Found: 423.0980.

The structure was confirmed by ¹H NMR and ¹³C NMR: ¹H NMR (400 MHz, DMSO-d₆) δ 11.94 (s, 1H; C1-NH), 10.27 (s, 1H; C8-NH), 8.01 (d, J=2.2 Hz, 1H; C4-CH), 7.93 (dd, J=8.5, 2.2 Hz, 1H; C6-CH), 7.68 (d, J=8.4 Hz, 1H; C7-CH), 7.00 (s, 2H; C15-CH, C16-CH), 3.40 (t, J=7.0 Hz, 2H; C13-CH₂), 2.32 (t, J=7.4 Hz, 2H; C9-CH₂), 1.60 (p, J=7.5 Hz, 2H; C10-CH₂), 1.52 (p, J=7.2 Hz, 2H; C12-CH₂), 1.26 (q, J=8.8 Hz, 2H; C11-CH₂); ¹³C NMR (101 MHz, DMSO-d₆) δ 172.20 (C8), 171.54 (C14, C17), 167.59 (C1), 145.73 (C5), 142.09 (C3), 134.90 (C15, C16), 132.09 (C7), 123.79 (C2), 119.44 (C6), 117.47 (C4), 37.42 (C13), 36.65 (C9), 28.22 (C12), 26.21 (C11), 24.90 (C10). Anal. calcd. for $C_{17}H_{21}N_4O_7S\cdot\frac{1}{2}$TFA C, 45.71; H, 4.26; N, 11.85; S, 6.78. Found: C, 46.2917; H, 4.4836; N, 12.8879; S, 6.7886. TFA content 0.51%.

Linker 1 may also be prepared as described below and shown in Scheme 2.

Scheme 2

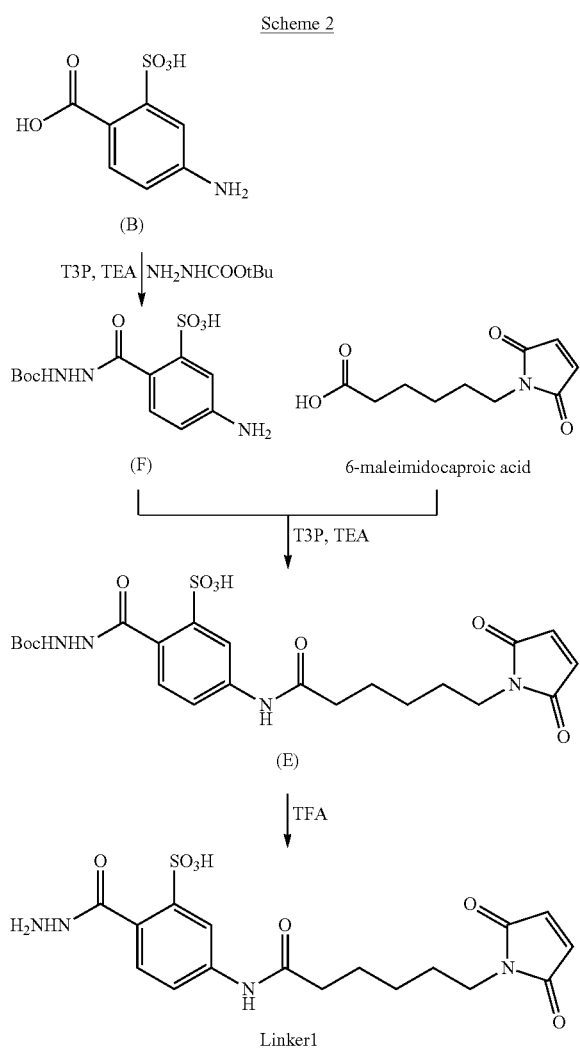

Synthesis of 5-amino-2-(2-(tert-butoxycarbonyl)hydrazine-1-carbonyl)benzenesulfonic Acid (F)

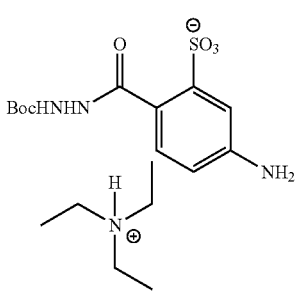

To a suspension of B (30.00 g, 138.12 mmol, 1.00 equiv.) in anhydrous acetonitrile (600 mL) was added triethylamine (41.93 g, 57.76 mL, 414.37 mmol, 3.00 equiv.) and the mixture was stirred for 10 min. Afterwards, tert-butyl carbazate (27.38 g, 207.19 mmol, 1.50 equiv.) was added and the mixture was cooled to −35° C. At this temperature, propylphosphonic anhydride solution, T3P, (114.27 g, 106.79 mL, 179.56 mmol, 50% sol. in ethyl acetate, 1.3 equiv.) was added dropwise over 1 h. The reaction was stirred at −35° C. for 2 h. The mixture was allowed to warm up to room temperature and filtered through Celite® 545 (100 g). Celite® was additionally washed with acetonitrile (500 mL). Both filtrates were combined and concentrated to 250 mL. The solution was split equally into 6 portions and the solvent was removed under reduced pressure. Each portion was dissolved in dichloromethane containing 1% $Et_3N$ (50 mL) and purified by NP flash chromatography on a Biotage Isolera™ One Flash Purification System, with a pre-packed SNAP Ultra 340 g column, using a step gradient from 2% to 12% methanol (containing 1% $NEt_3$) in DCM (containing 1% $NEt_3$) over 7 column volumes. Then, the purified fractions from all portions were combined, the solvent was removed under reduced pressure and the solid was dried under high vacuum to give title compound F as an off-white solid. Yield: 53.25 g, 108.0 mmol, 78.2% (NMR in DMSO-d6 showed the presence of 1.6 eq. triethylamine). HPLC (method 9, 220 nm)>99%. LRMS-ESI (m/z) calcd. for $C_{12}H_{16}N_3O_6S$ [M−H]$^-$: 330.08. Found: 330.08.

Synthesis of N-ethyl-N-isopropylpropan-2-aminium 2-(2-(tert-butoxy-carbonyl)hydrazine-1-carbonyl)-5-(6-(2,5-dioxo-2,5-dihydro-1H-pyrrol-1-yl)hexanamido)benzenesulfonate (E)

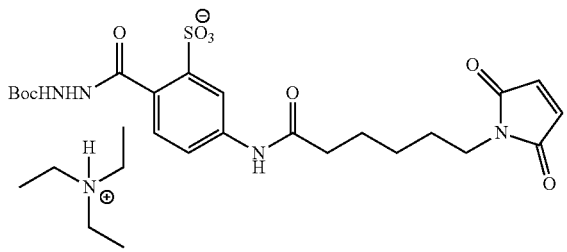

To a mixture of F (45.00 g, 91.24 mmol, 1.00 equiv.) and 6-maleimidocaproic acid (19.27 g, 91.24 mmol, 1.00 equiv.) was added, acetonitrile (450 mL), triethylamine (13.85 g, 19.08 mL, 136.86 mmol) and T3P (43.55 g, 40.70 mL, 136.86 mmol, 50% sol. in ethyl acetate) were added in one portion at room temperature. The solution was stirred at room temperature for 24 h. The solvent was removed under reduced pressure. The crude was then purified by flash purification system using seven pre-packed SNAP Ultra 340 g cartridge running a linear gradient from 2% methanol to 15% methanol in dichloromethane to give the title compound E as an off-white solid. Yield: 30.55 g, 53.5% (NMR in DMSO-d6 showed the presence of 1.1 eq. triethylamine). HPLC (method 9, 220 nm)>99%. LRMS-ESI (m/z) calcd. for $C_{22}H_{27}N_4O_9S$ [M−H]$^-$: 523.15. Found: 523.26.

Synthesis of 5-(6-(2,5-dioxo-2,5-dihydro-1H-pyrrol-1-yl)hexanamido)-2-(hydrazine-carbonyl)benzenesulfonic Acid (Linker 1)

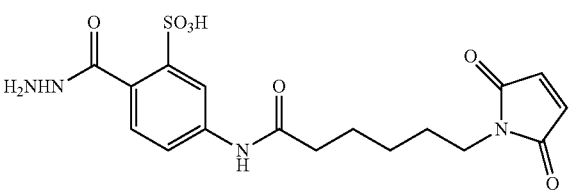

To a cold suspension (4° C.) of E, (10.00 g, 15.98 mmol, 1.00 equiv.) in dichloromethane (50 mL) was added trifluoroacetic acid (18.22 g, 12.31 mL, 159.81 mmol, 10.17 equiv.) over 15 min. The mixture was further stirred at 4° C. for 15 minutes, and then allowed to warm gradually to room temperature and stirred for 150 min. The reaction mixture was added dropwise via a separating funnel to a stirred solution of methyl tert-butyl ether, MTBE, (400 mL) and dichloromethane (200 mL). The resulted white solid was filtered through a 4 Å porosity fritted funnel and washed sequentially with dichloromethane (2×150 mL) and MTBE (1×50 mL), MeOH (1×50 mL) and again MTBE (2×150 mL). The solid was left to dry on the fitted funnel overnight at room temperature for 10 min. Further drying was carried out on high vacuum at 25° C. for 18 h. The final product Linker 1 was obtained as a yellow solid. Yield: 5.786 g, 13.63 mmol, 98.7%, HPLC (method 9, 220 nm)>96%. LRMS-ESI (m/z) calcd. for $C_{17}H_{19}N_4O_7S$ [M–H]⁻: 423.10. Found: 422.95.

Example 2

Preparation of Keto-Maytansinoids by Direct Esterification of Maytansinol with a Keto Acid General Method A:

Maytansinol (500 mg, 0.88 mmol, 1 eq) and the respective keto acid (3.52 mmol, 4 eq) were dissolved in anhydrous DCM (40 mL) in the presence of activated molecular sieves and cooled down to 4-5° C. using an ice bath. To this solution was then added within 10 s a solution of zinc(II) chloride in diethyl ether (2.64 mL, 2.64 mmol, 3.0 eq, 1 M solution). The resulting solution was stirred for 40 min at 4-5° C. followed by the addition of N,N'-diisopropylcarbodiimide (0.55 mL, 3.52 mmol, 4 eq). The mixture was stirred at 4° C. and then allowed to reach room temperature slowly overnight, immersed in an ice-bath. Conversion was monitored by LC-MS, and after reaching 60%, the reaction mixture was concentrated under reduced pressure at 40° C. to half of the volume, filtered through a 0.45 μm syringe filter (Macherey-Nagel, Chromafil® PTFE-O-45/25), and the filtrate was evaporated. The final product was purified with a Biotage Isolera One flash purification System, with a pre-packed SNAP ULTRA 50 g cartridge, with Biotage® HP-Sphere™ spherical silica (linear gradient from 100% DCM to 90/10 DCM/methanol in 25 CV). The tubes containing the product were combined and dried for 1 h with a rotary evaporator, and under high vacuum to afford the respective keto maytansinoid.

General Method B:

Maytansinol (758 mg, 1.34 mmol, 1.0 eq), the respective keto acid (1.47 mmol, 1.1 eq), and DMAP (181 mg, 1.47 mmol, 1.1 eq) were dissolved under $N_2$ atmosphere in anhydrous DCM (30 mL) in the presence of activated molecular sieves (0.8 g, 4 Å, 325 mesh particle size, Sigma Aldrich). The mixture was cooled down within 10 min to 4° C. using an ice/water bath. A solution of EDC-HCl (283 mg, 1.47 mmol, 1.1 eq) in dry DCM (15 mL) was added within 30 min (~10 mg/min) to the cooled mixture and the reaction mixture was stirred at 4° C. for 2 h. After this time, another portion of the keto acid (1.47 mmol, 1.1 eq) was added, followed by the addition of a solution of EDC-HCl (283 mg, 1.47 mmol, 1.1 eq) in dry DCM (10 mL) within 30 min (~10 mg/min) to the cooled mixture and the reaction mixture was stirred under inert atmosphere at 4° C. for 2 h. After this time, the addition of reagents was repeated once more, and the reaction mixture was left stirring overnight at 4° C. and then allowed to reach room temperature gradually during this time. The mixture was filtered (Macherey-Nagel, Chromafil® PTFE-O-45/25), and the solvent was removed with a rotary evaporator at 40° C. to a final volume of approximately 10 mL. The crude was purified with a Biotage Isolera One flash purification System, with a pre-packed SNAP ULTRA 100 g cartridge, with Biotage® HP-Sphere™ spherical silica (linear gradient from 100% DCM to 90/10 DCM/methanol in 25 CV). The tubes containing the product were combined and the solvent was removed with a rotary evaporator to obtain a solid. The solid was dried under high vacuum to afford the respective keto maytansinoid.

Preparation of Maytansinoid 2

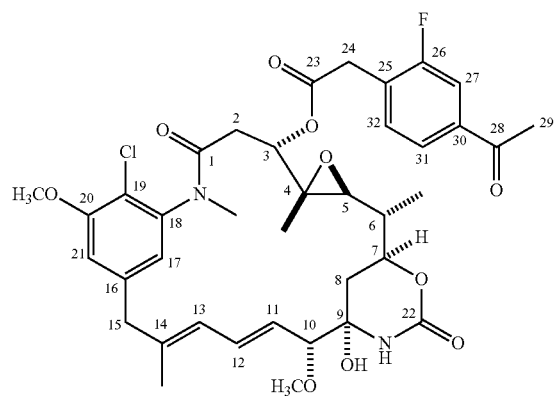 [SMILES: COc1cc2cc(c1Cl)N(C)C(=O)C[C@H](OC(=O)Cc1ccc(C(C)=O)cc1F)[C@]1(C)O[C@H]1[C@H](C)[C@@H]1C[C@@](O)(NC(=O)O1)[C@H](OC)/C=C/C=C(\C)C2]

From the reaction of maytansinol with 2-(4-acetyl-2-fluorophenyl)acetic acid using Method A: Maytansinoid 2 was obtained as a yellowish solid. Yield: 47%. Purity by RP-HPLC, 220 nm, 96%. LRMS-ESI (m/z) calcd. for: $C_{38}H_{45}ClFN_2O_{10}$ [M+H]⁺: 743.22. Found: 743.25. LRMS-ESI (m/z) calcd. for: $C_{38}H_{43}ClFN_2O_{10}$ [M–H]⁻: 741.22. Found: 741.41.

The structure was confirmed by $^1$H NMR and $^{13}$C NMR: $^1$H NMR (400 MHz, CDCl$_3$) δ 7.73 (dd, J=7.9, 1.6 Hz, 1H; C31-CH), 7.66 (dd, J=10.5, 1.6 Hz, 1H; C27-CH), 7.46 (t, J=7.6 Hz, 1H; C32-CH), 6.82 (d, J=1.8 Hz, 1H; C17-CH), 6.59 (d, J=1.8 Hz, 1H; C21-CH), 6.48 (dd, J=15.5, 11.0 Hz, 1H; C12-CH), 6.43 (s, 1H; C9-NH), 6.25 (d, J=10.9 Hz, 1H; C13-CH), 5.63 (dd, J=15.4, 8.8 Hz, 1H; C11-CH), 4.99 (dd, J=11.8, 2.7 Hz, 1H; C3-CH), 4.27 (td, J=11.2, 10.4, 1.8 Hz, 1H; C7-CH), 3.97 (s, 3H; C20-OCH$_3$), 3.90 (d, J=15.7 Hz, 1H; C24-CH$_2$), 3.76 (d, J=15.5 Hz, 1H; C24-CH$_2$), 3.54 (d, J=8.8 Hz, 1H; C10-CH), 3.46 (d, J=12.8 Hz, 1H; C15-CH$_2$), 3.38 (s, 3H; C10-OCH$_3$), 3.19 (d, J=12.8 Hz, 1H; C15-CH$_2$), 3.00 (s, 3H; C1-NCH$_3$), 2.87 (d, J=9.7 Hz, 1H; C5-CH), 2.57 (s, 3H; C29-CH$_3$), 2.51 (dd, J=14.1, 11.9 Hz, 1H; C2-CH$_2$), 2.17 (dd, J=13.9, 2.6 Hz, 1H; C2-CH$_2$), 1.72 (d, J=13.6 Hz, 1H; C8-CH$_2$), 1.68 (s, 3H; C14-CH$_3$), 1.50 (m, 1H; C6-CH), 1.28 (d, J=6.3 Hz, 4H; C6-CH$_3$, C8-CH$_2$), 0.87 (d, J=1.4 Hz, 3H; C4-CH$_3$); $^{13}$C NMR (101 MHz, CDCl$_3$) δ 196.50 (C28), 168.86 (C23), 168.30 (C1), 160.78 (d, $^1J_{C-F}$=247.0 Hz; C26), 156.13 (C20), 152.46 (C22), 142.53 (C18), 140.30 (C19), 140.24 (C14), 138.49 (d, $^3J_{C-F}$=6.4 Hz; C30), 132.58 (C12), 131.68 (d, $^3J_{C-F}$=3.6 Hz; C32), 128.32 (C11), 126.38 (d, $^2J_{C-F}$=16.1 Hz; C25), 124.82 (d, $^4J_{C-F}$=3.3 Hz; C31), 124.56 (C13), 122.04 (C21), 119.52 (C16), 114.73 (d, $^2J_{C-F}$=23.2 Hz; C27), 113.13 (C17), 88.23 (C10), 81.25 (C9), 77.95 (C3), 74.37 (C7), 66.24 (C5), 60.39 (C4), 56.91 (C20-OCH$_3$), 56.71 (C10-OCH$_3$), 47.26 (C15), 38.37 (C6), 36.01 (C8), 35.46 (C1-NCH$_3$), 33.86 (C24), 32.76 (C2), 26.78 (C29), 15.88 (C14-CH$_3$), 14.60 (C6-CH$_3$), 12.35 (C4-CH$_3$).

Preparation of Maytansinoid 3
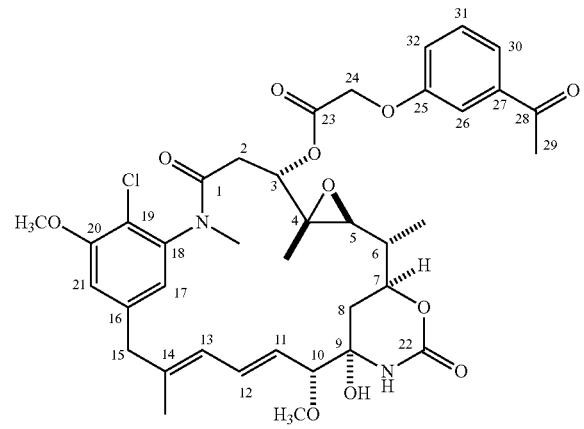 [SMILES: COc1cc2cc(c1Cl)N(C)C(=O)C[C@H](OC(=O)COc1cccc(C(C)=O)c1)[C@]1(C)O[C@H]1[C@H](C)[C@@H]1C[C@@](O)(NC(=O)O1)[C@H](OC)/C=C/C=C(\C)C2]
From the reaction of maytansinol with 2-(3-acetylphenoxy)acetic acid using Method B: Maytansinoid 3 was ob TABLE 1-continued Maytansinoids synthesized using Method A or B

| Compound | Structure | AA Spacer | Method | Yield |
|---|---|---|---|---|
| 6 | 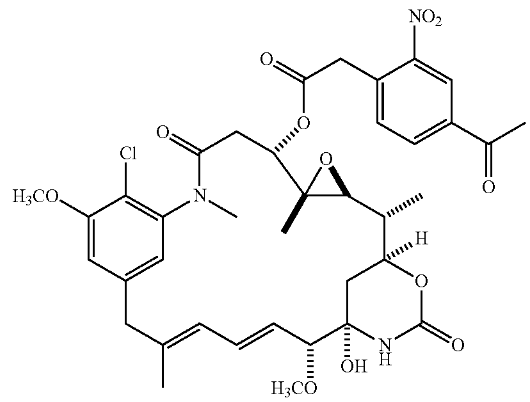 [SMILES: COc1cc2cc(c1Cl)N(C)C(=O)C[C@H](OC(=O)Cc1ccc(C(C)=O)cc1[N+](=O)[O-])[C@]1(C)O[C@H]1[C@H](C)[C@@H]1C[C@@](O)(NC(=O)O1)[C@H](OC)/C=C/C=C(\C)C2] | — | A | 27% |
| 7 | 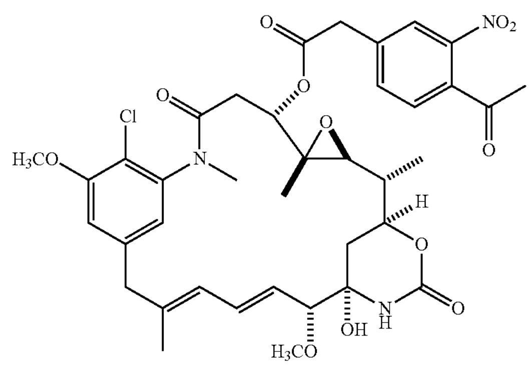 [SMILES: COc1cc2cc(c1Cl)N(C)C(=O)C[C@H](OC(=O)Cc1ccc(C(C)=O)c([N+](=O)[O-])c1)[C@]1(C)O[C@H]1[C@H](C)[C@@H]1C[C@@](O)(NC(=O)O1)[C@H](OC)/C=C/C=C(\C)C2] | — | A | 25% |
| 8 | 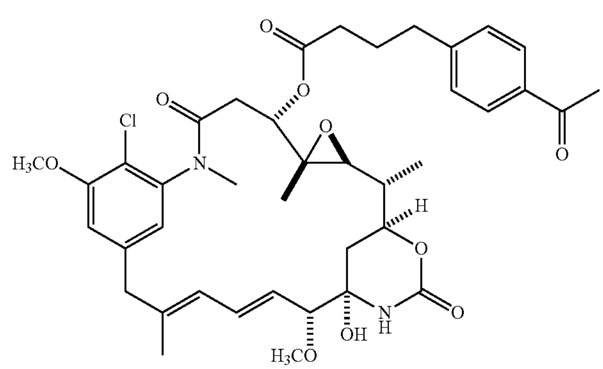 [SMILES: COc1cc2cc(c1Cl)N(C)C(=O)C[C@H](OC(=O)CCCc1ccc(C(C)=O)cc1)[C@]1(C)O[C@H]1[C@H](C)[C@@H]1C[C@@](O)(NC(=O)O1)[C@H](OC)/C=C/C=C(\C)C2] | — | A | 27% |

TABLE 1-continued

Maytansinoids synthesized using Method A or B

| Compound | Structure | AA Spacer | Method | Yield |
|---|---|---|---|---|
| 9 | 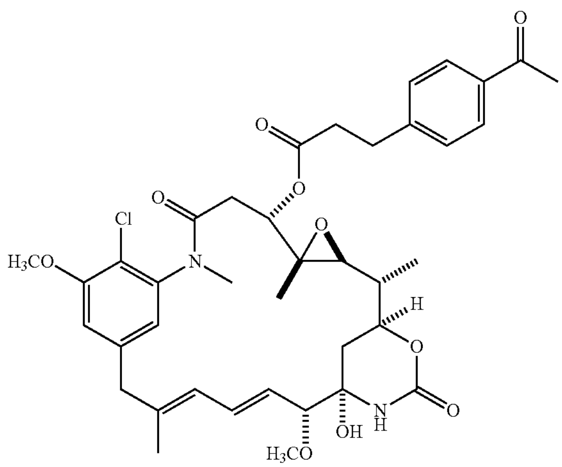 [SMILES: COc1cc2cc(c1Cl)N(C)C(=O)C[C@H](OC(=O)CCc1ccc(C(C)=O)cc1)[C@]1(C)O[C@H]1[C@H](C)[C@@H]1C[C@@](O)(NC(=O)O1)[C@H](OC)/C=C/C=C(\C)C2] | — | A | 13% |
| 10 | 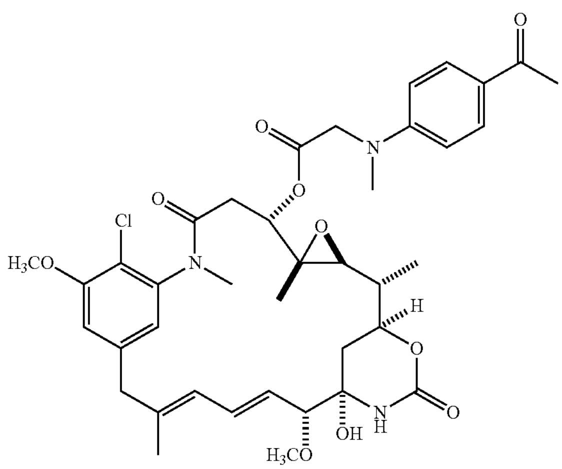 [SMILES: COc1cc2cc(c1Cl)N(C)C(=O)C[C@H](OC(=O)CN(C)c1ccc(C(C)=O)cc1)[C@]1(C)O[C@H]1[C@H](C)[C@@H]1C[C@@](O)(NC(=O)O1)[C@H](OC)/C=C/C=C(\C)C2] | — | A | 33% |
| 11 | 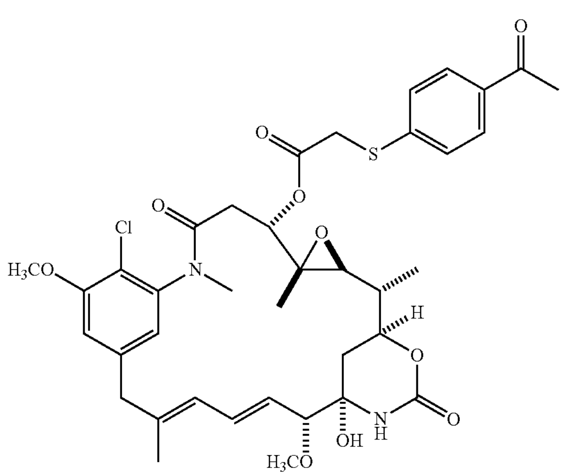 [SMILES: COc1cc2cc(c1Cl)N(C)C(=O)C[C@H](OC(=O)CSc1ccc(C(C)=O)cc1)[C@]1(C)O[C@H]1[C@H](C)[C@@H]1C[C@@](O)(NC(=O)O1)[C@H](OC)/C=C/C=C(\C)C2] | — | A | 72% |

TABLE 1-continued

Maytansinoids synthesized using Method A or B

| Compound | Structure | AA Spacer | Method | Yield |
|---|---|---|---|---|
| 12 | 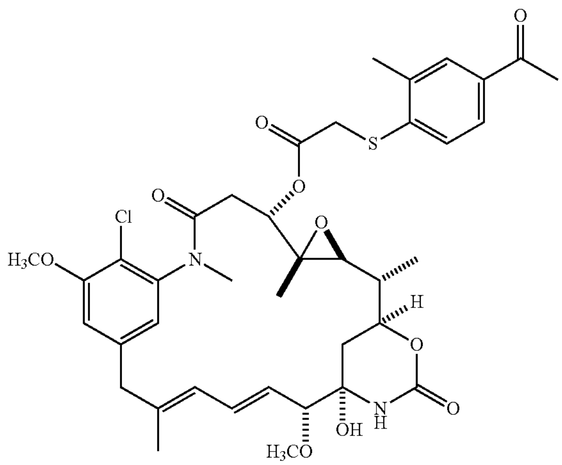 [SMILES: COc1cc2cc(c1Cl)N(C)C(=O)C[C@H](OC(=O)CSc1ccc(C(C)=O)cc1C)[C@]1(C)O[C@H]1[C@H](C)[C@@H]1C[C@@](O)(NC(=O)O1)[C@H](OC)/C=C/C=C(\C)C2] | — | A | 72% |
| 13 | 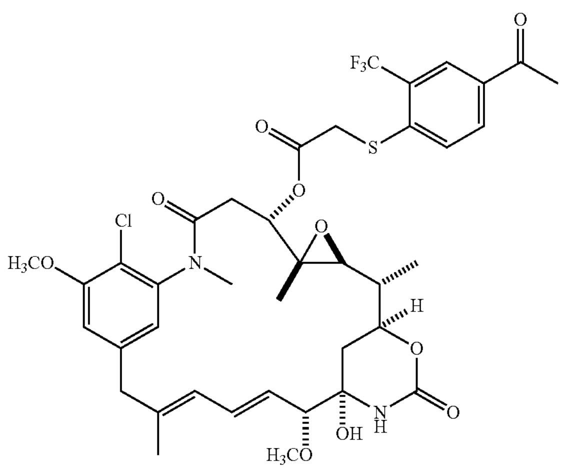 [SMILES: COc1cc2cc(c1Cl)N(C)C(=O)C[C@H](OC(=O)CSc1ccc(C(C)=O)cc1C(F)(F)F)[C@]1(C)O[C@H]1[C@H](C)[C@@H]1C[C@@](O)(NC(=O)O1)[C@H](OC)/C=C/C=C(\C)C2] | — | A | 47% |
| 14 | 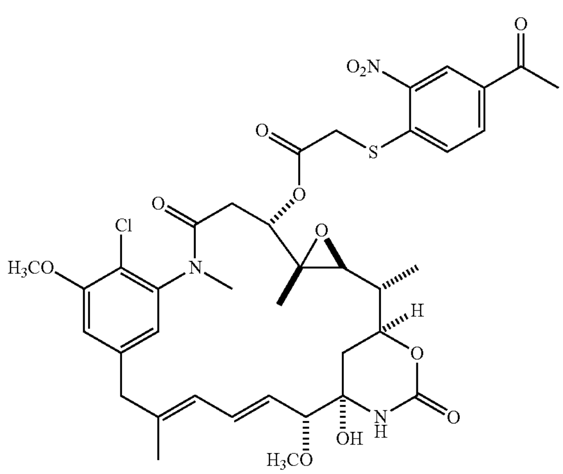 [SMILES: COc1cc2cc(c1Cl)N(C)C(=O)C[C@H](OC(=O)CSc1ccc(C(C)=O)cc1[N+](=O)[O-])[C@]1(C)O[C@H]1[C@H](C)[C@@H]1C[C@@](O)(NC(=O)O1)[C@H](OC)/C=C/C=C(\C)C2] | — | A | 45% |

TABLE 1-continued

Maytansinoids synthesized using Method A or B

| Compound | Structure | AA Spacer | Method | Yield |
|---|---|---|---|---|
| 15 | 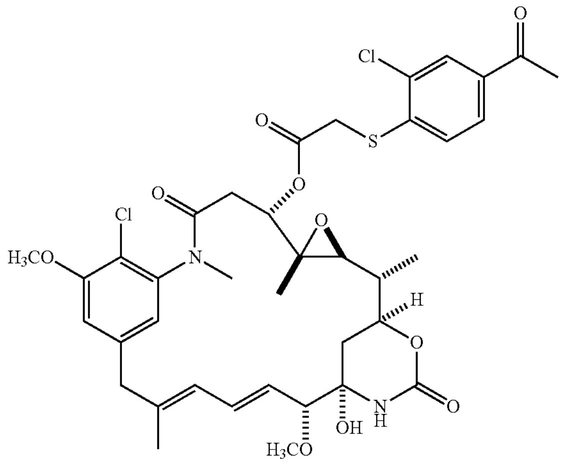 [SMILES: COc1cc2cc(c1Cl)N(C)C(=O)C[C@H](OC(=O)CSc1ccc(C(C)=O)cc1Cl)[C@]1(C)O[C@H]1[C@H](C)[C@@H]1C[C@@](O)(NC(=O)O1)[C@H](OC)/C=C/C=C(\C)C2] | — | B | 4% |
| 16 | 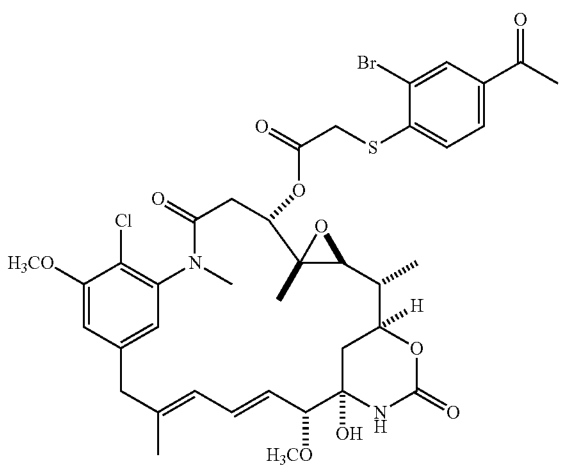 [SMILES: COc1cc2cc(c1Cl)N(C)C(=O)C[C@H](OC(=O)CSc1ccc(C(C)=O)cc1Br)[C@]1(C)O[C@H]1[C@H](C)[C@@H]1C[C@@](O)(NC(=O)O1)[C@H](OC)/C=C/C=C(\C)C2] | — | B | 6% |
| 17 | 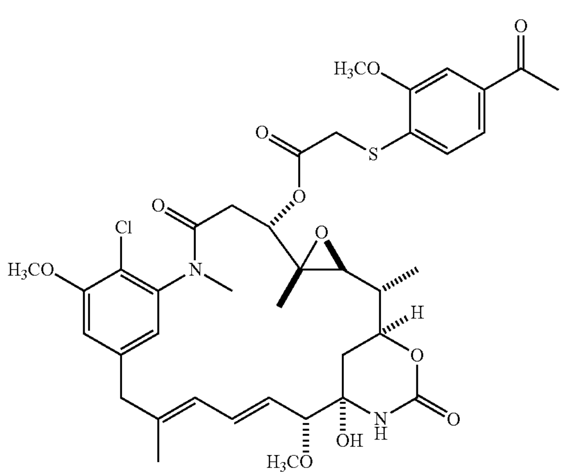 [SMILES: COc1cc(C(C)=O)ccc1SCC(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C] | — | B | 11% |

TABLE 1-continued

Maytansinoids synthesized using Method A or B

| Compound | Structure | AA Spacer | Method | Yield |
|---|---|---|---|---|
| 18 | 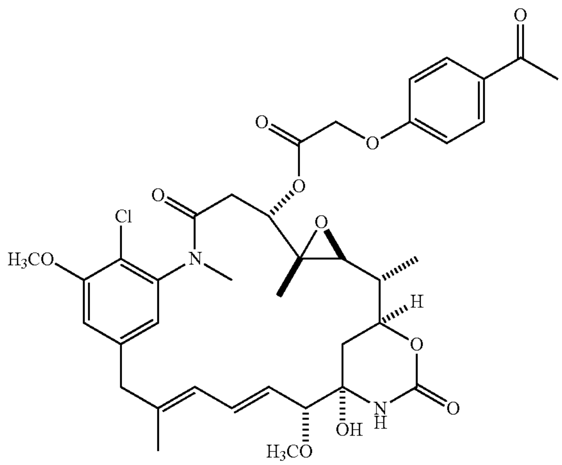 [SMILES: COc1cc2cc(c1Cl)N(C)C(=O)C[C@H](OC(=O)COc1ccc(C(C)=O)cc1)[C@]1(C)O[C@H]1[C@H](C)[C@@H]1C[C@@](O)(NC(=O)O1)[C@H](OC)/C=C/C=C(\C)C2] | — | B | 49% |
| 19 | 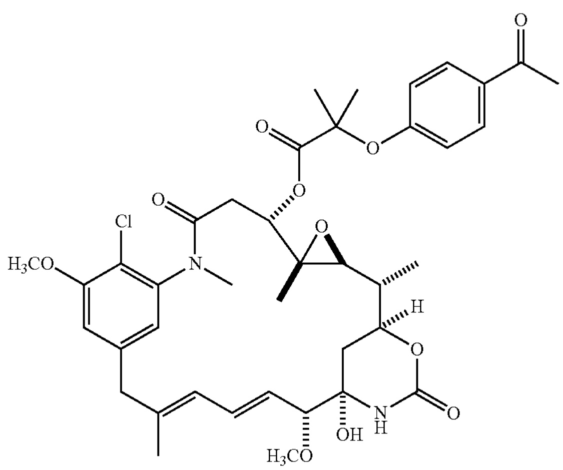 [SMILES: COc1cc2cc(c1Cl)N(C)C(=O)C[C@H](OC(=O)C(C)(C)Oc1ccc(C(C)=O)cc1)[C@]1(C)O[C@H]1[C@H](C)[C@@H]1C[C@@](O)(NC(=O)O1)[C@H](OC)/C=C/C=C(\C)C2] | — | B | 13% |
| 20 | 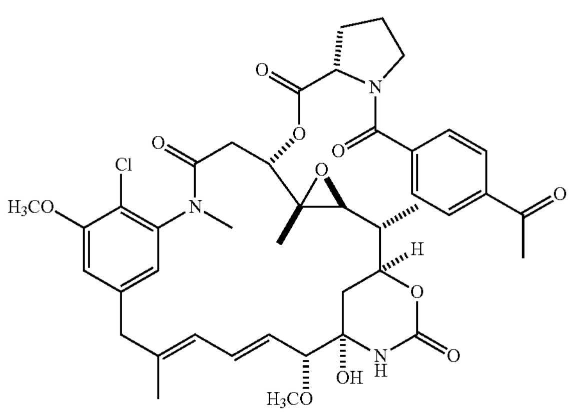 | Pro | A | 5% |

TABLE 1-continued

Maytansinoids synthesized using Method A or B

| Compound | Structure | AA Spacer | Method | Yield |
|---|---|---|---|---|
| 21 | 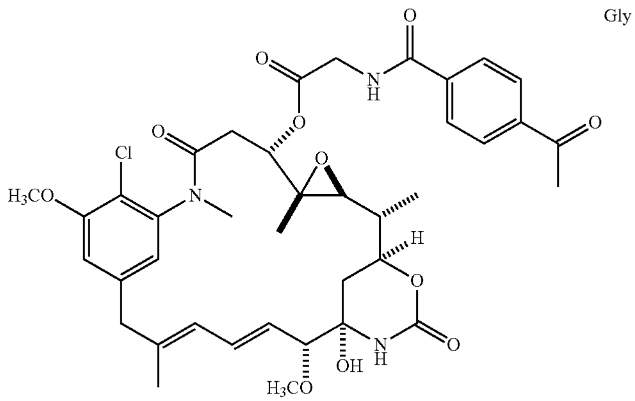 | Gly | A | 6% |
| 22 | 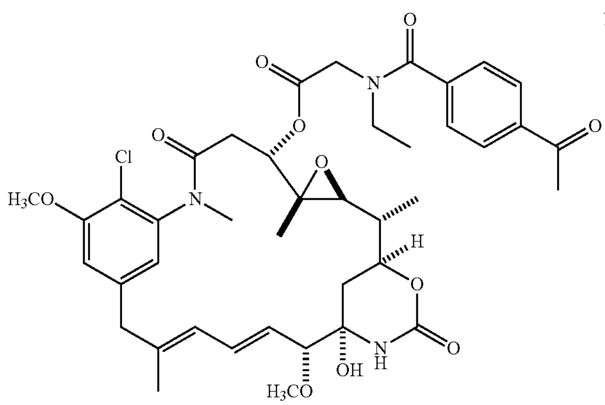 | N—Et—Gly | A | 9% |
| 23 | 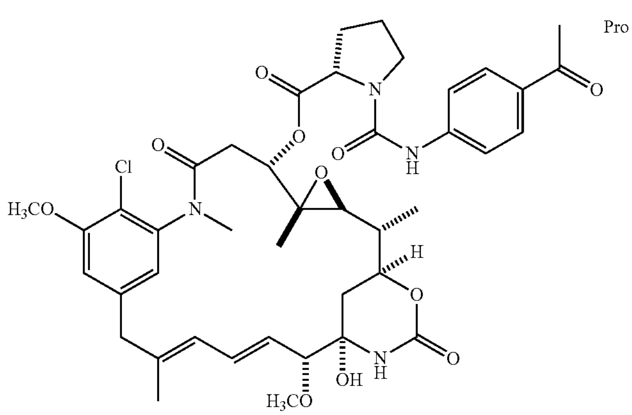 | Pro | A | 21% |

Example 3

Three-step synthesis of keto-maytansinoids via esterification with an Fmoc-protected amino acid, cleavage of Fmoc group and condensation with a keto acid.

General Method C—Step 1: Reaction of Maytansinol with an Fmoc-Protected Amino Acid.

Maytansinol (565 mg, 1.00 mmol, 1.0 eq), the Fmoc-protected amino acid (3.00 mmol, 3.0 eq), DMAP (982 mg, 8.00 mmol, 8.0 eq), and scandium(III) trifluoromethanesulfonate (541 mg, 1.1 mmol, 1.1 eq) were dissolved under N₂ atmosphere in anhydrous DCM (10 mL) at the presence of activated molecular sieves (1 g, 4 Å, 325 mesh particle size, Sigma Aldrich). The mixture was cooled to 4° C. using an ice/water bath and left stirring for 30 min to reach that temperature. After this time DIC (2.47 mL, 16.0 mmol, 16.0 eq) was added within 10 min (~0.25 mL/min) and the reaction mixture was stirred at 4° C. for 2 h and allowed to reach room temperature gradually during this time. The mixture was filtered by gravity. The filtrate was diluted with DCM (50 mL) and was then washed with sodium phosphate buffer (50 mL×3, pH 7.5) and brine (50 mL). The organic layer was then dried over anhydrous sodium sulfate, filtered by gravity, and the solvent was removed with a rotary evaporator at 40° C. to a final volume of approximately 10 mL. The crude was purified on a Biotage Isolera One flash purification System, with a pre-packed SNAP ULTRA 50 g cartridge, with Biotage® HP-Sphere™ spherical silica (linear gradient from 100% DCM to 90/10 DCM/methanol in 25 CV). The solvent was removed with a rotatory evaporator at 40° C. for 2 h to obtain the respective product as a yellowish to yellow solid.

General Method C—Step 2: Deprotection of the Fmoc Group.

The Fmoc-protected intermediate (0.53 mmol, 1.0 eq) was dissolved in DCM (5 mL), and to this solution was added tris-(2-aminoethyl)amine (0.320 mL, 2.13 mmol, 4.0 eq) within 10 s. The reaction mixture was left stirring at room temperature for 1 h. The white precipitate formed was filtered off over a Celite pad, washed with DCM (20 mL), and the yellow filtrate was evaporated to dryness with a rotary evaporator at 40° C. for 2 h, and further dried under high vacuum for 4 h to afford the free amine which was immediately used in the next step without further purification.

General Method C—Step 3: Reaction of the Amine-Maytansinoid with a Keto Acid.

The free amine intermediate (77.0 μmol, 1.0 eq), the keto acid (150 μmol, 2.0 eq), HATU (35 mg, 94.0 μmol, 1.2 eq), HOAt (13 mg, 94.0 μmol, 1.2 eq), and N-methylmorpholine (17 μL, 150 μmol, 2.0 eq) were dissolved under N₂ atmosphere in anhydrous DMF (1 mL). The mixture was left stirring at room temperature overnight. The reaction mixture was diluted with DCM (5 mL) and was washed with a saturated solution of ammonium chloride (5 mL×5) and brine (5 mL). The organic phase was then dried over anhydrous sodium sulfate, filtered by gravity and the solvent was removed with a rotary evaporator at 40° C. The crude was purified on a Biotage Isolera One flash purification System with a pre-packed SNAP ULTRA C-18 12 g cartridge, Biotage HP-Sphere™ C18, 25 μm spherical silica (linear gradient system from 80/20 water/MeCN to 100% MeCN in 20 CV). The product-containing fractions were combined, frozen in liquid nitrogen, and lyophilized for 24 h to afford the respective keto maytansinoid.

TABLE 2

Maytansinoids synthesized using Method C (steps 1-3)

| Compound | Structure | AA Spacer | Yield step 1 | Yield step 2 | Yield step 3 |
|---|---|---|---|---|---|
| 44 | 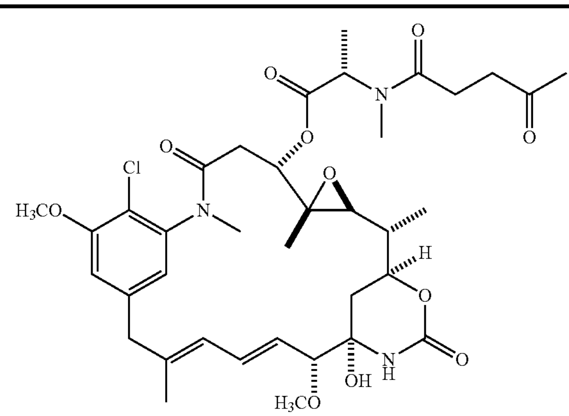 | N—Me—Ala | 53% | 87% | 30% |
| 24 | 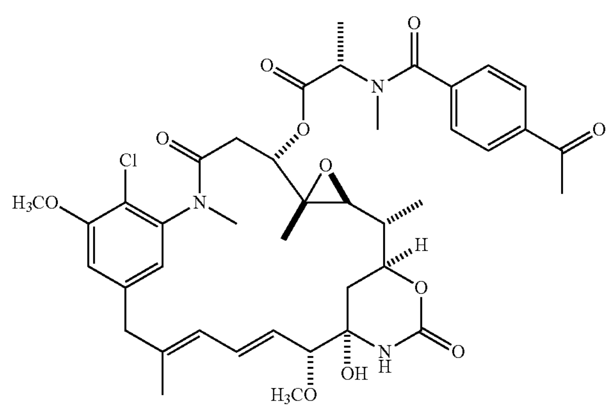 [SMILES: COc1cc2cc(c1Cl)N(C)C(=O)C[C@H](OC(=O)[C@H](C)N(C)C(=O)c1ccc(C(C)=O)cc1)[C@]1(C)O[C@H]1[C@H](C)[C@@H]1C[C@@](O)(NC(=O)O1)[C@H](OC)/C=C/C=C(\C)C2] | N—Me—Ala | 53% | 87% | 16% |

TABLE 2-continued

Maytansinoids synthesized using Method C (steps 1-3)

| Compound | Structure | AA Spacer | Yield step 1 | Yield step 2 | Yield step 3 |
|---|---|---|---|---|---|
| 25 | 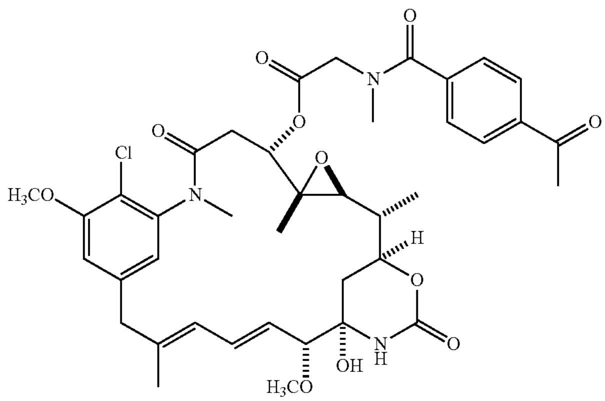 [SMILES: COc1cc2cc(c1Cl)N(C)C(=O)C[C@H](OC(=O)CN(C)C(=O)c1ccc(C(C)=O)cc1)[C@]1(C)O[C@H]1[C@H](C)[C@@H]1C[C@@](O)(NC(=O)O1)[C@H](OC)/C=C/C=C(\C)C2] | Sar | 47% | 98% | 23% |
| 26 | 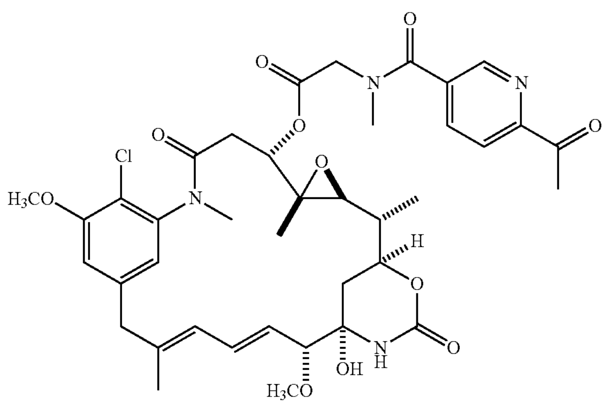 [SMILES: COc1cc2cc(c1Cl)N(C)C(=O)C[C@H](OC(=O)CN(C)C(=O)c1ccc(C(C)=O)nc1)[C@]1(C)O[C@H]1[C@H](C)[C@@H]1C[C@@](O)(NC(=O)O1)[C@H](OC)/C=C/C=C(\C)C2] | Sar | 47% | 98% | 8% |
| 27 | 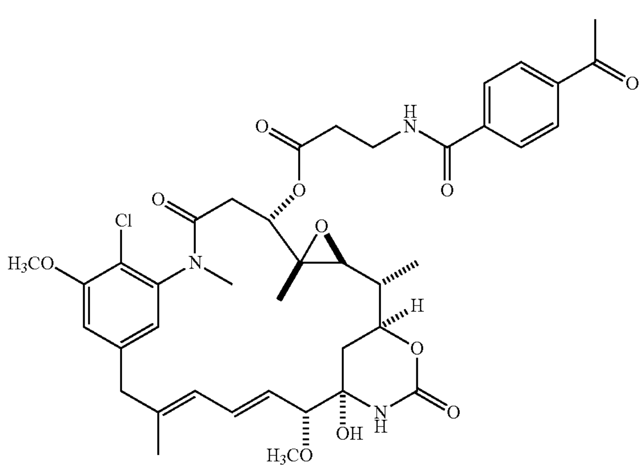 [SMILES: COc1cc2cc(c1Cl)N(C)C(=O)C[C@H](OC(=O)CCNC(=O)c1ccc(C(C)=O)cc1)[C@]1(C)O[C@H]1[C@H](C)[C@@H]1C[C@@](O)(NC(=O)O1)[C@H](OC)/C=C/C=C(\C)C2] | β—Ala | 58% | 95% | 12% |

Example 4

Preparation of Maytansinoid 28

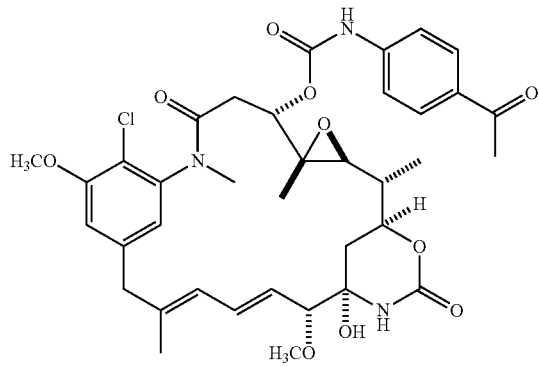 [SMILES: COc1cc2cc(c1Cl)N(C)C(=O)C[C@H](OC(=O)Nc1ccc(C(C)=O)cc1)[C@]1(C)O[C@H]1[C@H](C)[C@@H]1C[C@@](O)(NC(=O)O1)[C@H](OC)/C=C/C=C(\C)C2]

Maytansinol (56.5 mg, 0.10 mmol, 1.0 eq) was dissolved in dry DCM (10 mL), a solution of zinc(II) chloride in diethyl ether (0.3 mL, 0.30 mmol, 3.0 eq, 1 M solution) was added at room temperature under $N_2$ atmosphere and left stirring for 10 min. 4-Acetylphenylisocyanate (48.3 mg, 0.30 mmol, 3.0 eq) was added, within 10 s, and the resulting solution was stirred at room temperature for 5 h. After this time, completion of the reaction was confirmed by HPLC analysis (PDA 220 nm). The volatiles were removed with a rotatory evaporator at 40° C. The crude was purified by NP chromatography using a Biotage Isolera One flash purification System with a pre-packed SNAP ULTRA 10 g cartridge containing Biotage® HP-Sphere™ spherical silica (linear gradient system from 100% DCM to 90/10 DCM/methanol in 13 CV) followed by RP chromatography with a pre-packed SNAP ULTRA C-18 12 g cartridge Biotage® HP-Sphere™ C18, 25 µm spherical silica (linear gradient from 80/20 water/MeCN to 100% MeCN in 30 CV). The product-containing fractions were combined, frozen in liquid nitrogen, and lyophilized for 24 h to afford compound 28 as a white solid. Yield: 20 mg (28%). Purity by RP-HPLC (220 nm)≥95%. LRMS-ESI (m/z) calcd. for: $C_{37}H_{45}ClN_3O_{10}$ [M+H]$^+$: 726.27. Found: 726.25. LRMS-ESI (m/z) calcd. for: $C_{37}H_{43}ClN_3O_{10}$ [M–H]$^-$: 724.27. Found: 724.43.

Example 5

Preparation of Maytansinoid 29
Synthesis of May-ONp:

To a solution of maytansinol (88 mg, 155 µmol, 1.0 eq) in DCM (8 mL) was added pyridine (25 µL, 310 µmol, 2.0 eq) at room temperature. The resulting clear solution was stirred for 15 min before cooling down to 4° C. and adding p-nitrophenyl chloroformate (219 mg, 1.08 mmol, 7.0 eq) in DCM (4 mL) after which a white precipitate was formed immediately. The reaction mixture was stirred for 24 h at room temperature. The crude material was concentrated using a rotary evaporator at 40° C. for 1 h and was purified with a Biotage Isolera One flash purification System using a pre-packed SNAP ULTRA 25 g cartridge with Biotage® HP-Sphere™ spherical silica (linear gradient from 100% ethyl acetate to 40/60 ethyl acetate/DCM in 50 CV). The product-containing fractions were dried with the rotary evaporator at 40° C. for 30 min and under high vacuum for another 30 min to afford the intermediate May-ONp as a white solid. Yield: 102 mg (90%). LRMS-ESI (m/z) calcd. for $C_{35}H_{41}ClN_3O_{12}$ [M+H]$^+$: 730.23. Found: 730.01.

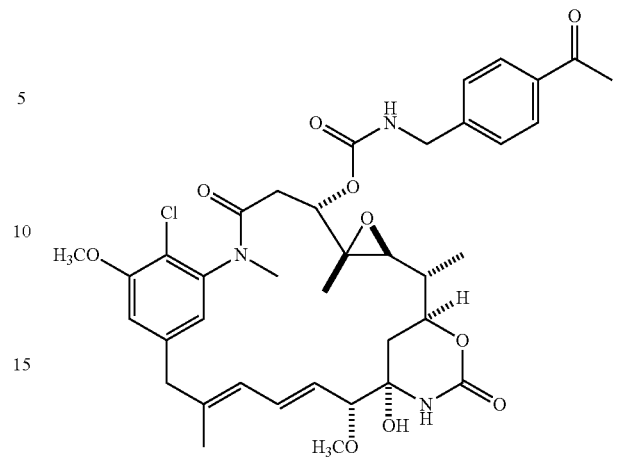

Synthesis of Maytansinoid 29:

To a solution of compound May-ONp (3.7 mg, 5.00 µmol, 1.0 eq) in DCM (1 mL) was added a solution of 4-(aminomethyl)acetophenone (1.1 mg, 7.50 µmol, 1.5 eq) in DCM/DMF (2:0.1 v/v) at room temperature and was stirred for 5 min before adding triethylamine (2 µL, 10.0 µmol, 2.0 eq). The reaction mixture was stirred at room temperature for 2 h and at 60° C. overnight. The crude material was concentrated at 40° C. for 1 h and was purified with a Biotage Isolera One flash purification System using a pre-packed SNAP ULTRA 10 g cartridge with Biotage® HP-Sphere™ spherical silica (linear gradient from 100% chloroform until 90/10 chloroform/methanol in 20 CV). The product-containing fractions were dried with the rotary evaporator at 40° C. for 30 min and under high vacuum for another 30 min to afford compound 29 as a white solid. Yield: 1 mg (27%). Purity by RP-HPLC (220 nm)>95%. LRMS-ESI (m/z) calcd. for $C_{38}H_{46}ClN_3O_{10}$ [M+H]$^+$: 739.28. Found: 739.96.

Example 6

Preparation of Albumin-Binding Maytansinoids

General Method D for the Synthesis of Albumin-Binding Maytansinoids from a Keto-Maytansinoid and a Maleimido-Hydrazide Linker:

To a stirred solution of the keto-maytansinoid (1.0 eq), in dry solvent (suitable solvents are DCM, DMSO, dioxane, 2-methyltetrahydrofuran) at room temperature under $N_2$ atmosphere were added molecular sieves (from 1:1 to 5:1 w/w) and a catalyst (TFA, p-toluenesulfonic acid, amberlyst-H form, amberlite-Na form) followed by a solution of the hydrazide linker (from 1.0-5.0 eq) in dry DMSO. The reaction mixture was stirred at room temperature and conversion was confirmed using HPLC analysis (PDA 220 nm) (>90% conversion). The reaction mixture was filtered, concentrated with a rotary evaporator at 30° C. and purified by chromatography with a Biotage Isolera One flash purification System using a pre-packed SNAP ULTRA Biotage® HP-Sphere™ spherical silica (linear gradient from 100% DCM to 90/10 DCM/methanol), dried with the rotary evaporator at 30° C. for 30 min, and under high vacuum for another 30 min to afford the free acid. The product was re-dissolved in suitable solvent (methanol, acetone, 2-methyltetrahydrofuran, or other organic polar solvents) and then was neutralized using salts solutions (sodium salts, potassium salts, triethylammonium salts) until a pH range 5.5-7.5 was reached. The solution was frozen in liquid nitrogen, and lyophilized for 24 h to afford the compound as a salt. The content of the counterion was determined by IC. The sodium ion content ranged from 0.2-1.0 eq (ca. 0.2-0.9%) and the triethylammonium ion content from 0.8-2.0 eq (ca. 6-16%).

Preparation of Albumin-Binding Maytansinoid 30

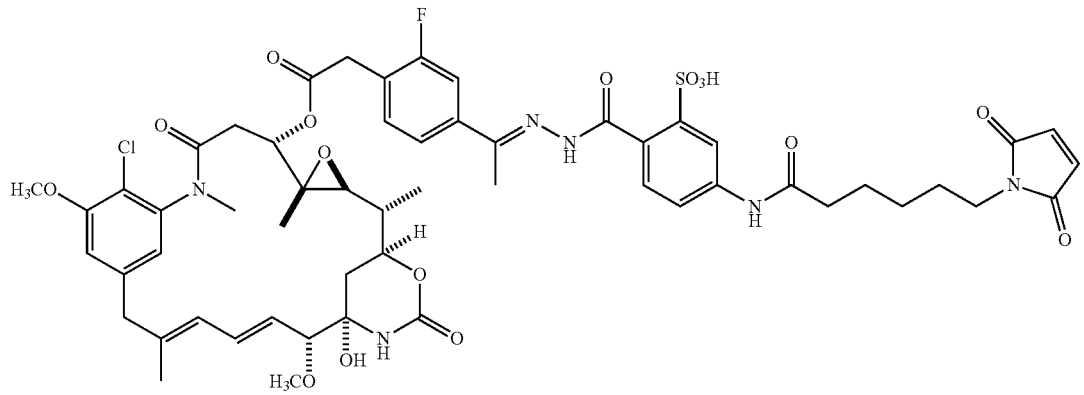 [SMILES: COc1cc2cc(c1Cl)N(C)C(=O)C[C@H](OC(=O)Cc1ccc(/C(C)=N/NC(=O)c3ccc(NC(=O)CCCCCN4C(=O)C=CC4=O)cc3S(=O)(=O)O)cc1F)[C@]1(C)O[C@H]1[C@H](C)[C@@H]1C[C@@](O)(NC(=O)O1)[C@H](OC)/C=C/C=C(\C)C2]

From the Reaction of Maytansinoid 2 with Linker 1:

To a stirred solution of maytansinoid 2 (170 mg, 0.23 mmol, 1.0 eq), molecular sieves (0.2 g, powder, activated, 4 Å, 325 mesh particle size), and Amberlyst®-H (20 mg, macroporous, 30-60 mesh) in dry DCM (2 mL) at room temperature under $N_2$ atmosphere was added a solution of the linker 1 (51 mg, 0.12 mmol, 2.0 eq) in dry DMSO (0.6 mL). The reaction mixture was stirred at room temperature, and after 3 h HPLC analysis (PDA 220 nm) confirmed completion of the reaction (>98% conversion). The reaction mixture was concentrated with a rotary evaporator at 30° C., filtered over a 0.45 μm syringe filter (Macherey-Nagel, Chromafil® PTFE-O-45/25). The filtrate was diluted with dry DCM (8 mL) and was purified with a Biotage Isolera One flash purification System using a pre-packed SNAP ULTRA 10 g cartridge with Biotage® HP-Sphere™ spherical silica (linear gradient from 100% DCM to 90/10 DCM/MeOH in 22 CV). The combined product-containing fractions were dried with the rotary evaporator at 30° C. for 30 min and under high vacuum for another 30 min to afford the free acid form of 30 as a white-yellow solid. The solid was dissolved in MeOH/acetone (50:50 v/v, ca. 4 mL in total) and then it was neutralized with a 5 mM solution of $NaHCO_3$ in Millipore water until pH 6.8-7.1 (pH measured using pH meter). The solution was frozen in liquid nitrogen, and lyophilized for 24 h to afford maytansinoid-prodrug 30 as a white-yellow foam. Yield: 161 mg (60%). LRMS-ESI (m/z) calcd. for: $C_{55}H_{61}ClFN_6O_{16}S$ [M–H]⁻: 1147.36. Found: 1147.84. The content of $Na^+$ ranged from 0.2-0.8%.

Preparation of Albumin-Binding Maytansinoid 31

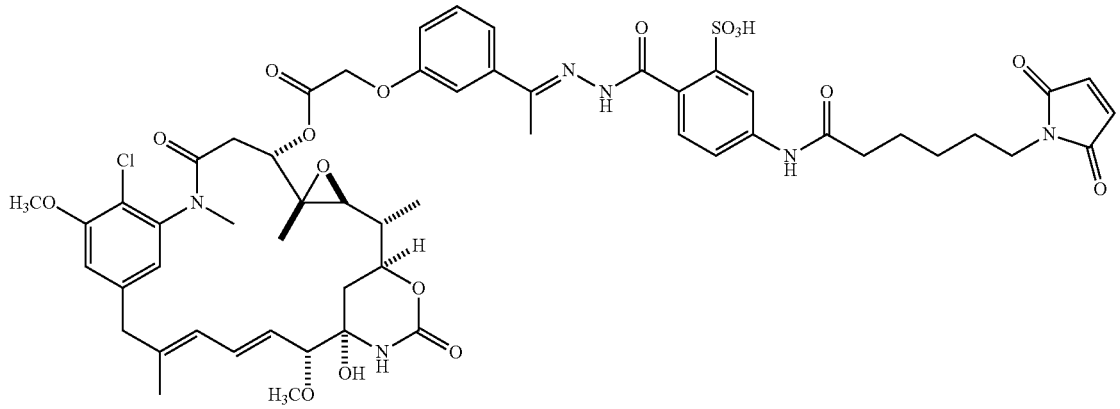

From the Reaction of Maytansinoid 3 with Linker 1:

To a stirred solution of maytansinoid 3 (186 mg, 0.25 mmol, 1.0 eq), molecular sieves (0.4 g, powder, activated, 4 Å, 325 mesh particle size, Sigma Aldrich), and Amberlite® (IR120 Na form, 484 mg, 2.1 mmol/mL, 4.0 eq) in dry dichloromethane (4 mL) at room temperature under $N_2$ atmosphere was added a solution of linker 1 (329 mg, 0.77 mmol, 2.5 eq) in dry DMSO (4 mL). The reaction mixture was stirred at room temperature, and after 6 h HPLC analysis (PDA 220 nm) confirmed completion of the reaction (>98% conversion). The reaction mixture was concentrated with a rotary evaporator at 30° C., filtered over a 0.45 μm syringe filter (Macherey-Nagel, Chromafil® PTFE-0-45/25). The filtrate was neutralized with sodium hydroxide (318 μL of a 1M NaOH solution, 1.3 eq). The neutralized mixture was added dropwise to a 50 mL Falcon tube containing a cooled mixture (4° C. ice bath) of methyl t-butyl ether (27 mL) and isopropyl alcohol (14 mL) and centrifuge at 4° C. for 5 min. The supernatant was decanted, and the precipitate was re-suspended in dichloromethane (10 mL) and purified with a Biotage Isolera One flash purification System using a pre-packed SNAP ULTRA 10 g cartridge, with Biotage® HP-Sphere™ spherical silica (linear gradient from 100% DCM until 90/10 DCM/MeOH in 22 CV). The combined product-containing fractions were dried with the rotatory evaporator at 30° C. for 30 min and under high vacuum for another 10 h to afford 31 as a white-yellow solid. Yield: 156 mg (52%). Purity by RP-HPLC (220 nm)>95%. LRMS-ESI (m/z) calcd. for: $C_{55}H_{62}ClN_6O_{17}S$ [M−H]⁻: 1145.36. Found: 1145.87. The content of Na has a window of 0.2-0.8%.

TABLE 3

Albumin-binding maytansinoids synthesized using the general Method D

| Compound | Structure | Drug (Cmpd) | Yield (counter ion) |
|---|---|---|---|
| 45 | 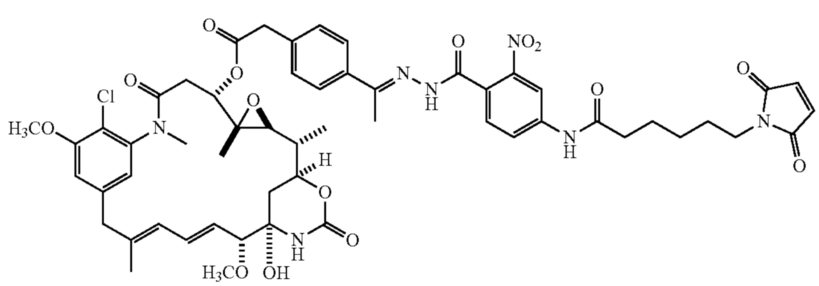 [SMILES: COc1cc2cc(c1Cl)N(C)C(=O)C[C@H](OC(=O)Cc1ccc(/C(C)=N/NC(=O)c3ccc(NC(=O)CCCCCN4C(=O)C=CC4=O)cc3[N+](=O)[O-])cc1)[C@]1(C)O[C@H]1[C@H](C)[C@@H]1C[C@@](O)(NC(=O)O1)[C@H](OC)/C=C/C=C(\C)C2] | 4 | 54% (−) |
| 32 | 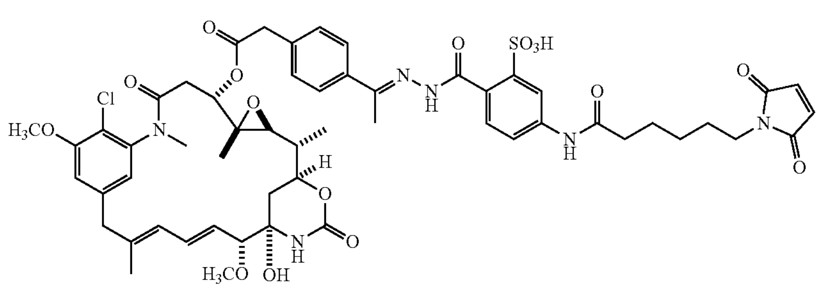 [SMILES: COc1cc2cc(c1Cl)N(C)C(=O)C[C@H](OC(=O)Cc1ccc(/C(C)=N/NC(=O)c3ccc(NC(=O)CCCCCN4C(=O)C=CC4=O)cc3S(=O)(=O)O)cc1)[C@]1(C)O[C@H]1[C@H](C)[C@@H]1C[C@@](O)(NC(=O)O1)[C@H](OC)/C=C/C=C(\C)C2] | 4 | 10% (Na⁺) |
| 33 | 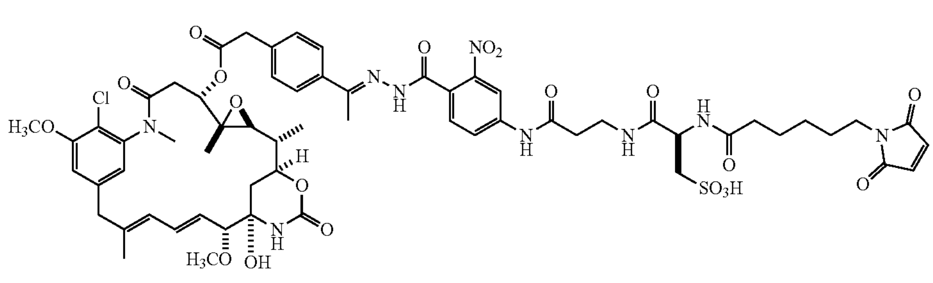 [SMILES: COc1cc2cc(c1Cl)N(C)C(=O)C[C@H](OC(=O)Cc1ccc(/C(C)=N/NC(=O)c3ccc(NC(=O)CCNC(=O)[C@H](CS(=O)(=O)O)NC(=O)CCCCCN4C(=O)C=CC4=O)cc3[N+](=O)[O-])cc1)[C@]1(C)O[C@H]1[C@H](C)[C@@H]1C[C@@](O)(NC(=O)O1)[C@H](OC)/C=C/C=C(\C)C2] | 4 | 33% (Na⁺) |

TABLE 3-continued

Albumin-binding maytansinoids synthesized using the general Method D

| Compound | Structure | Drug (Cmpd) | Yield (counter ion) |
|---|---|---|---|
| 45 | 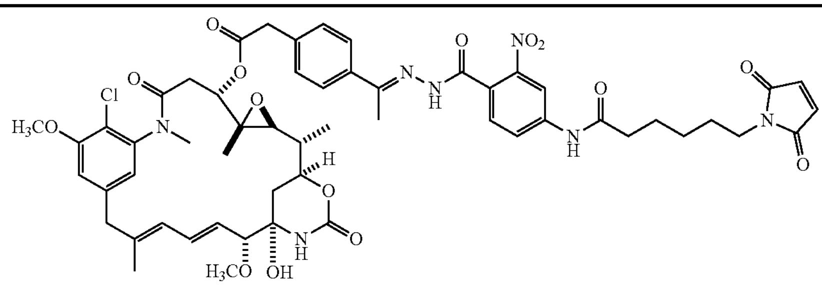 | 4 | 54% (−) |
| 34 | 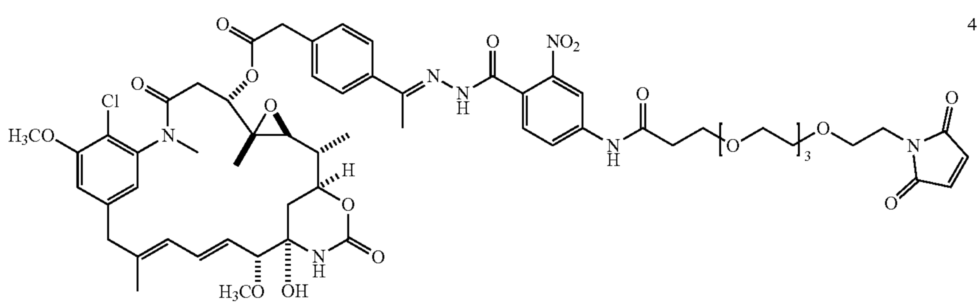 | 4 | 49% |
| 35 | 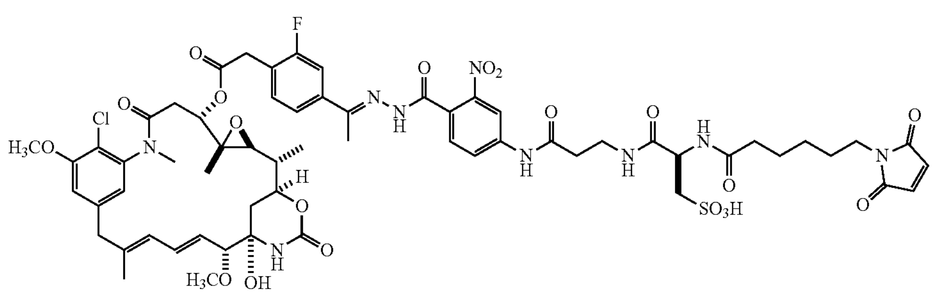 [SMILES: COc1cc2cc(c1Cl)N(C)C(=O)C[C@H](OC(=O)Cc1ccc(/C(C)=N/NC(=O)c3ccc(NC(=O)CCNC(=O)[C@H](CS(=O)(=O)O)NC(=O)CCCCCN4C(=O)C=CC4=O)cc3[N+](=O)[O-])cc1F)[C@]1(C)O[C@H]1[C@H](C)[C@@H]1C[C@@](O)(NC(=O)O1)[C@H](OC)/C=C/C=C(\C)C2] | 2 | 33% (Na⁺) |
| 36 | 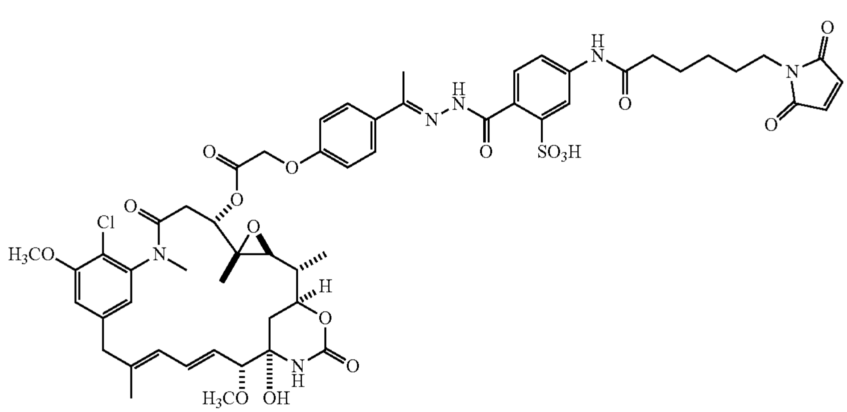 [SMILES: COc1cc2cc(c1Cl)N(C)C(=O)C[C@H](OC(=O)CSc1ccc(/C(C)=N/NC(=O)c3ccc(NC(=O)CCCCCN4C(=O)C=CC4=O)cc3S(=O)(=O)O)cc1)[C@]1(C)O[C@H]1[C@H](C)[C@@H]1C[C@@](O)(NC(=O)O1)[C@H](OC)/C=C/C=C(\C)C2] | 18 | 17% (Et₃NH⁺) |

TABLE 3-continued

Albumin-binding maytansinoids synthesized using the general Method D

| Compound | Structure | Drug (Cmpd) | Yield (counter ion) |
|---|---|---|---|
| 45 | 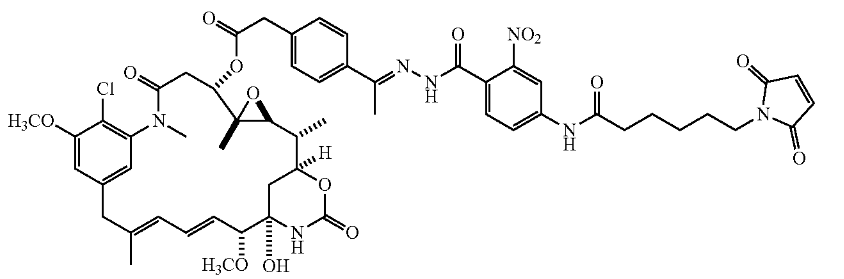 | 4 | 54% (−) |
| 37 | 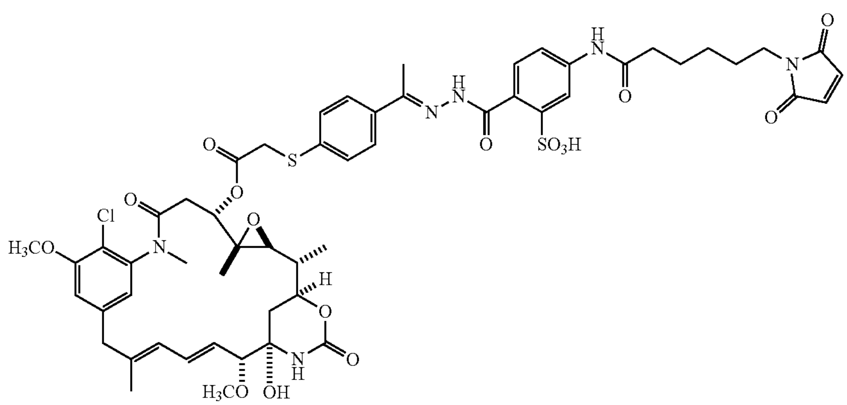 | 11 | 12% (Et$_3$NH$^+$) |
| 38 | 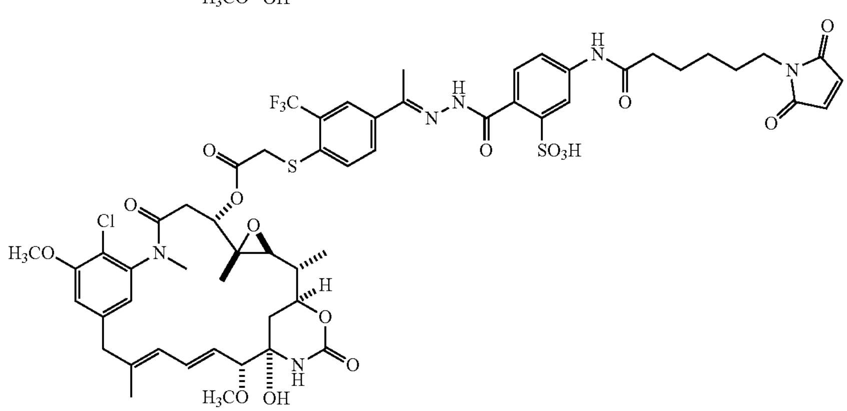 | 13 | 24% (Et$_3$NH$^+$) |
| 39 | 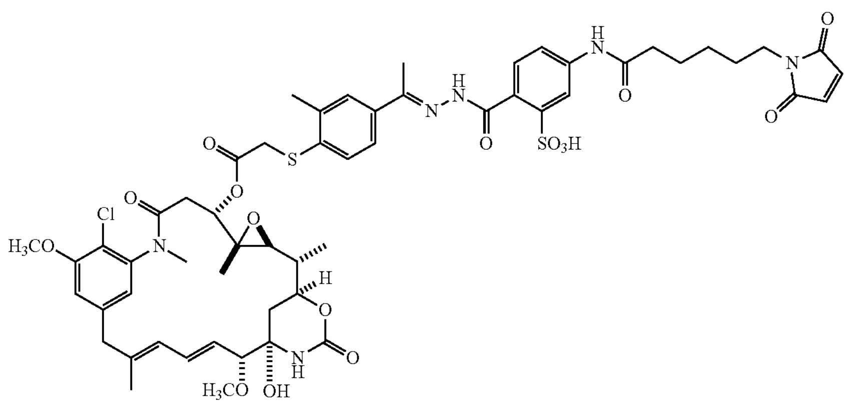 [SMILES: COc1cc2cc(c1Cl)N(C)C(=O)C[C@H](OC(=O)CSc1ccc(/C(C)=N/NC(=O)c3ccc(NC(=O)CCCCCN4C(=O)C=CC4=O)cc3S(=O)(=O)O)cc1C)[C@]1(C)O[C@H]1[C@H](C)[C@@H]1C[C@@](O)(NC(=O)O1)[C@H](OC)/C=C/C=C(\C)C2] | 12 | 24% (Et$_3$NH$^+$) |

TABLE 3-continued

Albumin-binding maytansinoids synthesized using the general Method D

| Compound | Structure | Drug (Cmpd) | Yield (counter ion) |
|---|---|---|---|
| 45 | 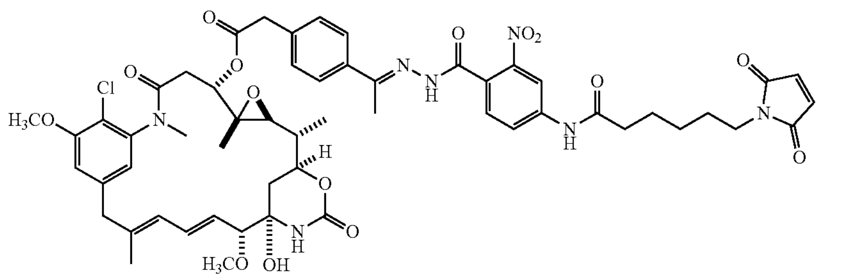 | 4 | 54% (−) |
| 40 | 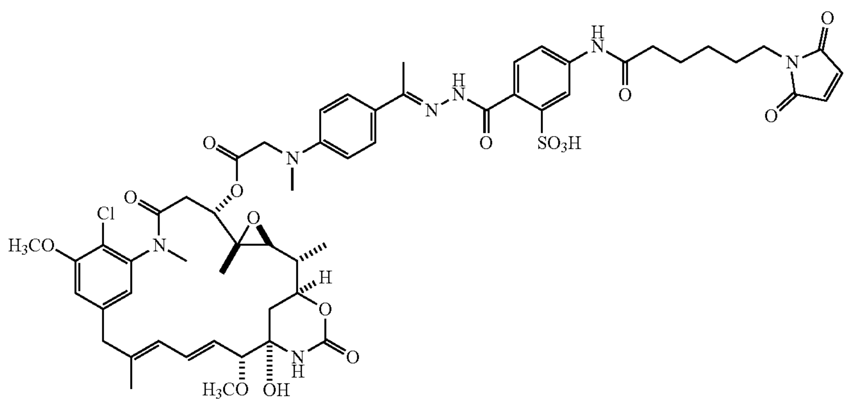 [SMILES: COc1cc2cc(c1Cl)N(C)C(=O)C[C@H](OC(=O)CN(C)c1ccc(/C(C)=N/NC(=O)c3ccc(NC(=O)CCCCCN4C(=O)C=CC4=O)cc3S(=O)(=O)O)cc1)[C@]1(C)O[C@H]1[C@H](C)[C@@H]1C[C@@](O)(NC(=O)O1)[C@H](OC)/C=C/C=C(\C)C2] | 10 | 12% (Et₃NH⁺) |
| 41 | 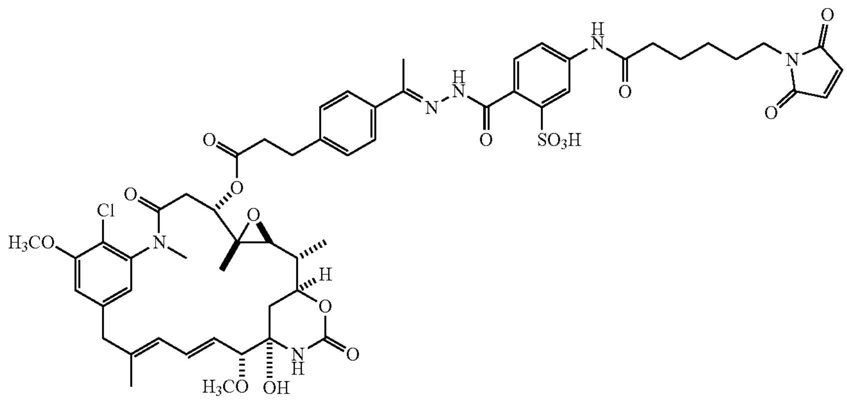 | 9 | 7% (Na⁺) |
| 42 | 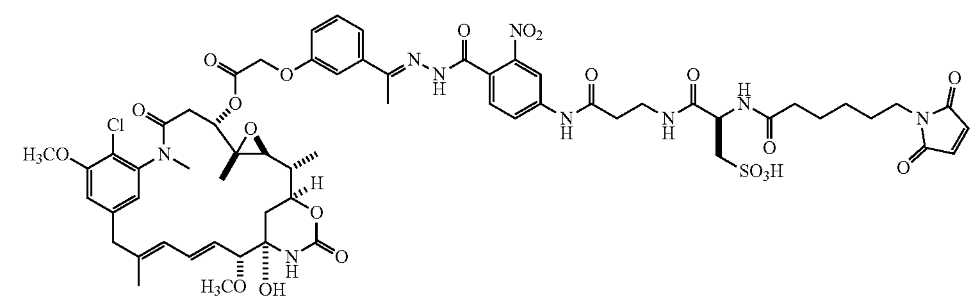 [SMILES: COc1cc2cc(c1Cl)N(C)C(=O)C[C@H](OC(=O)COc1cccc(/C(C)=N/NC(=O)c3ccc(NC(=O)CCNC(=O)[C@H](CS(=O)(=O)O)NC(=O)CCCCCN4C(=O)C=CC4=O)cc3[N+](=O)[O-])c1)[C@]1(C)O[C@H]1[C@H](C)[C@@H]1C[C@@](O)(NC(=O)O1)[C@H](OC)/C=C/C=C(\C)C2] | 3 | 73% (Na⁺) |

TABLE 3-continued

Albumin-binding maytansinoids synthesized using the general Method D

| Compound | Structure | Drug (Cmpd) | Yield (counter ion) |
|---|---|---|---|
| 45 | 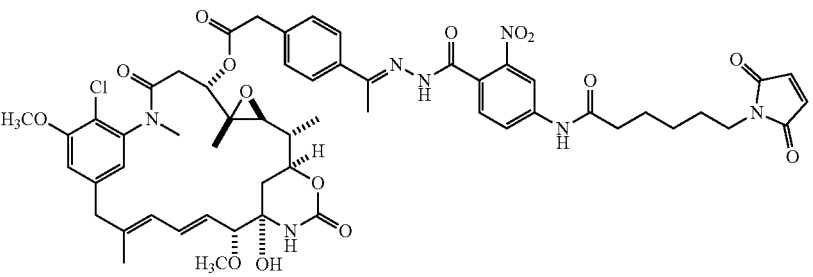 | 4 | 54% (–) |
| 43 | 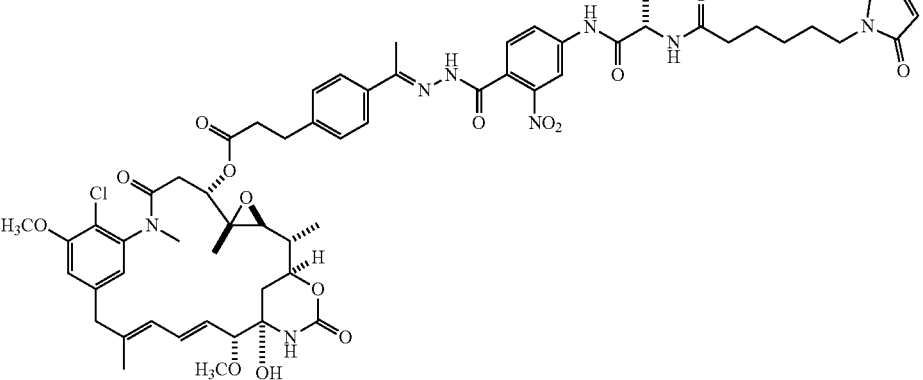 | 18 | 11% (Na$^+$) |

Example 7

Stability and Release Kinetics of Maytansinoid-HSA Conjugates in Buffer Solution at pH 4.0 and pH 7.4

For preparing HSA conjugates of albumin-binding maytansinoids, HSA (200 μM: 361.8 μL, 1078 μM free Cys34; 100 μM: 180.9 μL, 1078 μM free Cys34) was diluted with PBS buffer (4 mM sodium phosphate, 150 mM NaCl, pH 7.4) (200 μM: 678.2 μL; 100 μM: 859.1 μL) and DMSO (200 μM: 130.0 μL; 100 μM: 195.0 μL) and incubated in a heating block at 37° C. for 30 minutes. The albumin-binding maytansinoid was added as a 2 mM stock solution in DMSO (200 μM: 130.0 μL; 100 μM: 65.0 μL) to the preincubated HSA sample to produce a 200 μM or 100 μM solution of maytansinoid-prodrug and 300 μM or 150 μM of free Cys34. The mixture having a pH of 7.4 was allowed to react for 10 min at 37° C. and was then analyzed hourly for 24 hours by RP-HPLC (Phenomenex Aeris WP XB-C18, 3.6 μm, 250× 4.6 mm).

For studying the release kinetics at pH 4.0 the mixture was acidified with a mixture of 50 mM sodium acetate buffer pH 3.0 (200 μM: 119.3 μL; 100 μM: 125.2 μL) and 1 M HCl (200 μM: 12.7 μL; 100 μM: 6.8 μL) to reach pH 4.0. The mixture was subsequently analyzed hourly for 24 hours by RP-HPLC (Phenomenex Aeris WP XB-C18, 3.6 μm, 250× 4.6 mm).

The following RP-HPLC conditions were used: Phenomenex Aeris WP XB-C18 3.6 μm, 250×4.6 mm; eluent A (100% 20 mM Tris buffer pH 8.0) and eluent B (90:10, MeCN: water) eluting with a gradient of eluent B (25% 0-0.5 min, 25-35% 0.5-2.5 min, 35-85% 2.5-16 min, 85-95% 16-17 min, 95% 17-20 min, 95-25% 20-25 min, 25% 25-30 min, flow rate 1.0 mL/min). Column oven temperature 37° C.; autosampler temperature 37° C.; 20 μL of injection volume.

To quantify the percentage of free drug released, standard curves of the free maytansinoids were prepared at different concentrations (200 μM, 100 μM, 50 μM, 25 μM and 12.5 μM). The area under the curve (AUC) was determined at 250 nm.

TABLE 4

Release kinetics of maytansinoid-HSA conjugates at pH 4.0 and pH 7.4

| Maytansinoid | rel. $t_{1/2}$ at pH 4.1 | free maytansinoid after 24 h at pH 7.4 |
|---|---|---|
| 36 | 4.5 h* | 4.7%* |
| 41 | 4.0 h* | 4.6%* |
| 31 | 4.5 h* | 4.0%* |
|  | 6.0 h** | 3.7%** |
| 33 | 7.0 h* | 6.5%* |
| 32 | 4.0 h* | 9.5%* |
| 37 | 5.5 h* | 3.9%* |
| 30 | 3.5 h** | 9.6%** |
| 40 | 3.5 h* | 8.9%* |
| 39 | 5.5 h* | 9.6%* |
| 38 | 8.5 h* | 4.9%* |
| 42 | 45.4 h** | 4.8%** |

*measured at 200 μM
**measured at 100 μM

Example 8

Stability of Maytansinoids and Maytansinoid-HSA Conjugates in CD1 Mouse and Human Plasma:

For studying the stability of the maytansinoids as wells as the maytansinoid-HSA conjugates in CD1 and human plasma the compounds were incubated at 37° C. for 24 hours. Remaining free maytansinoid or release of the respective maytansinoid was quantified by LC-MS/MS (or HPLC) at certain time points.

LC-MS Quantification Procedure:

Pooled CD1 mouse or human plasma ($K_2$EDTA, Innovative research) was centrifuged (1 min at 12,044 g). The supernatant was first filtered through a filter needle (5 µm, sterile, Becton Dickinson) and subsequently through a cellulose acetate membrane (0.45 µm, sterile, Carl Roth). The filtered plasma (1710 µL) was preincubated at 37° C. for 30 min in a heating block. The free maytansinoid or albumin-binding maytansinoid as a 300 µM stock solution in DMSO (190 µL) was added to the preincubated plasma sample to produce a 30 µM solution of the respective maytansinoid or maytansinoid-HSA conjugate. The mixture was allowed to react for 10 min at 37° C. and then at each time point (0, 1, 2, 3, 4, 5, 21, and 24 hours) three samples (70 µL) were taken into a 96-well plate, sealed with a plastic mat, immediately frozen with liquid nitrogen and stored at −20° C. At the end of the experiment, the 96-well plate was thawed at room temperature. The samples (30 µL) were then directly transferred via a multichannel pipette into a 96-well Impact™ protein precipitation plate (Strata®) which was once washed with MeCN (150 µL) and then loaded with the internal standard (120 µL, MeCN containing 5 µg/mL maytansine). The Impact™ precipitation plate was sealed with a silicone mat and shaken for 2 min 420 rpm. The Impact™ precipitation plate was then placed onto a 96-well sample manifold and the filtrate was collected into another 96-well plate by applying mild vacuum. The 96-well plate was sealed with a silicone mat and kept at room temperature until LC-MS/MS quantification. The filtrate was injected into the LC-MS for quantification using the MRM mode.

LC-MS Method:

Phenomenex Luna® Omega Polar C18, 1.6 µm, 100 Å, 50×2.1 mm, column; eluent A (0.1% formic acid in water) and eluent B (0.1% formic acid in MeCN) eluting with a gradient of eluent B (20% 0-0.5 min, flow 0.4 mL/min; 20-60% 0.5-9.0 min, 0.4 mL/min; 60-100% 9.0-9.5 min, flow 0.4 mL/min; 100-20% 9.5-10.5 min, flow 0.4 mL/min; 20% 10.5-12 min, 0.6 mL/min). Column oven temperature 25° C.; autosampler temperature room temperature; 10 µL of injection volume.

The area under the curve (AUC) for each free drug at time point 0 was set as 100% value for the respective prodrug. The AUC for each sample was normalized based on the AUC of maytansine.

HPLC Quantification Procedure:

Samples were prepared as described before using a 2 mM stock solution in DMSO of the free drug as well as the prodrug. After incubation at 37° C. the samples were directly injected into HPLC every hour for a period of 24 hours. The area under the curve (AUC) for each free maytansinoid (200 µM in 10% DMSO in PBS buffer) was used as 100% value for the respective albumin-binding maytansinoid.

HPLC Method:

Phenomenex Aeris WP XB-C18, 3.6 µm, 250×4.6 mm, column; eluent A (20 mM Tris buffer pH 8.0) and eluent B (90:10, MeCN: water) eluting with a gradient of eluent B (25% 0-0.5 min, 25-35% 0.5-2.5 min, 35-85% 2.5-16 min, 85-95% 16-17 min, 95% 17-20 min, 95-25% 20-25 min, 25% 25-30 min, flow rate=1.0 mL/min). Column oven temperature 37° C.; autosampler temperature 37° C.; 20 µL of injection volume.

The relative release of the free maytansinoid as well as the conversion into maytansinol are listed below in Table 5.

TABLE 5

Relative release of the free maytansinoid and/or maytansinol in CD1 mouse and human plasma for the maytansinoid-HSA conjugates

| Albumin-binding maytansinoid (Cmpd) | % of free maytansinoid released after 24 h | | % of maytansinol conversion after 24 h | |
|---|---|---|---|---|
| | CD1 mouse | human | CD1 mouse | human |
| 31 | 3.0 | 6.8 | 2.9 | 2.1 |
| 45 | 6.5 | na | nd | na |
| 34* | 4.3 | na | nd | na |
| 33 | 8.7 | 10.3 | nd | nd |
| 32 | 7.0 | 7.8 | nd | 0.3 |
| 30 | 4.1 | 6.2 | nd | nd |
| 42 | 2.7 | 7.4 | 2.1 | 1.8 |
| 35 | na | 9.0 | na | nd |

*data were obtained by HPLC

The amount of remaining free maytansinoid as well as the conversion into maytansinol are listed below in Table 6.

TABLE 6

Remaining amount of free maytansinoid and maytansinol after 24 h in CD1 mouse and human albumin

| Maytansinoid (Cmpd) | % of free maytansinoid remaining after 24 h | | % of maytansinol conversion after 24 h | |
|---|---|---|---|---|
| | CD1 mouse | human | CD1 mouse | human |
| 4 | 65.2 | 75.6 | 0.5 | nd |
| 2 | 71.8 | 74.8 | nd | nd |
| 3 | 40.8 | 69.6 | 19.1 | 4.5 |

The stability of different linkers with (maytansinoid 4) in CD1 murine plasma is depicted in FIG. 1.

Example 9

In Vitro Binding Kinetics of Albumin-Binding Maytansinoids to Albumin in Pooled Human Whole Blood and Plasma:

To study the binding kinetics of the albumin-binding maytansinoids in pooled human plasma and pooled human whole blood, the compounds were incubated together with pooled human plasma at 37° C. and samples were taken at specified time points. Remaining albumin-binding maytansinoids were quantitated by HPLC.

HPLC Quantification Procedure:

To study the binding kinetics in human whole blood, the blood ($K_2$EDTA, 36 donors, Zen-Bio; 900 µL) was preincubated at 37° C. for 30 min in a heating block. To study the binding kinetics in pooled human plasma, the pooled whole blood was centrifuged (10 min, 1811 g), the supernatant plasma was collected and then preincubated at 37° C. for 30 min.

The albumin-binding maytansinoid was added to the preincubated whole blood/plasma sample as a 10-fold dilution in PBS of a 1.2 mM stock solution in 2.5% propylene glycol in 10 mM sodium phosphate buffer and 1.48 mM citrate (100 µL) to produce a 12.0 µM solution of the respective albumin-binding maytansinoid. Samples (190 µL) were taken after 15 s, 2 min, 4 min, 8 min and 15 min. The samples were directly added to 760 µL MeCN containing maytansine (5 µg/mL) as an internal standard and vortexed for 1 min. After centrifugation (1 min at 12,044 g) the supernatant (850 µL) was concentrated under high vacuum. The residue was taken up in DMSO/water (1:1 v/v; 95 μL) and then analyzed by RP-HPLC. Percentage of binding was determined by comparison of the area under the curve (AUC) at 220 nm of the albumin-binding maytansinoid relative to a control sample (100% value) in PBS buffer. All experiments were performed in triplicates.

HPLC method: Phenomenex Kinetex Polar C18, 2.6 μm, 100 Å, 150×4.6 mm; eluent A (95:5 5 mM ammonium acetate: MeCN) and eluent B (5:95 5 mM ammonium acetate: MeCN) eluting with a gradient of eluent B (30% 0-0.5 min, 30-95% 0.5-9.0 min, 95% 11.0 min, 95-30% 11.0-14.5 min, 30% 15.0 min, flow rate=1.0 mL/min). Column oven temperature ambient temperature; autosampler temperature 4° C.; 50 μL of injection volume.

The relative amount of bound albumin-binding maytansinoid at 0 and 8 min are listed in the table below:

TABLE 7

Amount of bound albumin-binding maytansinoid after 15 s and 8 min in pooled human whole blood and plasma

| Albumin-binding maytansinoid | % bound | | | |
|---|---|---|---|---|
| | plasma | | whole blood | |
| | 15 s | 8 min | 15 s | 8 min |
| 31 | 92.0 ± 7.5 | 98.6 ± 0.1 | 99.2 ± 0.4 | 99.3 ± 0.2 |
| 30 | 96.4 ± 3.6 | 98.5 ± 0.6 | 98.3 ± 0.5 | 98.5 ± 0.6 |

Example 10

In Vitro Cytotoxicity of Maytansine, DM1, DM1-SMe, Maytansinol, and the Maytansinoids in Different Cell Lines Using the CellTiter-Blue® Cell Viability Assay The study tested the in vitro efficacy of all compounds using Promega's CellTiter-Blue® Cell Viability Assay. The cancer cell lines that were tested are: LXFL 529 (large cell lung cancer), RKO (colon cancer), SW-620 (colon cancer), CAL-27 (head & neck cancer), LXFL 1674L (large cell lung cancer), MDA-MB 468 (mammary cancer), SK-OV-3 (ovarian cancer), PAXF 1657 (pancreatic cancer), MCF7 (mammary cancer), COLO 205 (colon cancer), MDA-MB 231 (mammary cancer), BT-474 (mammary cancer), and Hep G2 (liver cancer).

Cells are harvested from exponential phase cultures, counted and plated in 96 well flat-bottom microtiter plates at a cell density depending on the cell line's growth rate (4,000 and 60,000 cells). After a 24 hours recovery period to allow the cells to resume exponential growth, 10 μL of culture medium (four control wells/plate) or of culture medium with the test compound are added.

Figure 2:
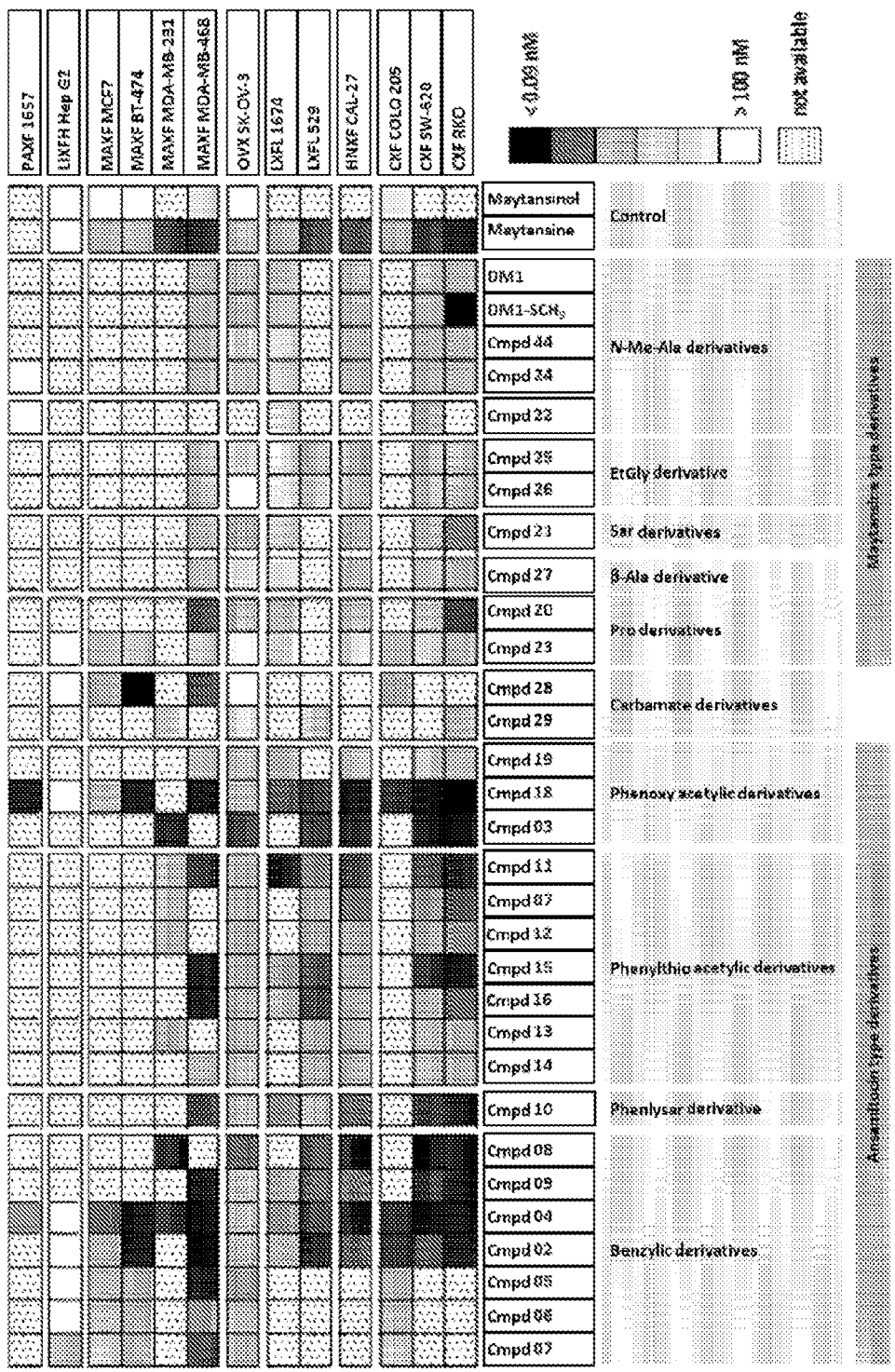
FIG. 2 shows the heat map of geometric mean $IC_{50}$ values in a panel of different cell lines.

Compounds are applied in half-log dilution steps at 10 concentrations in duplicate and cells are treated continuously for 96 h. After treatment and incubation of the cells, 20 μL/well CellTiter-Blue® reagent is added. After incubation of up to 4 hours, fluorescence (FU) is measured by using the EnSpire multilabel reader (excitation=531 nm, emission λ=615 nm). Sigmoidal concentration response curves are fitted to the data points (T/C values) obtained for each cell line using 4 parameter non-linear curve fit (Oncotest Warehouse Software). $IC_{50}$ values are reported as relative $IC_{50}$ values, being the concentration of test compound that give a response (inhibition of colony formation/viability) half way between the top and bottom plateau of the sigmoidal concentration response curve (inflection point of the curve), or as absolute $IC_{50}$ values, being the concentration of test compound at the intersection of the concentration-response curves with T/C=50%. For calculation of mean $IC_{50}$ values the geometric mean is used. Results are presented as mean graph plots or heat maps (individual $IC_{50}$ values relative to the geometric mean $IC_{50}$ value) over all cell lines as tested. See Table 8 and FIG. 2. FIG. 2 shows the heat map of $IC_{50}$ for all tested compounds.

TABLE 8

| | Geomean $IC_{50}$ [nM] | n Cell Lines |
|---|---|---|
| DM1 | 3.22 | 6 |
| DM1-SMe | 1.30 | 6 |
| 18 | 0.13 | 12 |
| 24 | 9.04 | 7 |
| 44 | 7.21 | 6 |
| 4 | 0.16 | 13 |
| 2 | 0.30 | 11 |
| 5 | 0.90 | 6 |
| 6 | 2.14 | 6 |
| 28 | 10.6 | 6 |
| 20 | 0.94 | 6 |
| 7 | 0.89 | 6 |
| 23 | 26.80 | 10 |
| 21 | 1.67 | 6 |
| 22 | 25.00 | 3 |
| 19 | 1.12 | 6 |
| 9 | 0.19 | 7 |
| 17 | 0.45 | 6 |
| 15 | 0.18 | 7 |
| 16 | 0.32 | 7 |
| 14 | 1.54 | 6 |
| 3 | 0.10 | 6 |
| 8 | 0.10 | 6 |
| 48 | 59.90 | 6 |
| Maytansine | 0.22 | 12 |
| Maytansinol | 86.00 | 6 |
| 27 | 11.70 | 6 |
| 46 | 67.80 | 6 |
| 11 | 0.21 | 8 |
| 25 | 8.47 | 7 |
| 10 | 0.30 | 7 |
| 47 | 10.70 | 7 |
| 26 | 18.50 | 7 |
| 12 | 0.76 | 6 |
| 13 | 0.88 | 6 |

Example 11

General Procedure for the Evaluation of Maytansine and the Albumin-Binding Maytansinoid Compounds in a Patient-Derived Tumor Xenograft Model Female immunodeficient NMRI nude mice, from Charles River, received unilateral tumor implants subcutaneously in the left flank while under isoflurane anesthesia with human cancer tumors until tumors were palpable and had reached a volume of 80-200 mm³ (unless otherwise stated).

Animals were kept in cages, the temperature inside the cages maintained at 25±1° C. with a relative humidity of 45-65% and an air change rate in the cage of 60-fold per hour. They were kept under a 14 h light: 10 h dark, artificial light cycle. The animals were fed with autoclaved Teklad Global 19% Protein Extruded Diet (T.2019S.12) from Envigo RMS SARL and had access to sterile filtered and acidified (pH 2.5) tap water, which was changed twice weekly. Feed and water were provided ad libitum. Prior to therapy, the animals were randomized (7 mice per group, unless otherwise stated) considering a comparable median and mean of group tumor volume. Animals were routinely monitored twice daily on working days and daily on Saturdays and Sundays. Starting on day 0, animals were weighed twice a week. Relative body weights (RBW) of individual animals were calculated by dividing the individual absolute body weight on day X ($BW_x$) by the individual body weight on the day of randomization multiplied by 100%. The tumor volume was determined by a two-dimensional measurement with calipers on the day of randomization (day 0) and then twice weekly. Tumor volumes were calculated according to the following equation: Tumor Vol $[mm^3]=1$ $[mm] \times w^2$ $[mm^2] \times 0.5$, where "1" is the length and "w" is width of the tumor. The relative volume of an individual tumor on day X (RTVx) was calculated by dividing the absolute individual tumor volume $[mm^3]$ of the respective tumor on day X (Tx) by the absolute individual tumor volume of the same tumor on the day of randomization multiplied by 100%. Schedules were applied to the extent that animal welfare policies allow. Termination of individual mice was carried out at tumor volume>2000 $mm^3$ (unilateral). All test compounds were administered on day 1, 8, 15, and 22 and were supplied as lyophilized solids containing sucrose. On the day of treatment, the lyophilized samples were dissolved in 10 mM sodium phosphate buffer pH 6.8, containing 20% propylene glycol and injected intravenously (100 µL/20-g mouse) together with vehicle (10 mM sodium phosphate buffer, 20% propylene glycol, and 5% sucrose—pH 6.8).

Example 12

General Procedure for the Evaluation of Maytansine and the Albumin-Binding Maytansinoid Compounds in a Cancer Cell-Line-Derived Xenograft Model Female immunodeficient NMRI nude mice, from Janvier, France, received $5 \times 10^6$ cultured cancer cells in buffer/Matrigel (1:1) transplant subcutaneously (unless otherwise stated) until tumors were palpable and had reached a volume of 80-200 $mm^3$ (unless otherwise stated). Animals were kept in cages, the temperature inside the cages maintained at 22±1° C. with a relative humidity of 50±10% and an air change rate in the cage of 60-fold per hour. They were kept under a 12 h light: 12 h dark, artificial light cycle. The animals were fed with autoclaved Ssniff NM, from Ssniff® and had access to sterile filtered and acidified (pH 4.0) tap water, which was changed twice weekly. Feed and water were provided ad libitum. Prior to therapy, the animals were randomized (7 mice per group, unless otherwise stated) considering a comparable median and mean of group tumor volume. Animals were routinely monitored twice daily on working days and daily on Saturdays and Sundays. Starting on day 0, individual body weights of mice were determined two or three times per week and mean body weight per group was related to the initial value in percent to calculate the body weight change (BWC). The tumor volume was determined by a two-dimensional measurement with calipers on the day of randomization (day 0) and then twice or three times per week. Tumor volumes were calculated according to the following equation:

Tumor Vol $[mm^3]=1$ $[mm] \times w^2$ $[mm^2] \times 0.5$, where "1" is the length and "w" is width of the tumor. The relative volume of an individual tumor on day X (RTVX) was calculated by dividing the absolute individual tumor volume $[mm^3]$ of the respective tumor on day X (Tx) by the absolute individual tumor volume of the same tumor on the day of randomization multiplied by 100%. Schedules were applied to the extent that animal welfare policies allow. Termination of individual mice was carried out at tumor volume>1500 $mm^3$ (unilateral) or ulceration was observed. All test compounds were administered on day 1, 8, 15, and 22 and were supplied as lyophilized solids containing sucrose. On the day of treatment, the lyophilized samples were dissolved in 10 mM sodium phosphate buffer pH 6.8, containing 20% propylene glycol and injected intravenously (100 µL/20-g mouse) together with vehicle (10 mM sodium phosphate buffer, 20% propylene glycol, and 5% sucrose—pH 6.8).

Example 13

Evaluation of Maytansine and the Albumin-Binding Maytansinoids 30, 42, 31 and 35 in the Human PDX Renal Cell Cancer Model RXF 631

Figure 3:
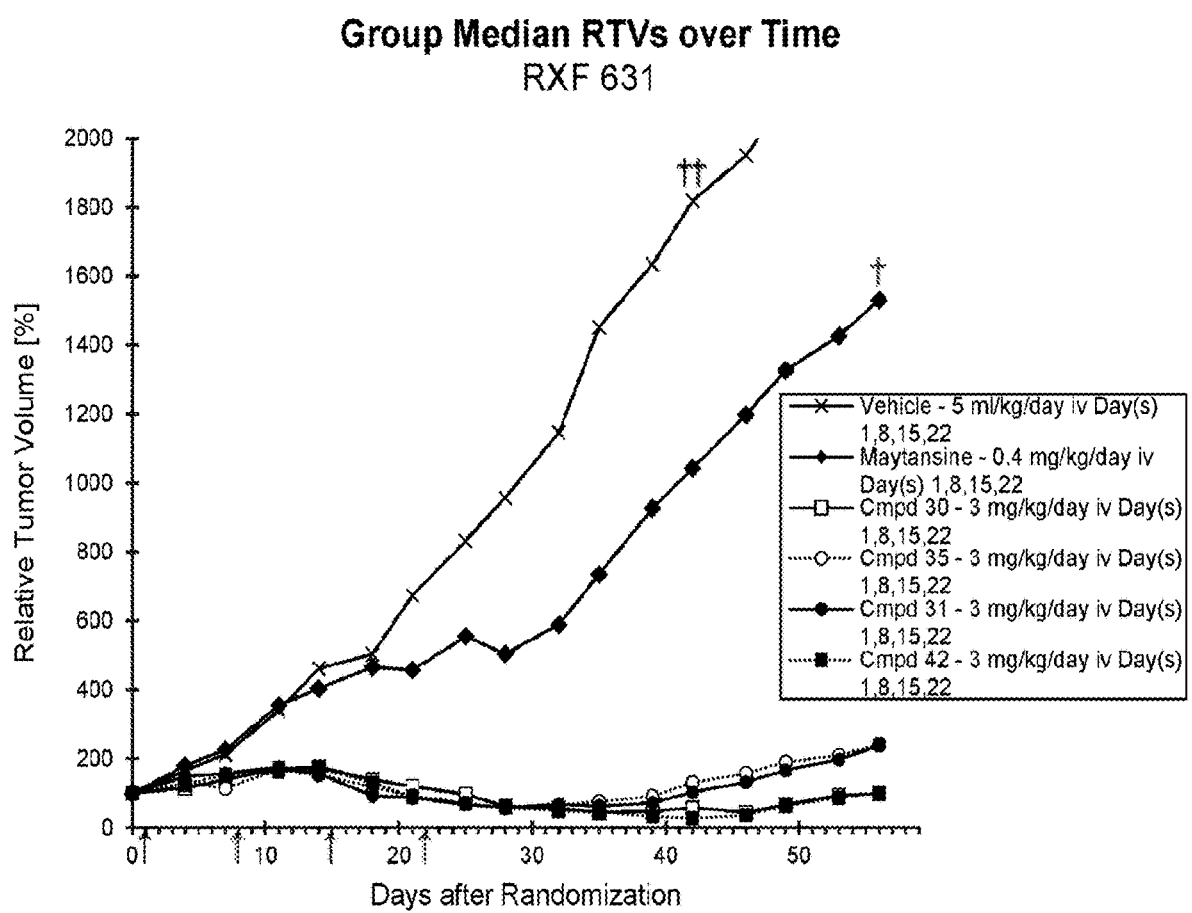
FIG. 3 shows tumor growth curves of the control group, maytansine group, and the groups treated with compounds 30, 42, 31 and 35 in the RXF631 renal cell tumor model.
Figure 4:
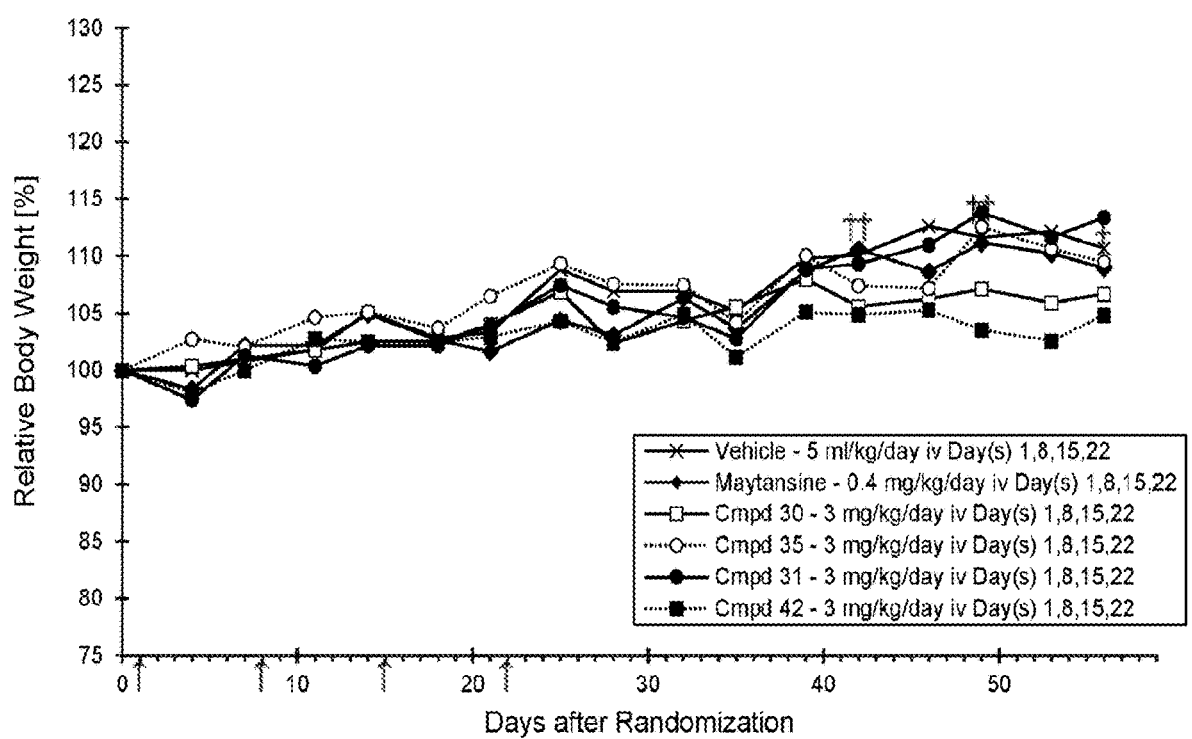
FIG. 4 shows curves of body weight change in the control group, maytansine group, and the groups treated with compounds 30, 42, 31 and 35 in the RXF631 renal cell tumor model.

The evaluation of maytansine and the albumin-binding compounds 30, 42, 31 and 35 in the renal cancer cell RXF 631 model was carried out according to the general procedure for a patient-derived xenograft model. Treatment was initiated after tumors reaching an average size of 100 $mm^3$. FIG. 3 shows tumor growth curves of the control group, maytansine group, and the groups treated with compounds 30, 42, 31 and 35. FIG. 4 shows curves of body weight change in the control group, maytansine group, and the groups treated with compounds 30, 42, 31 and 35.

Example 14

Evaluation of Maytansine and the Albumin-Binding Maytansinoids 32, 30, and 31 in the Human PDX Squamous Cell Lung Cancer Model LXFE 937

Figure 5:
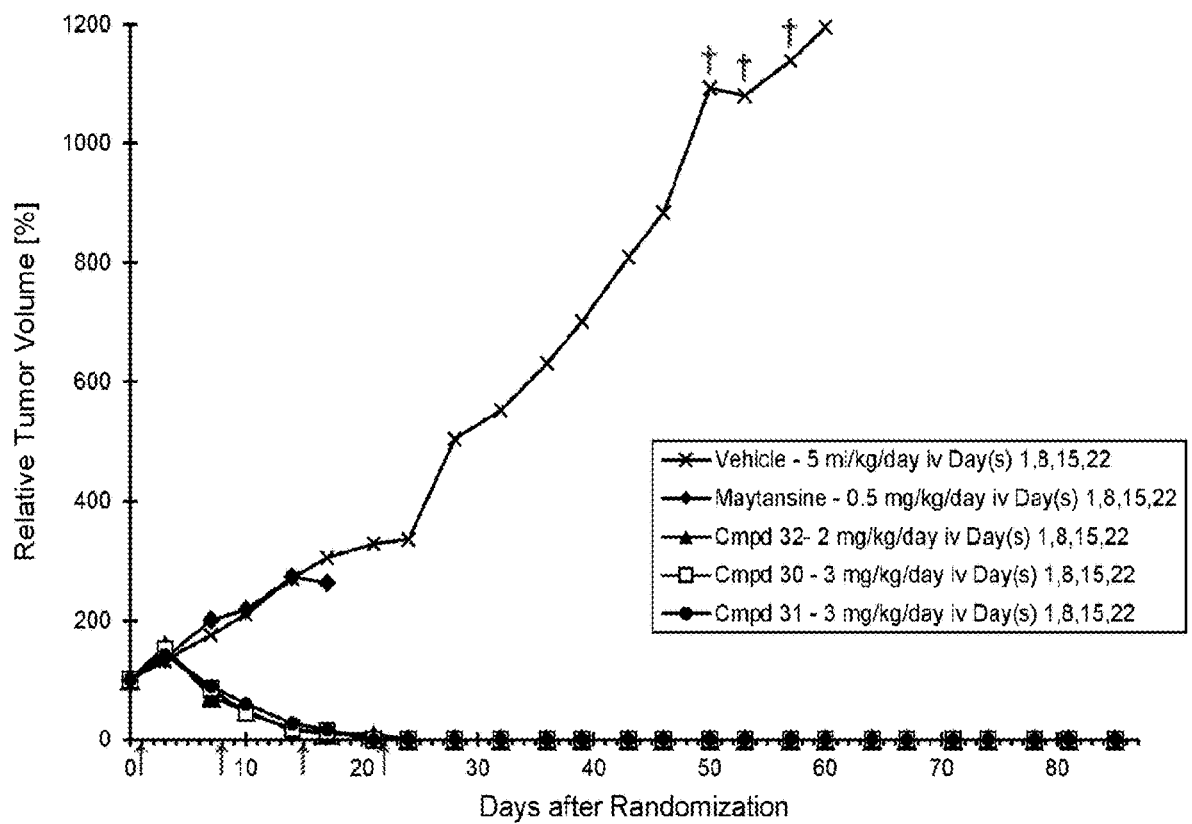
FIG. 5 shows tumor growth curves of the control group, maytansine group, and the groups treated with compounds 32, 30, and 31 in the LXFE 937 squamous cell lung carcinoma model.
Figure 6:
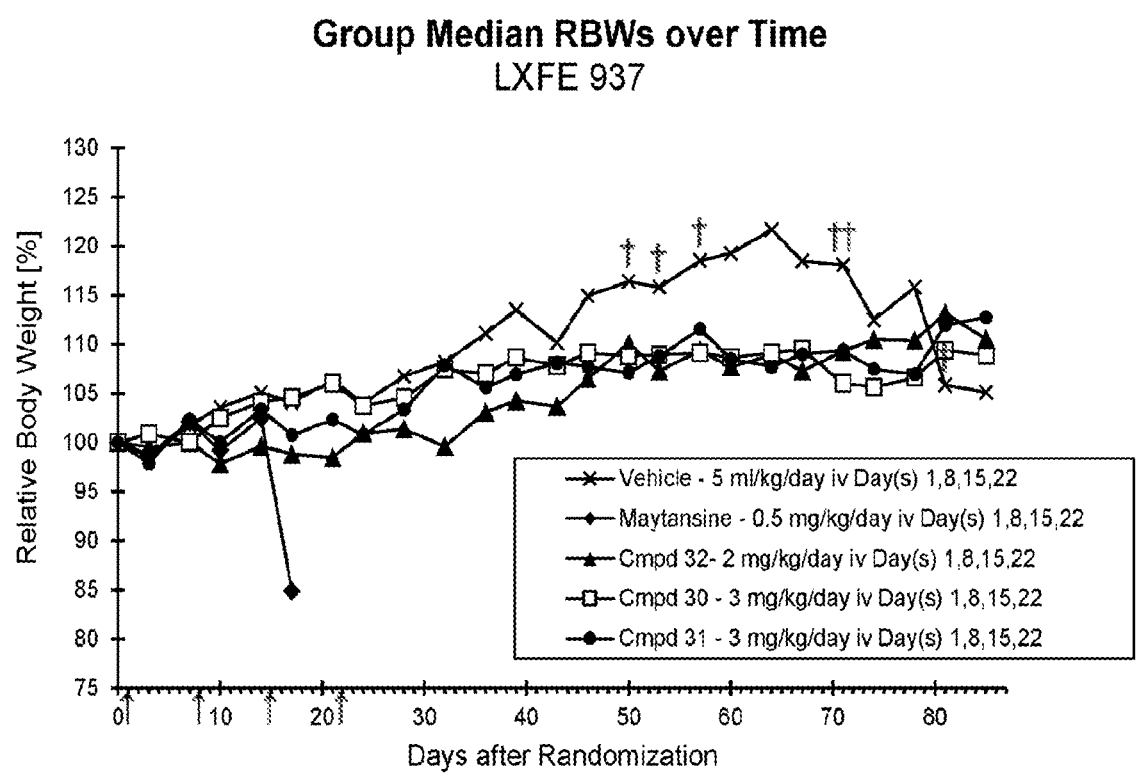
FIG. 6 shows curves of body weight change in the control group, maytansine group, and the groups treated with compounds 32, 30, and 31 in the LXFE 937 squamous cell lung carcinoma model.

The evaluation of maytansine and the albumin-binding compounds 32, 30, and 31 in the squamous cell lung cancer LXFE 937 model was carried out according to the general procedure for a patient-derived xenograft model. Treatment was initiated after tumors reaching an average size of 117 $mm^3$. FIG. 5 shows tumor growth curves of the control group, maytansine group, and the groups treated with compounds 32, 30, and 31. FIG. 6 shows curves of body weight change in the control group, maytansine group, and the groups treated with compounds 32, 30, and 31.

Example 15

Evaluation of Maytansine and the Albumin-Binding Maytansinoids 30 and 31 in the Human PDX Squamous Cell Lung Cancer Model LXFE 937 (Large Tumors)

Figure 7:
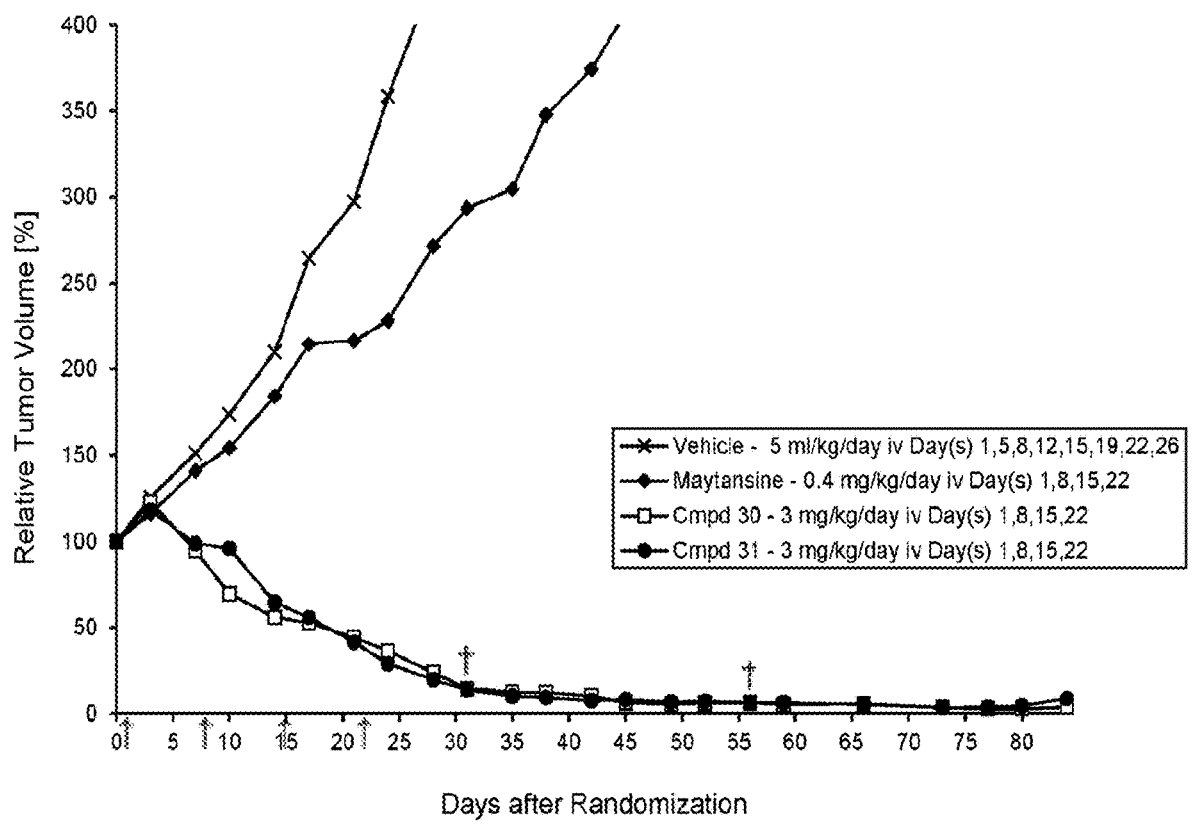
FIG. 7 shows tumor growth curves of the control group, maytansine group, and the groups treated with compounds 30 and 31 in the LXFE 937 squamous cell lung carcinoma model.
Figure 8:
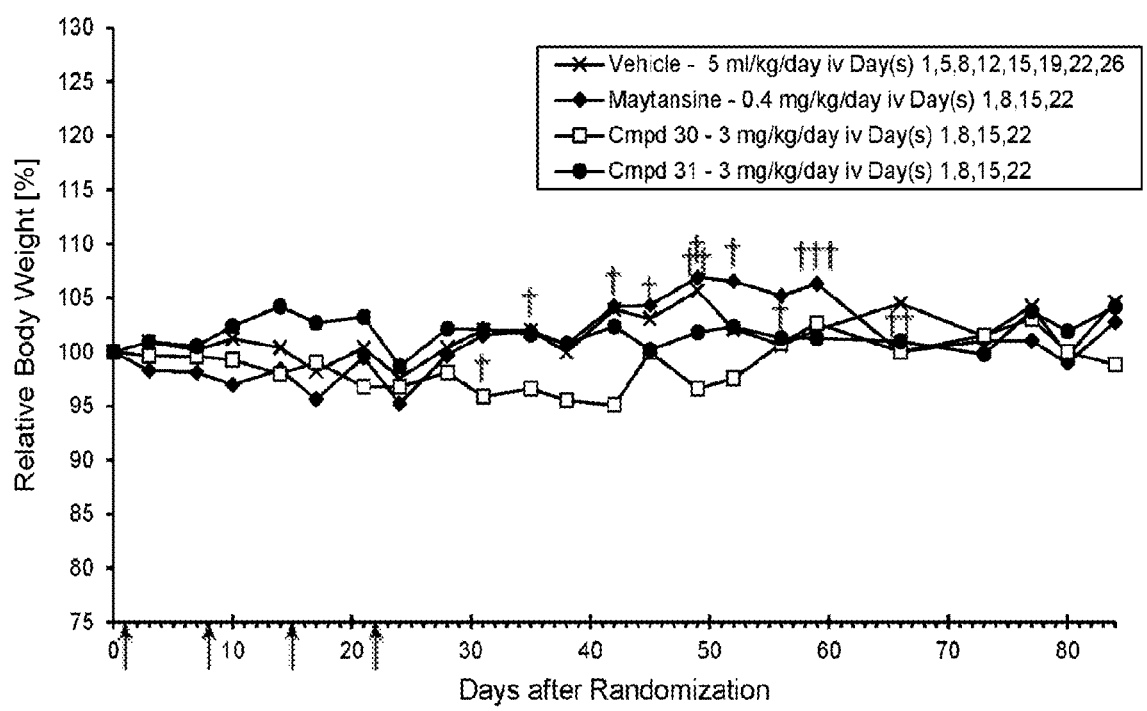
FIG. 8 shows curves of body weight change in the control group, maytansine group, and the groups treated with compounds 30 and 31 in the LXFE 937 squamous cell lung carcinoma model.

The evaluation of maytansine and the albumin-binding compounds 30 and 31 in the squamous cell lung cancer LXFE 937 model was carried out according to the general procedure for a patient-derived xenograft model. Treatment was initiated after tumors reaching an average size of 270 $mm^3$. FIG. 7 shows tumor growth curves of the control group, maytansine group, and the groups treated with compounds 30 and 31. FIG. 8 shows curves of body weight change in the control group, maytansine group, and the groups treated with compounds 30 and 31.

Example 16

Evaluation of Maytansine and the Albumin-Binding Maytansinoids 30 and 31 in the Human PDX Lung Adenocarcinoma Model LXFA 737

Figure 9:
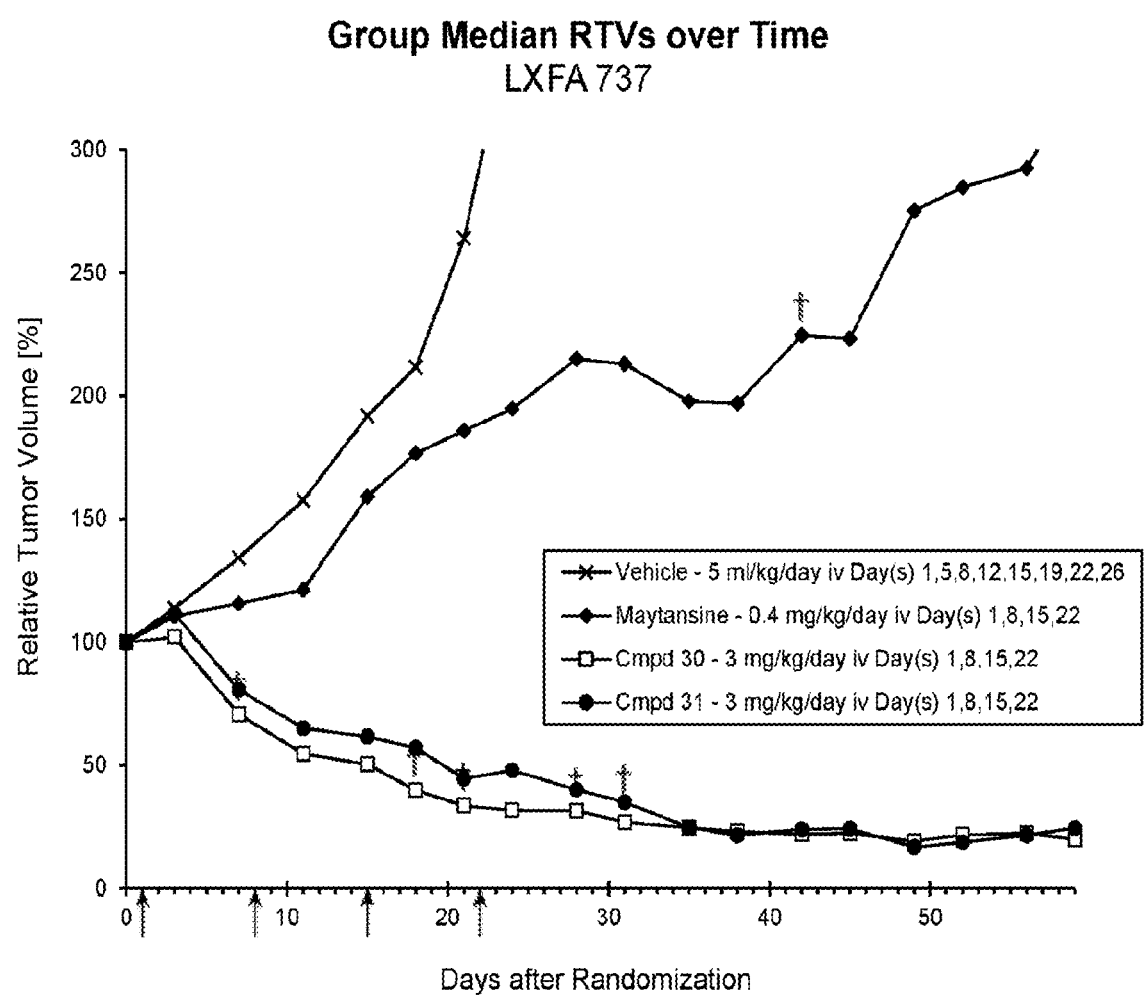
FIG. 9 shows tumor growth curves of the control group, maytansine group, and the groups treated with compounds 30 and 31 in the LXFA 737 lung adenocarcinoma model.
Figure 10:
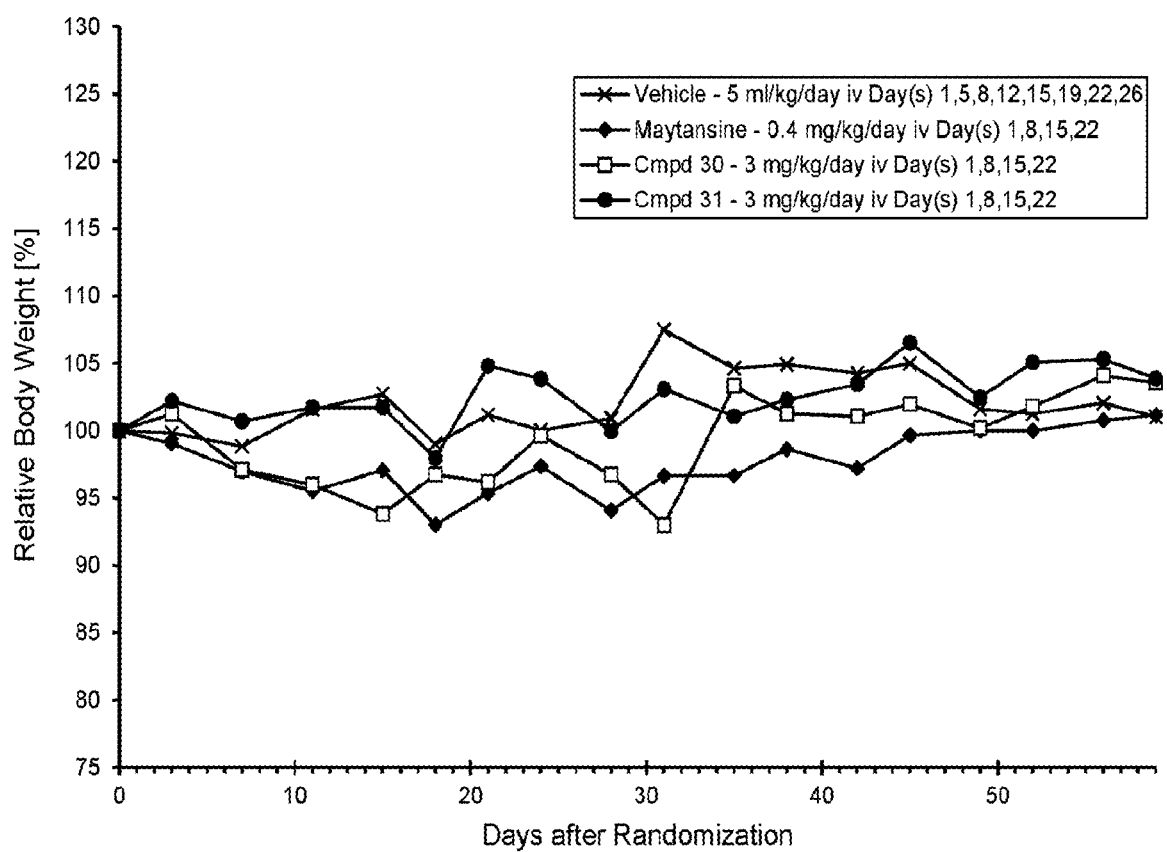
FIG. 10 shows curves of body weight change in the control group, maytansine group, and the groups treated with compounds 30 and 31 in the LXFA 737 lung adenocarcinoma model.

The evaluation of maytansine and the albumin-binding compounds 30 and 31 in the lung adenocarcinoma LXFA 737 model was carried out according to the general procedure for a patient-derived xenograft model. Treatment was initiated after tumors reaching an average size of 311 $mm^3$. FIG. 9 shows tumor growth curves of the control group, maytansine group, and the groups treated with compounds 30 and 31. FIG. 10 shows curves of body weight change in the control group, maytansine group, and the groups treated with compounds 30 and 31.

Example 17

Evaluation of Maytansine and the Albumin-Binding Maytansinoids 32, 30 and 31 in the Human Xenograft Breast Carcinoma Model MDA-MB-231

Figure 11:
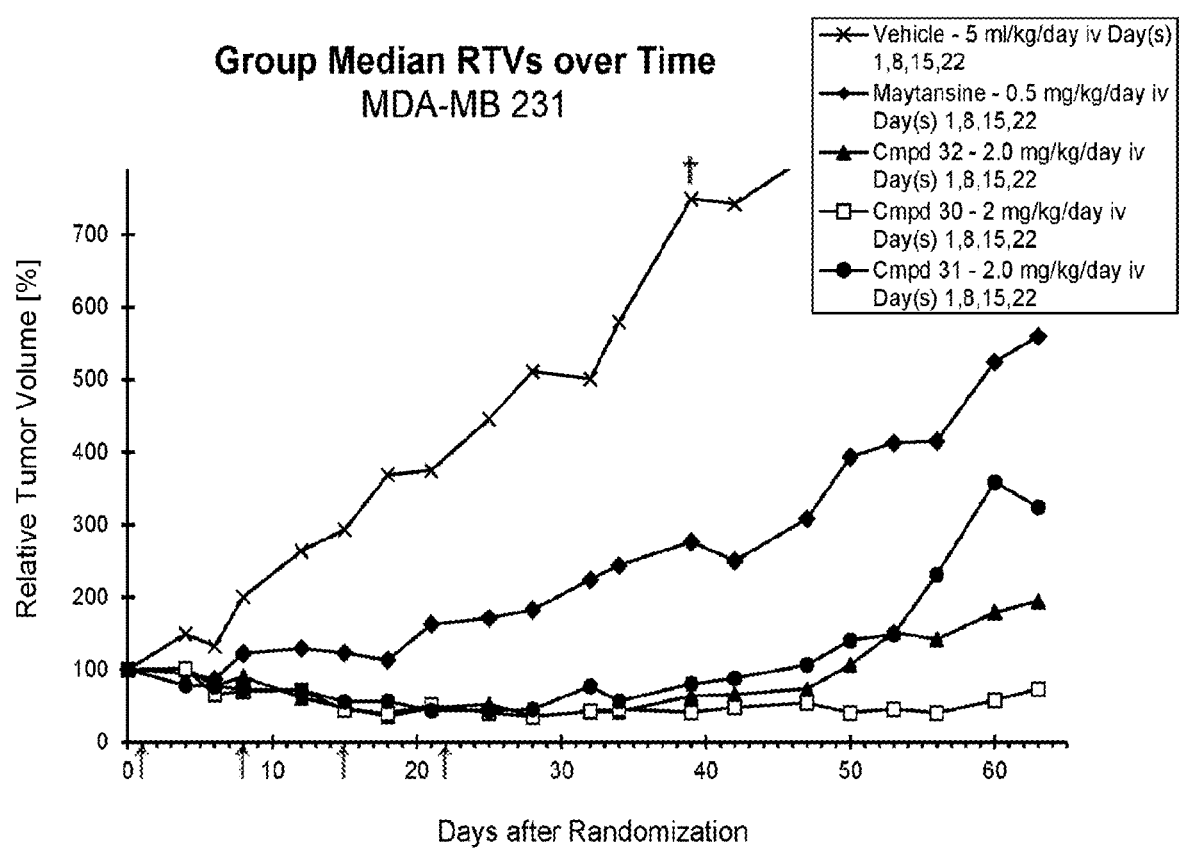
FIG. 11 shows tumor growth curves of the control group, maytansine group, and the groups treated with compounds 32, 30, and 31 in the MDA-MB 231 breast cancer model.
Figure 12:
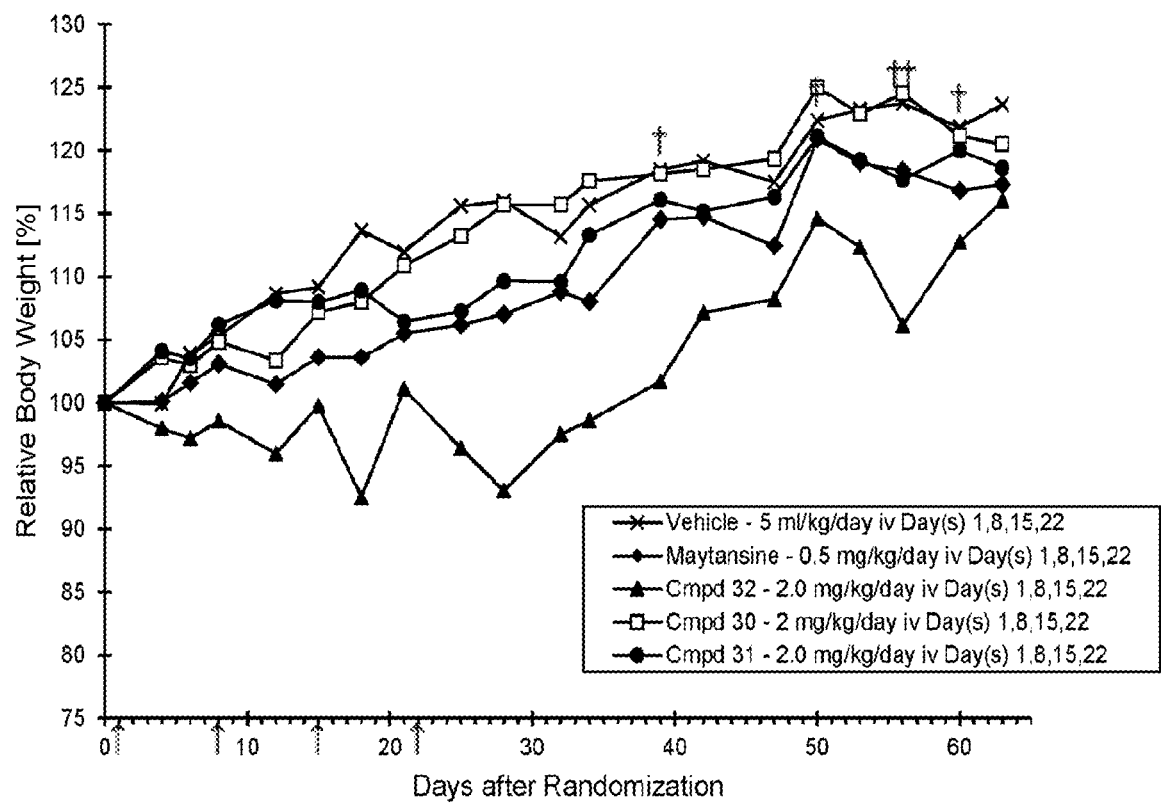
FIG. 12 shows curves of body weight change in the control group, maytansine group, and the groups treated with compounds 32, 30, and 31 in the MDA-MB 231 breast cancer model.

The evaluation of maytansine and the albumin-binding compounds 32, 30 and 31 in the MDA-MB 231 breast carcinoma model was carried out according to the general procedure for a cancer cell-line-derived xenograft model. Treatment was initiated after tumors reaching an average size of 80 mm³. FIG. 11 shows tumor growth curves of the control group, maytansine group, and the groups treated with compounds 32, 30, and 31. FIG. 12 shows curves of body weight change in the control group, maytansine group, and the groups treated with compounds 32, 30, and 31.

Example 18

Evaluation of Maytansine and the Albumin-Binding Maytansinoids 30 and 31 in a Human Xenograft Ovarian Cancer Model A2780

Figure 13:
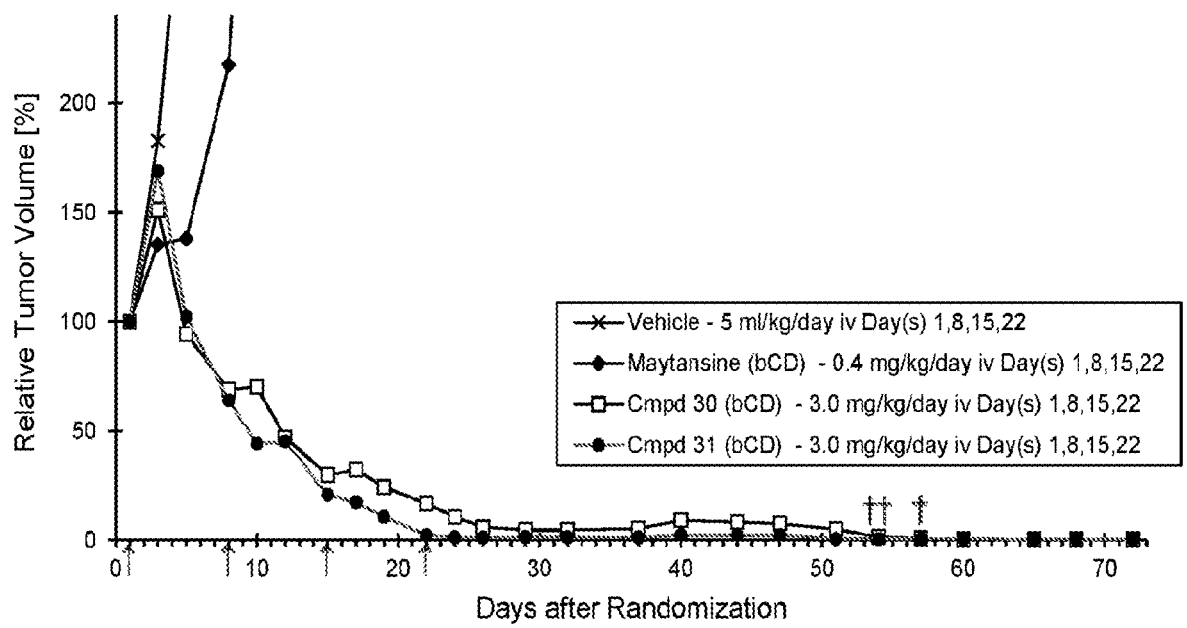
FIG. 13 shows tumor growth curves of the control group, maytansine group, and the groups treated with compounds 30 and 31 in the A2780 ovarian cancer model.
Figure 14:
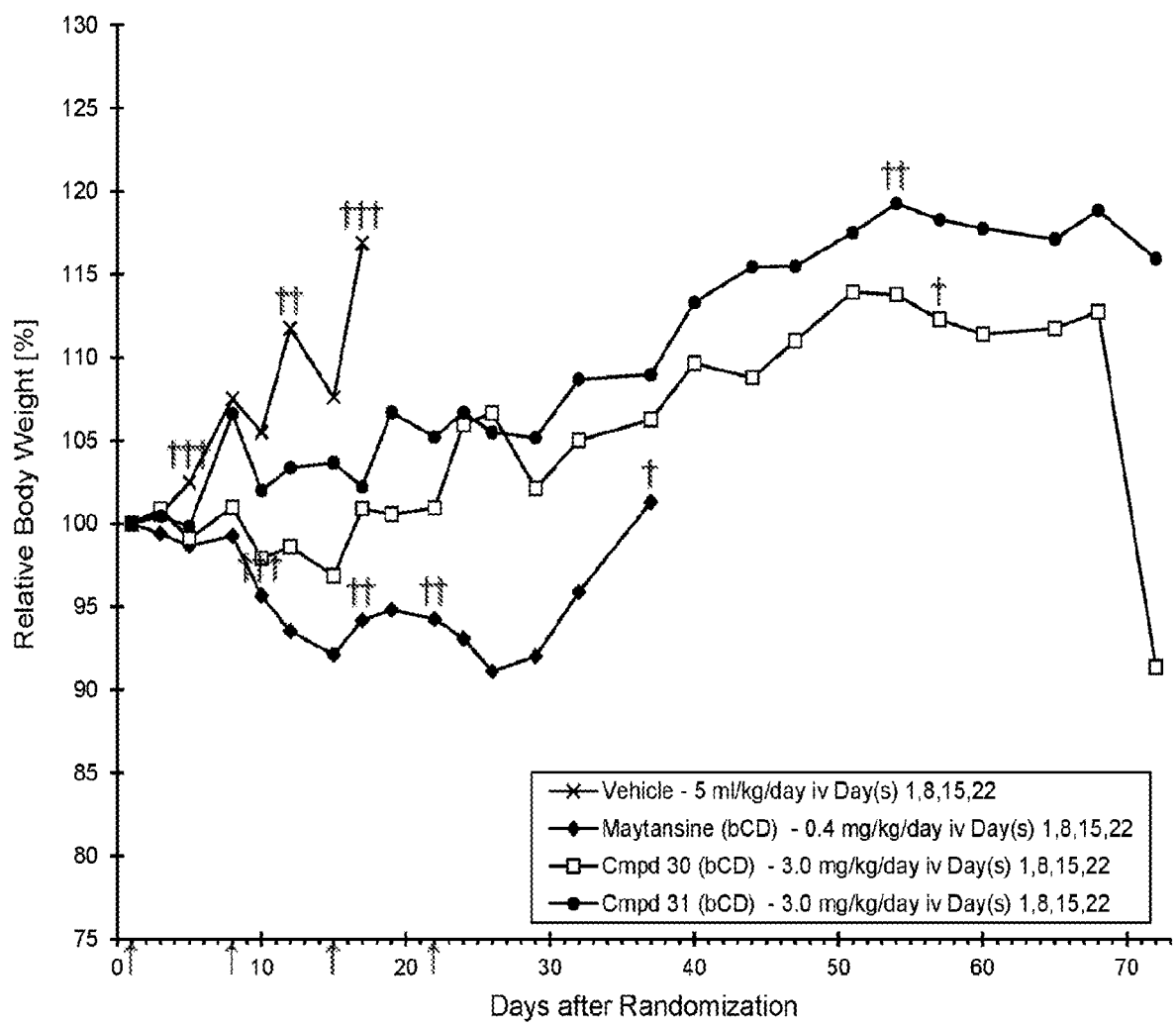
FIG. 14 shows curves of body weight change in the control group, maytansine group, and the groups treated with compounds 30 and 31 in the A2780 ovarian cancer model.

The evaluation of maytansine and the albumin-binding compounds 30 and 31 in ovarian cancer A2780 model was carried out according to the general procedure for a cancer cell-line-derived xenograft model. Treatment was initiated after tumors reaching an average size of 380 mm³. FIG. 13 shows tumor growth curves of the control group, maytansine group, and the groups treated with compounds 30 and 31. FIG. 14 shows curves of body weight change in the control group, maytansine group, and the groups treated with compounds 30 and 31.

Example 19

Evaluation of Maytansine and the Albumin-Binding Maytansinoids 30 and 31 in the Human Xenograft Breast Carcinoma Model MDA-MB 468

Figure 15:
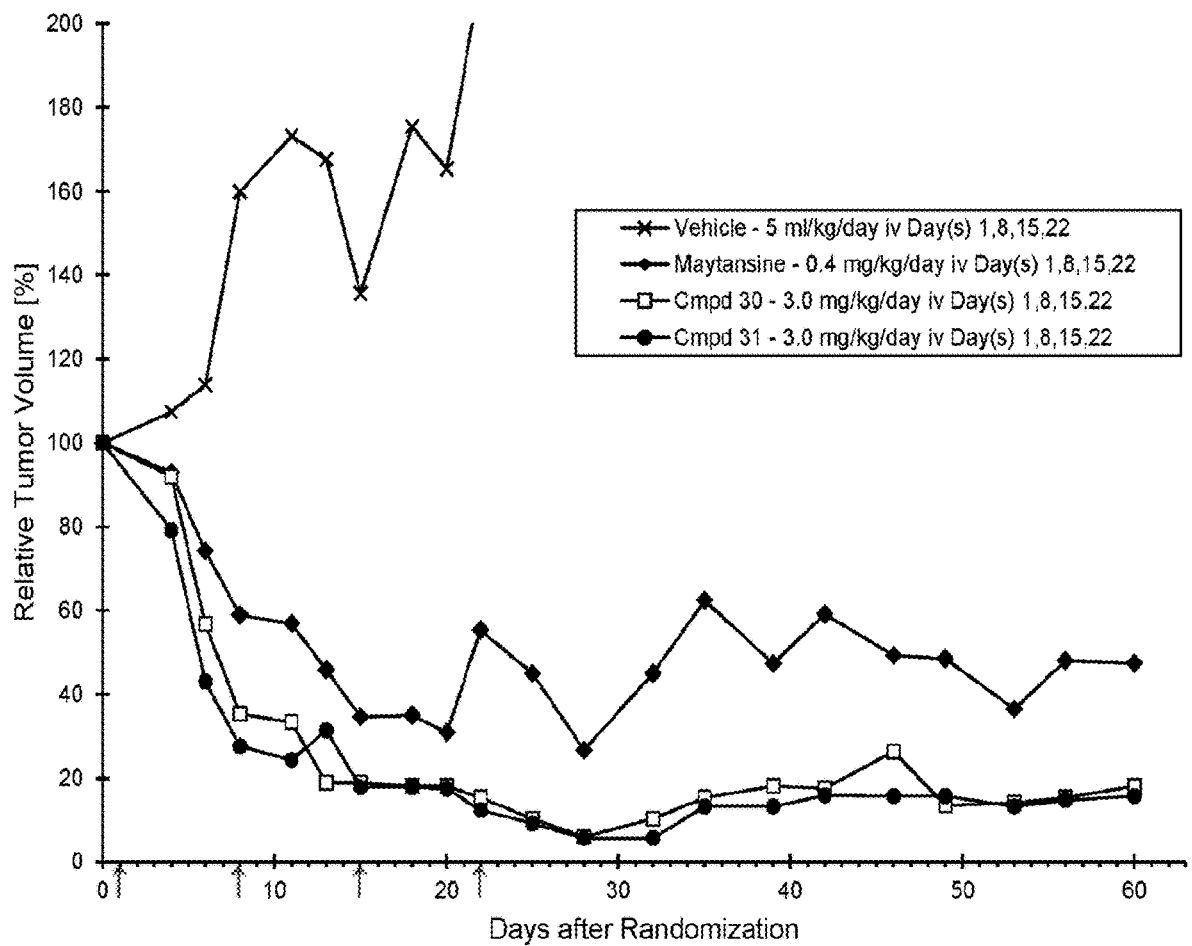
FIG. 15 shows tumor growth curves of the control group, maytansine group, and the groups treated with compounds 30 and 31 in the MDA-MB 468 breast cancer model.
Figure 16:
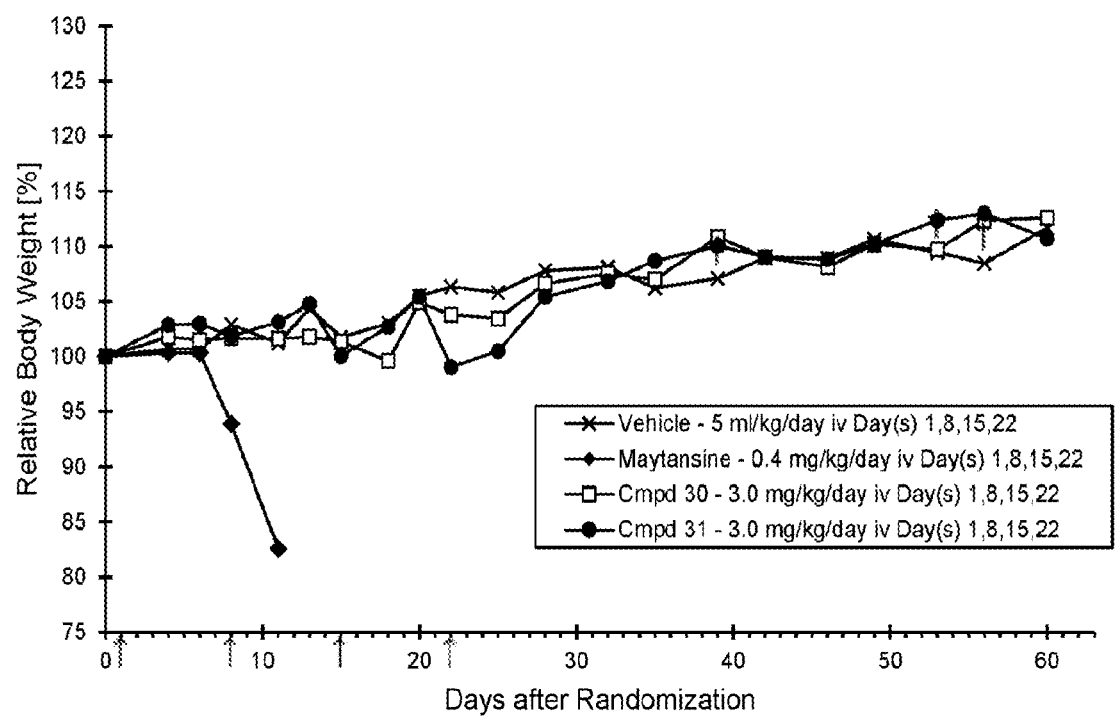
FIG. 16 shows curves of body weight change in the control group, maytansine group, and the groups treated with compounds 30 and 31 in the MDA-MB 468 breast cancer model.

The evaluation of maytansine and the albumin-binding compounds 30 and 31 in breast carcinoma MDA-MB 468 model was carried out according to the general procedure for a cancer cell-line-derived xenograft model. Treatment was initiated after tumors reaching an average size of 94 mm³. FIG. 15 shows tumor growth curves of the control group, maytansine group, and the groups treated with compounds 30 and 31. FIG. 16 shows curves of body weight change in the control group, maytansine group, and the groups treated with compounds 30 and 31.

What is claimed is:
1. A compound having the structure of Formula (I):

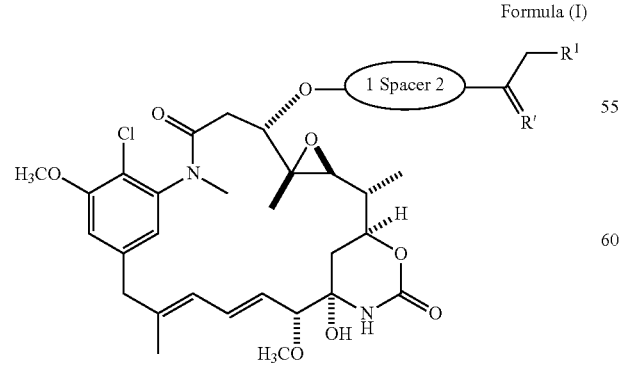

Formula (I)

or a pharmaceutically acceptable salt, hydrate, or isomer thereof, wherein:
$R^1$ is selected from —H and $C_1$-$C_4$ alkyl;
Spacer is selected from:

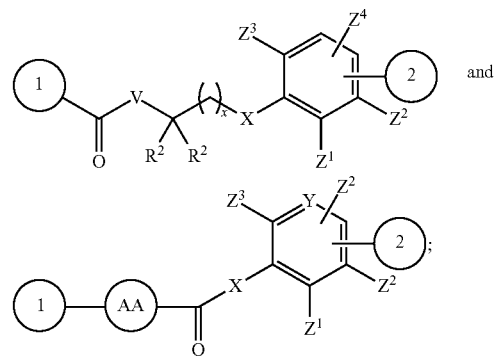

V is absent or selected from —$CH_2$—, —O— and —$NR^3$—, wherein $R^3$ is —H or $C_1$-$C_4$ alkyl; each $R^2$ is independently selected from —H, halogen, and $C_1$-$C_4$ alkyl or two $R^2$s taken together form a $C_3$-$C_6$, cycloalkyl;
n is 0-3;
X is absent or selected from —$CH_2$—, —O—, —S—, —Se—, and —$NR^4$—, wherein $R^4$ is —H or $C_1$-$C_4$ alkyl;
Y is selected from =CH— and =N—;
$Z^1$, $Z^2$, $Z^3$ and $Z^4$ are each independently selected from —H, halogen, —$CF_3$, —$OCH_3$, —CN, —$NO_2$, $C_1$-$C_4$ alkyl and $C_2$-$C_4$ alkoxy;
AA is an amino acid selected from glycine, D or L proline, sarcosine, N-ethyl-glycine, D or L alanine, D or L N-methylalanine, β-alanine, N-methyl-β-alanine, α-aminoisobutyric acid, and N-methyl-α-aminoisobutyric acid;
R' is selected from O and

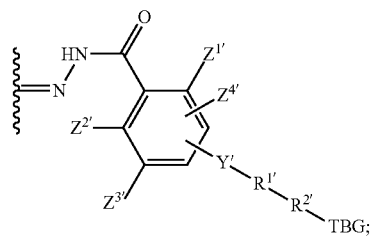

Y' is absent or selected from an optionally substituted $C_1$-$C_6$ alkyl, —NH—C(O)—, and —C(O)—NH—; or Y' is selected from the group consisting of:

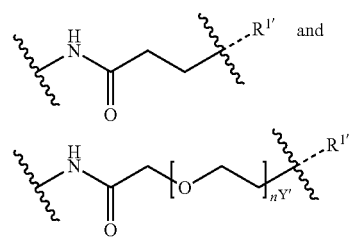

wherein $n^{Y'}$=0-6;

$R^{1'}$ is absent or selected from the group consisting of:

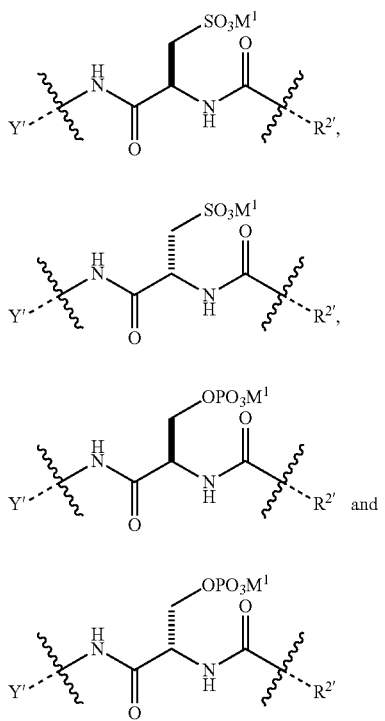

wherein $M^1$ is a pharmaceutically acceptable counter ion selected from the group consisting of $H^+$, $Na^+$, $K^+$, $Ca^{2+}$, $Mg^{2+}$, $NR_4^+$, and $NHR_3^+$; wherein R is H or $C_1$-$C_4$ alkyl;

$R^{2'}$ is optionally substituted $C_1$-$C_{18}$ alkyl wherein optionally up to six carbon atoms in said $C_1$-$C_{18}$ alkyl are each independently replaced with —OCH$_2$CH$_2$—;

$Z^{1'}$, $Z^{2'}$, $Z^{3'}$ and $Z^{4'}$ are each independently selected from —H, halogen, —CF$_3$, —OCH$_3$, —CN, —NO$_2$, —SO$_3$M$^2$, and $C_1$-$C_4$ alkyl wherein $M^2$ is a pharmaceutically acceptable counter ion selected from the group consisting of $H^+$, $Na^+$, $K^+$, $Ca^{2+}$, $NR_4^+$, and $NHR_3^+$;

wherein R is H or $C_1$-$C_4$ alkyl;

TBG is a thiol-binding group selected from an optionally substituted maleimide group, an optionally substituted haloacetamide group, an optionally substituted haloacetate group, an optionally substituted pyridylthio group, an optionally substituted isothiocyanate group, an optionally substituted vinylcarbonyl group, an optionally substituted aziridine group, an optionally substituted disulfide group, an optionally substituted acetylene group, and an optionally substituted N-hydroxysuccinimide ester group;

wherein said TBG is optionally bound to a thiol-bearing macromolecular carrier or thiol-bearing tumor-specific carrier.

2. The compound according to claim 1, wherein the compound has a structure of Formula (II):

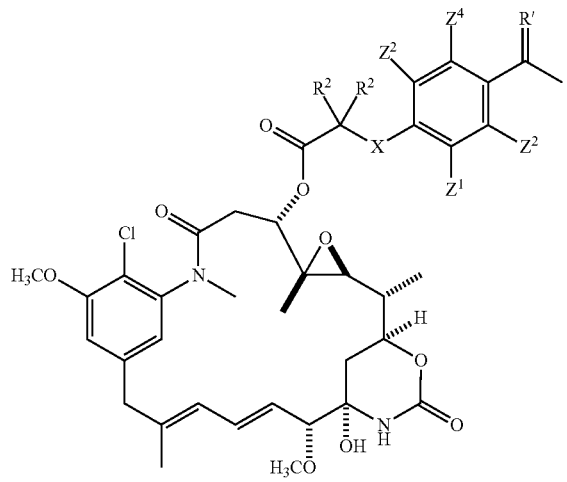

Formula (II)

or a pharmaceutically acceptable salt, hydrate, or isomer thereof,
wherein:
each $R^2$ is independently selected from —H, and $C_1$-$C_4$ alkyl or two $R^2$s taken together form a $C_3$-$C_6$, cycloalkyl;

X is absent or selected from —CH$_2$—, —O—, —S— and —NR$^4$—, wherein $R^4$ is —H or $C_1$-$C_4$ alkyl;

$Z^1$, $Z^2$, $Z^3$ and $Z^4$ are each independently selected from —H, halogen, —CF$_3$, —OCH$_3$, —NO$_2$ and —CH$_3$.

3. The compound according to claim 1, wherein the compound has a structure of Formula (III):

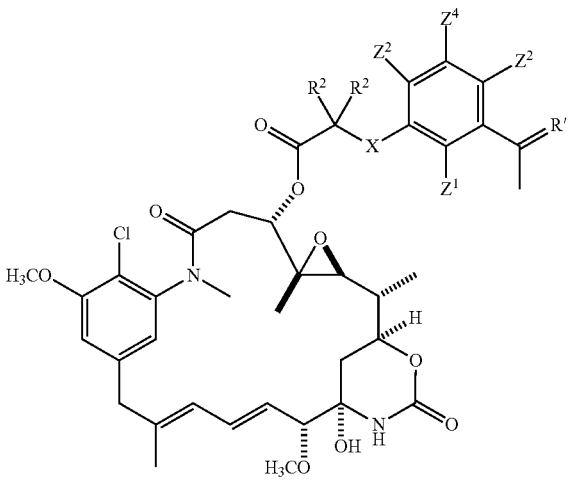

Formula (III)

or a pharmaceutically acceptable salt, hydrate, or isomer thereof,
wherein:
each $R^2$ is independently selected from —H, and $C_1$-$C_4$ alkyl or two $R^2$s are taken together form a $C_3$-$C_6$, cycloalkyl;

X is absent or selected from —CH$_2$—, —O—, —S— and —NR$^4$—, wherein $R^4$ is —H or $C_1$-$C_4$ alkyl;

$Z^1$, $Z^2$, $Z^3$ and $Z^4$ are each independently selected from —H, halogen, —CF$_3$, —OCH$_3$, —NO$_2$ and —CH$_3$.

4. The compound according to claim 1, wherein the compound has a structure of Formula (IV):

Formula (IV)

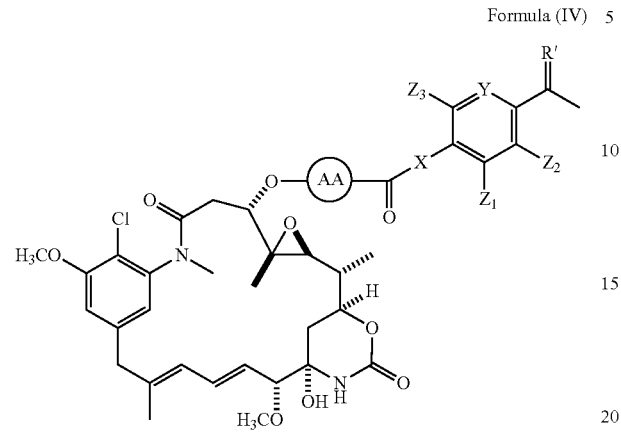

or a pharmaceutically acceptable salt, hydrate, or isomer thereof, wherein:

X is absent or selected from —CH$_2$— and —NH—;

Y is =CH— or =N—;

Z$^1$, Z$^2$, and Z$^3$ are each independently selected from —H, halogen, —CF$_3$, —OCH$_3$, —NO$_2$ and —CH$_3$;

AA is an amino acid selected from glycine, D or L proline, sarcosine, N-ethyl-glycine, D or L alanine, D or L N-methylalanine, β-alanine, N-methyl-β-alanine, α-aminoisobutyric acid, and N-methyl-α-aminoisobutyric acid.

5. The compound according to claim 1, wherein R$^1$ is —H.

6. The compound according to claim 1, wherein at least one of Z$^1$, Z$^2$, Z$^3$, and Z$^4$ is not H.

7. The compound according to claim 1, wherein at least one of Z$^1$, Z$^2$, Z$^3$ and Z$^4$ is —F or —NO$_2$.

8. The compound according to claim 1, wherein n is 0 and X is absent.

9. The compound according to claim 1, wherein n is 0 and X is —CH$_2$—.

10. The compound according to claim 1, wherein n is 0 and X is —O— or —S—.

11. The compound according to claim 1, wherein the compound is selected from:

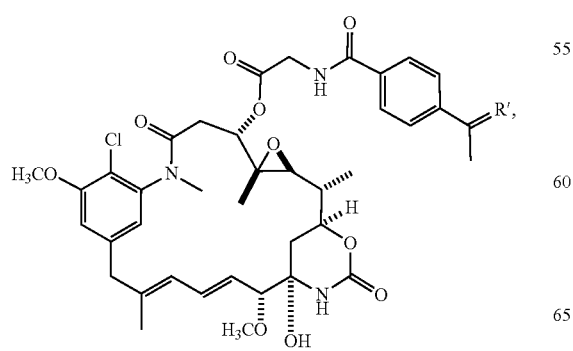

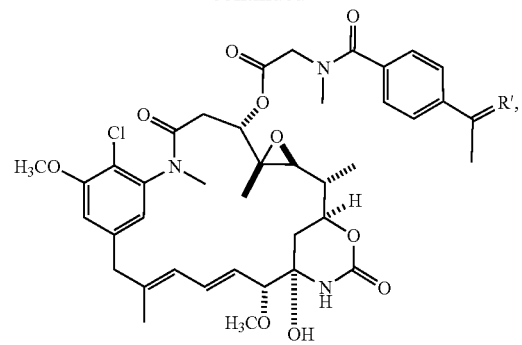

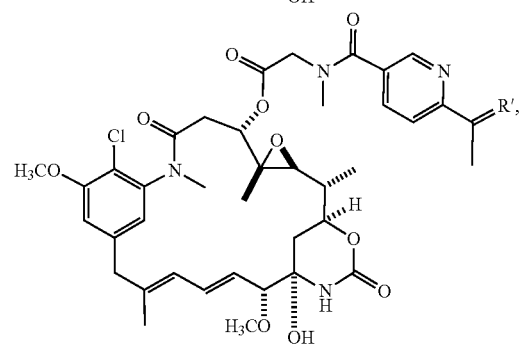

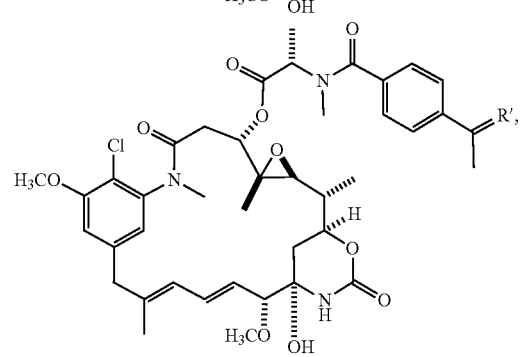

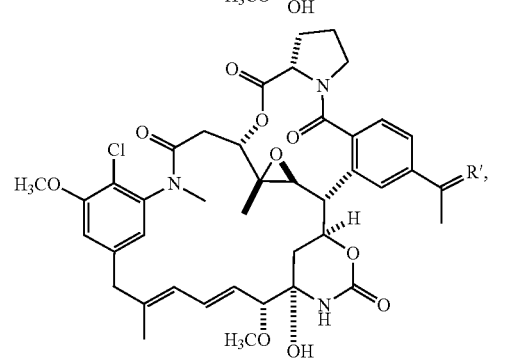

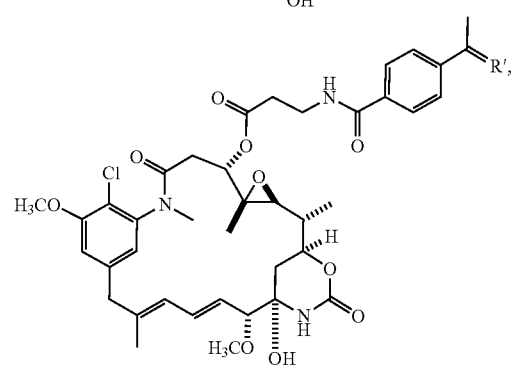

127
-continued
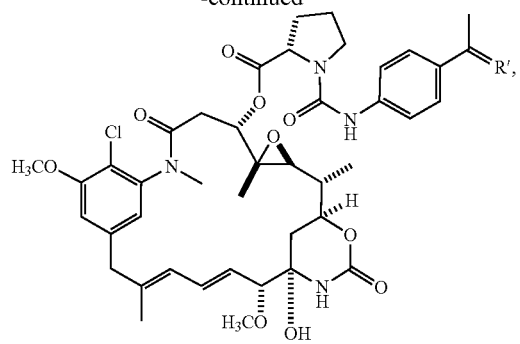
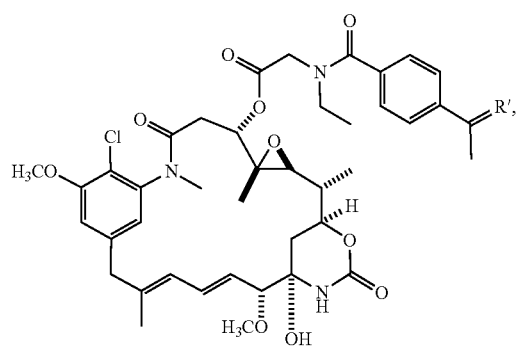
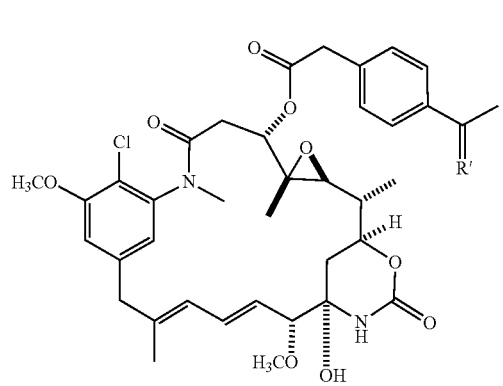
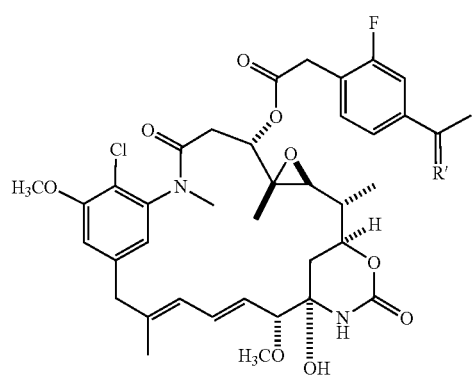
128
-continued
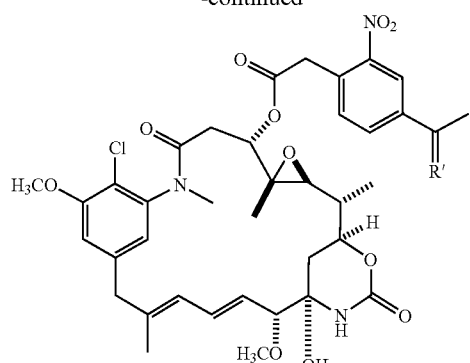
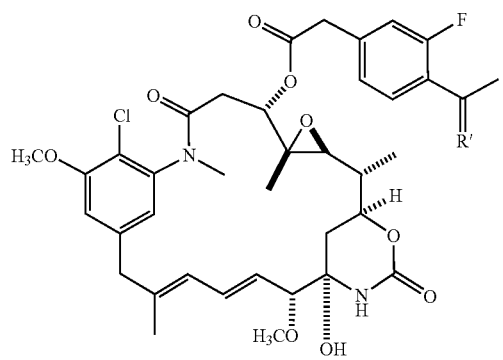
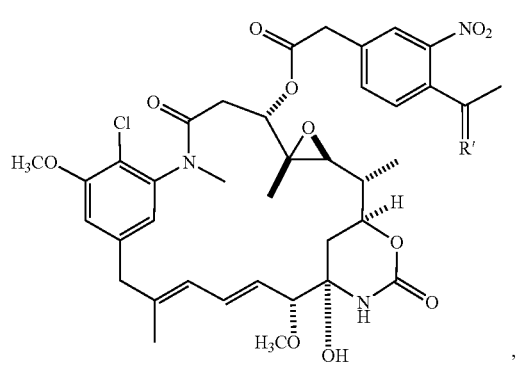
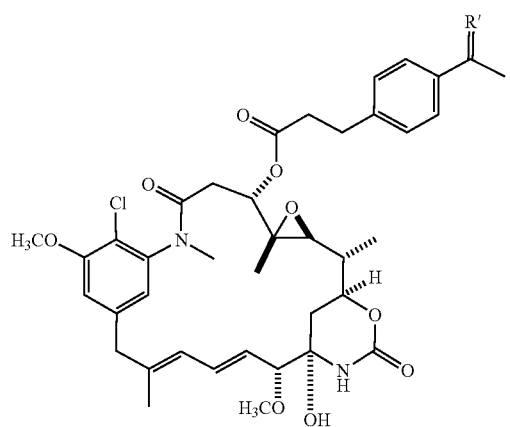

129
-continued
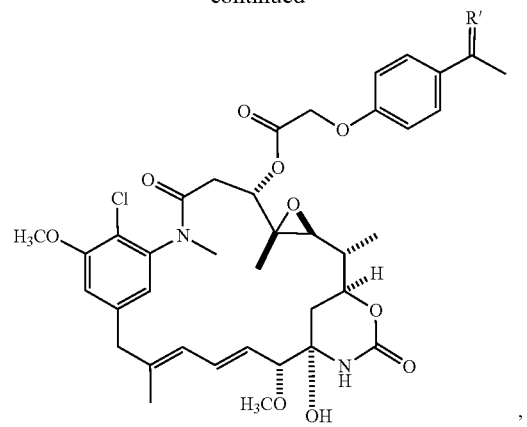
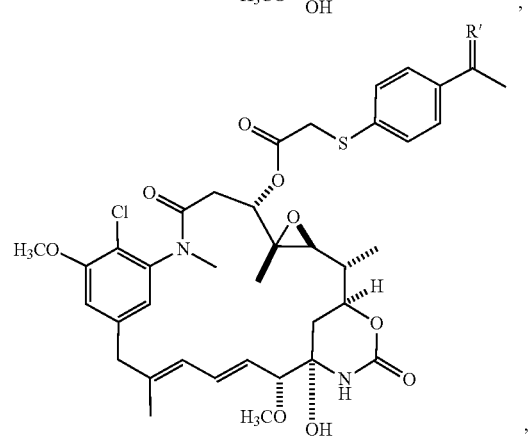
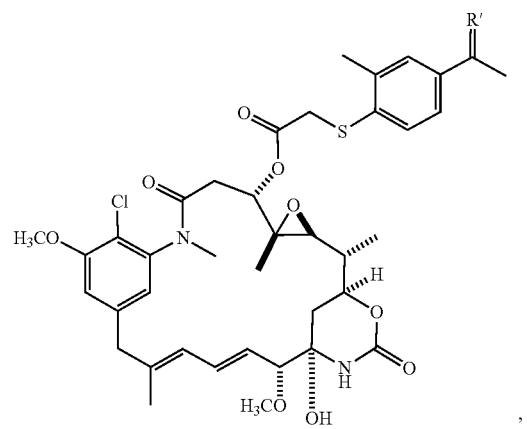
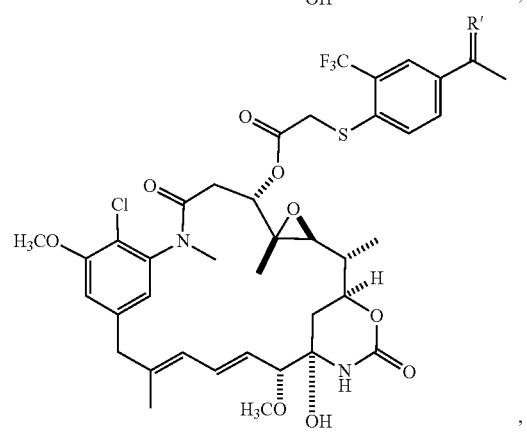
130
-continued
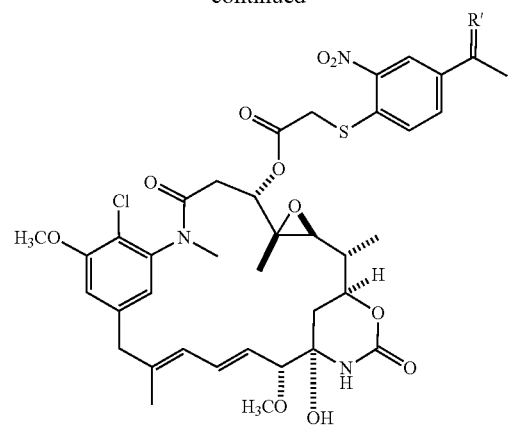
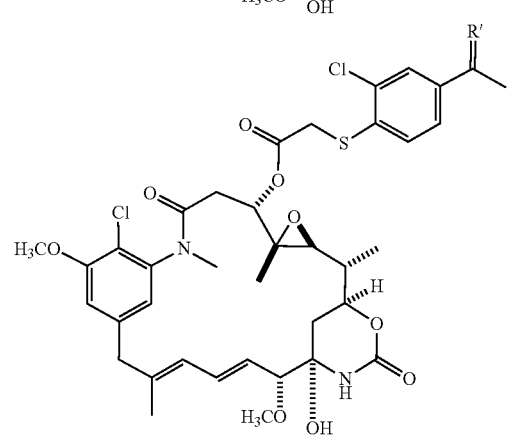
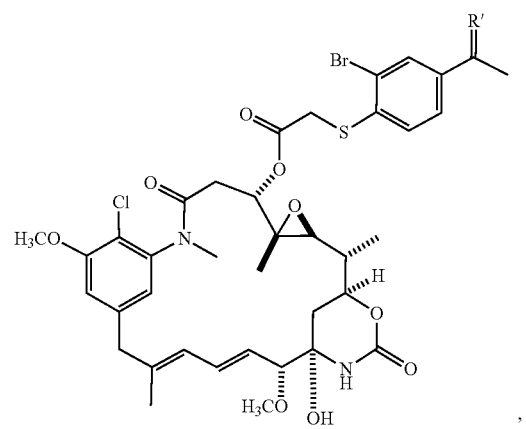
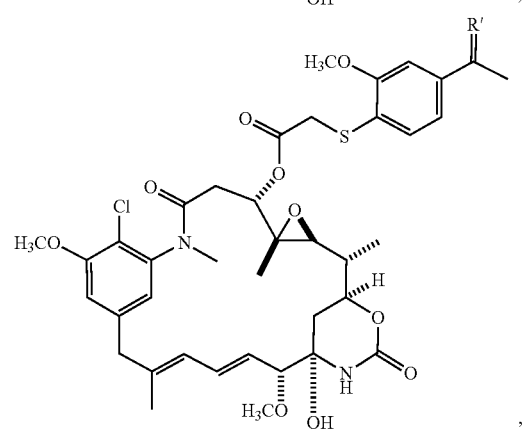

-continued

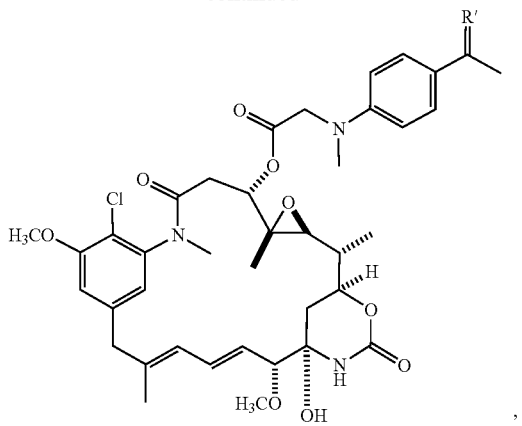

,

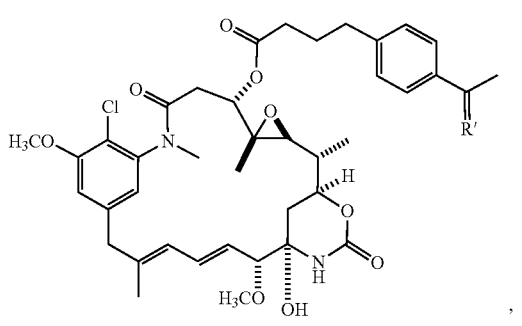

,

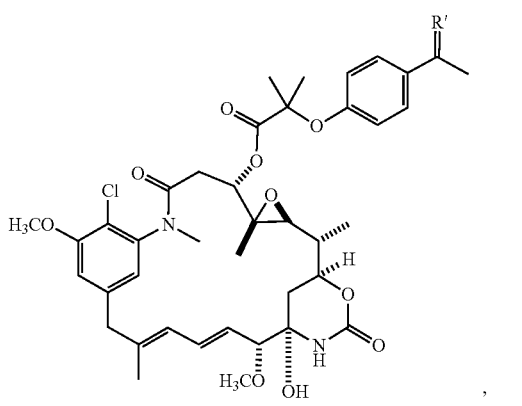

,

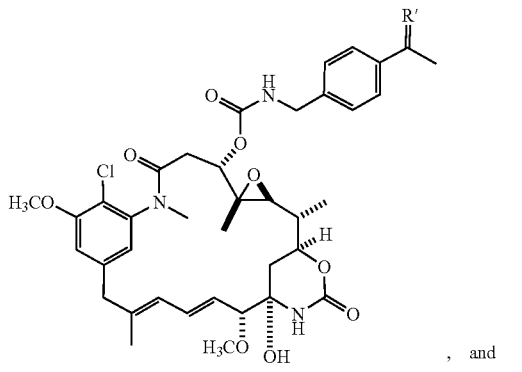

, and

-continued

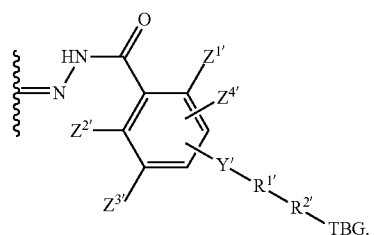

or a pharmaceutically acceptable salt, hydrate, or isomer thereof.

12. The compound of claim 1, wherein the pharmaceutically acceptable counter ion is selected from $H^+$, $Na^+$, $K^+$, $Ca^{2+}$, $Mg^{2+}$, $NR_4^+$, and $NHR_3^+$; wherein R is H or $C_1$-$C_4$ alkyl.

13. The compound of claim 1, wherein R' is O.

14. The compound of claim 1, wherein R' is:

15. The compound of claim 14, wherein the compound is not bound to a thiol-bearing macromolecular carrier or thiol-bearing tumor-specific carrier.

16. The compound of claim 14, wherein the compound is bound to a thiol-bearing macromolecular carrier or thiol-bearing tumor-specific carrier.

17. The compound of claim 16, wherein the thiol-bearing macromolecular carrier or thiol-bearing tumor-specific carrier is selected from endogenous albumin, exogenous albumin, an antibody, an antibody fragment, a peptide, a natural or synthetic polymer, a liposome and a nanoparticle.

18. The compound of claim 14, wherein TBG is an optionally substituted maleimide group.

19. The compound of claim 14, wherein $Z^{1'}$ is selected from —$NO_2$ or —$SO_3M^2$;

and Y' is selected from —NHC(O)— or

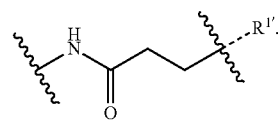

20. The compound of claim 14, wherein $R^{1'}$ is

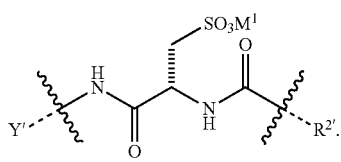

21. The compound of claim 14, wherein R' is:

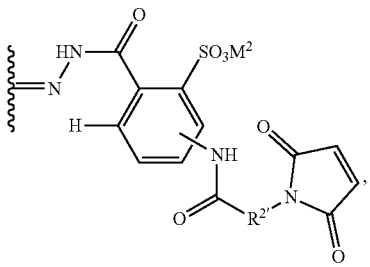

or a pharmaceutically acceptable salt, hydrate, or isomer thereof, wherein
$R^{2'}$ is selected from optionally substituted $C_1$-$C_{18}$ alkyl wherein optionally up to six carbon atoms in said $C_1$-$C_{18}$ alkyl are each independently replaced with —OCH$_2$CH$_2$—.

22. The compound of claim 14, wherein R' is:

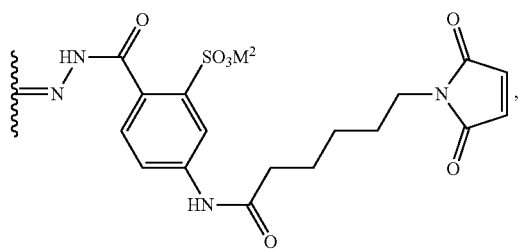

or a pharmaceutically acceptable salt, hydrate, or isomer thereof.

23. The compound of claim 22, wherein the compound is selected from:

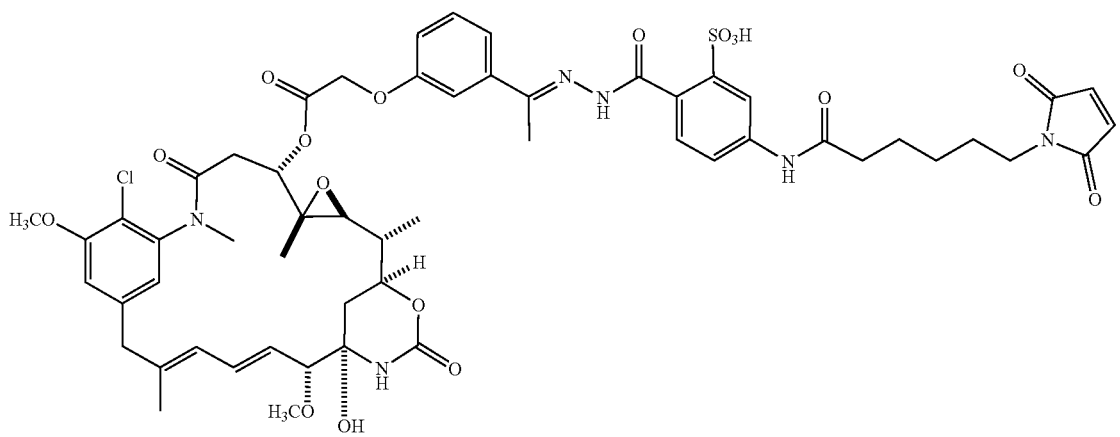

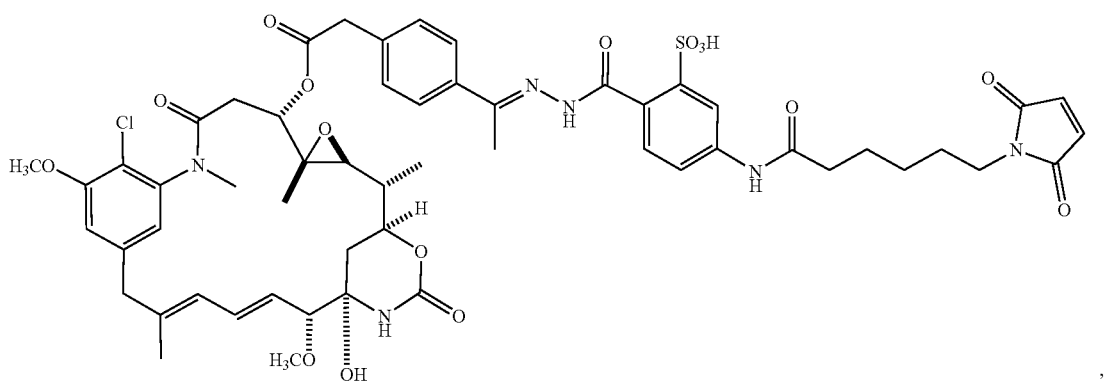

135 136
-continued
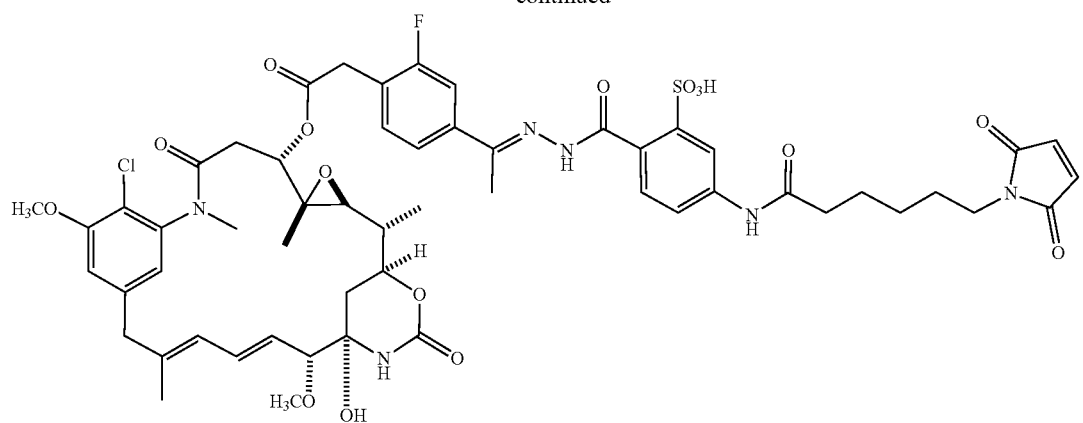
,
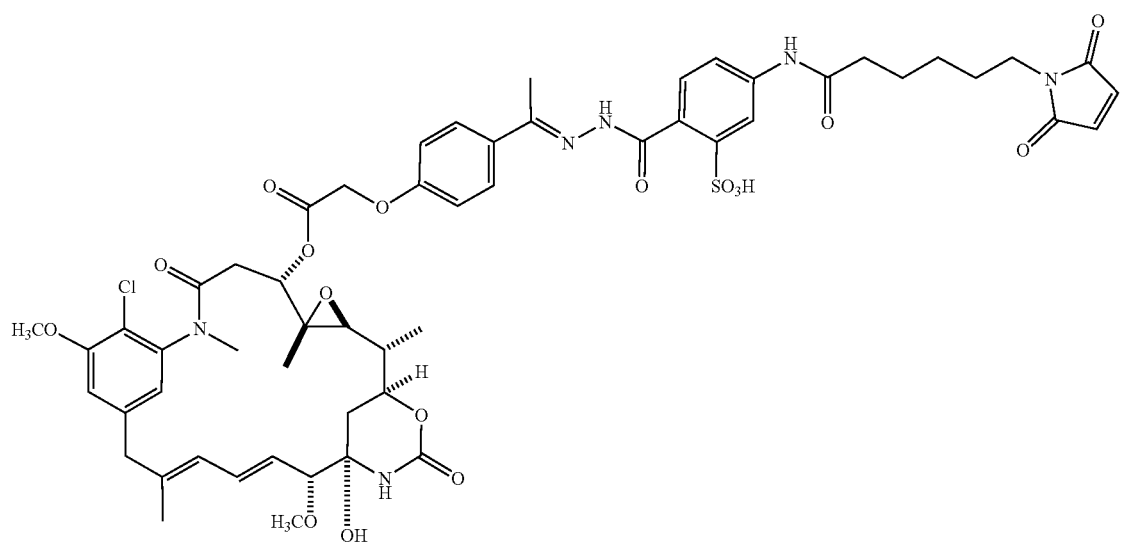
,
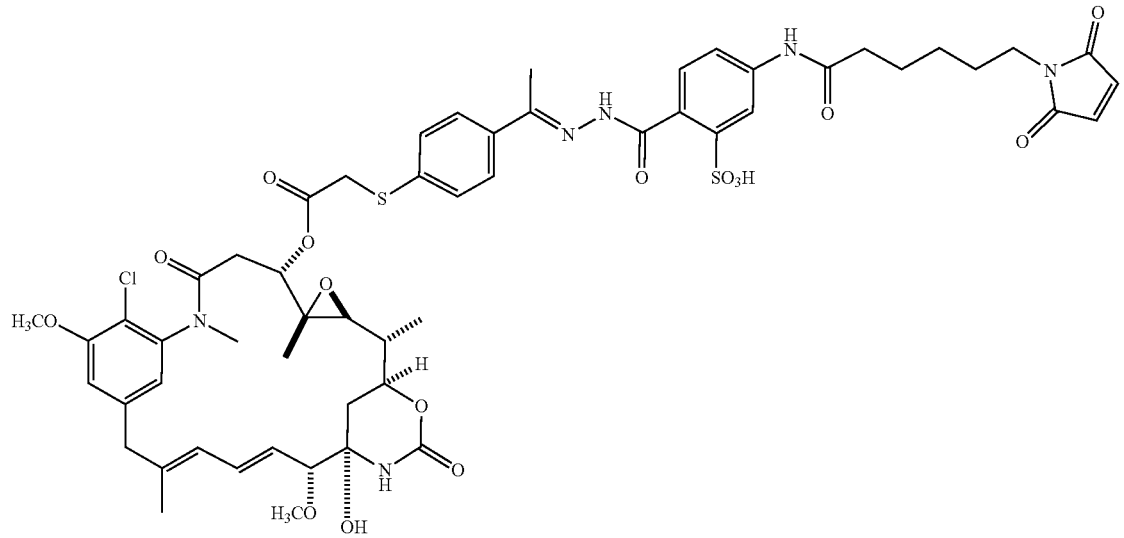
,

-continued
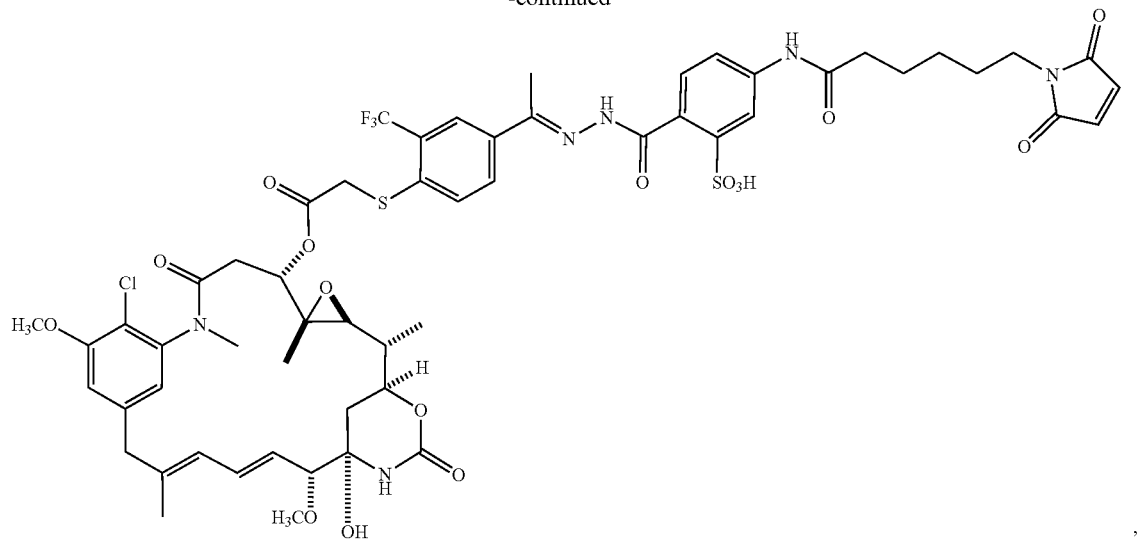
,
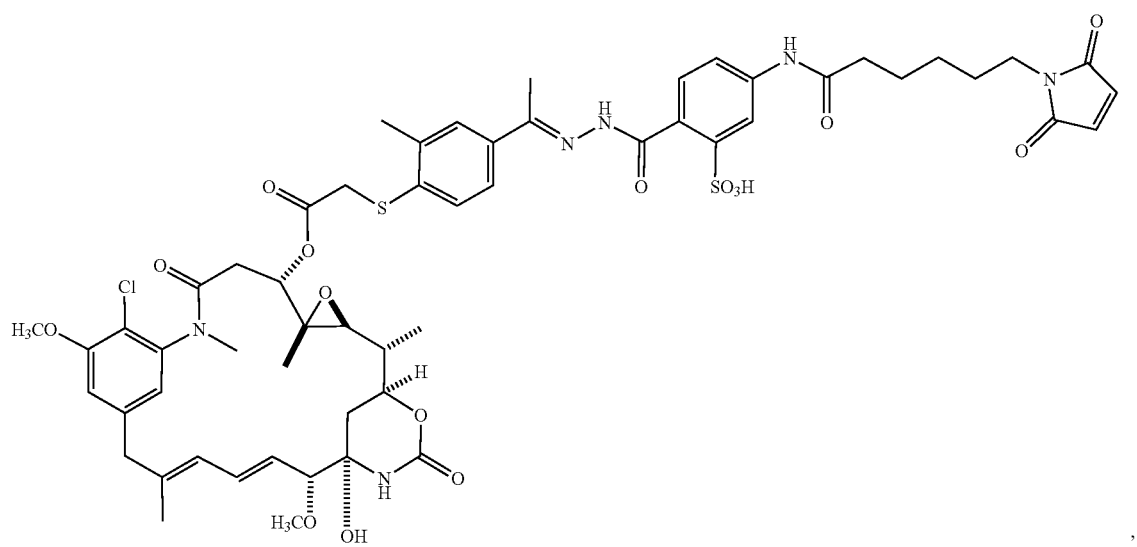 [SMILES: COc1cc2cc(c1Cl)N(C)C(=O)C[C@H](OC(=O)CCc1ccc(/C(C)=N/NC(=O)c3ccc(NC(=O)CCCCCN4C(=O)C=CC4=O)cc3S(=O)(=O)O)cc1)[C@]1(C)O[C@H]1[C@H](C)[C@@H]1C[C@@](O)(NC(=O)O1)[C@H](OC)/C=C/C=C(\C)C2]
,
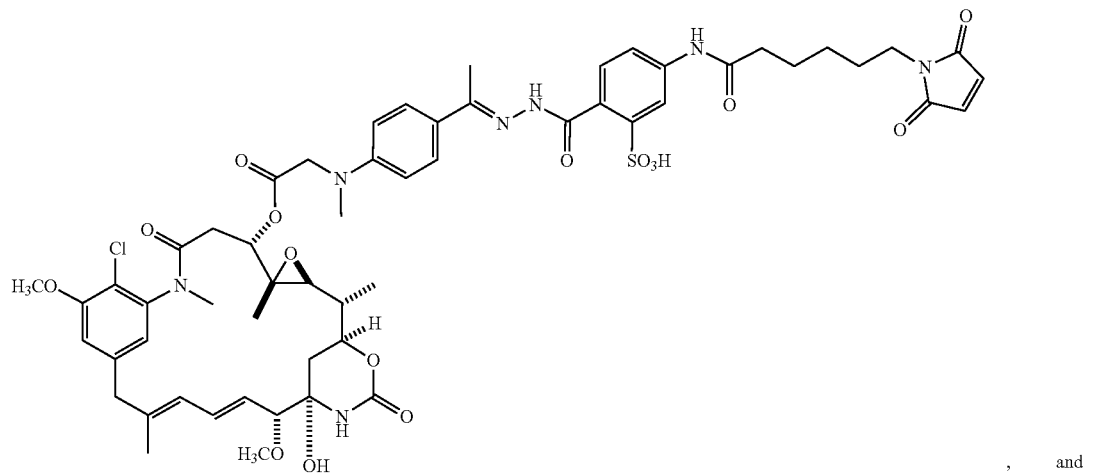
, and

-continued
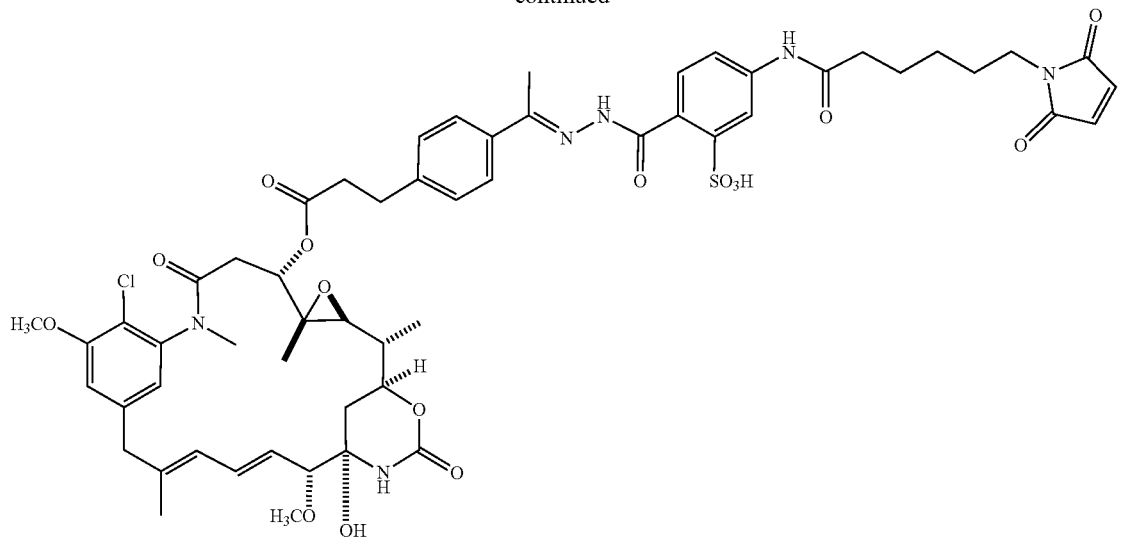
or a pharmaceutically acceptable salt, hydrate, or isomer thereof.
24. The compound of claim 14, wherein R' is:
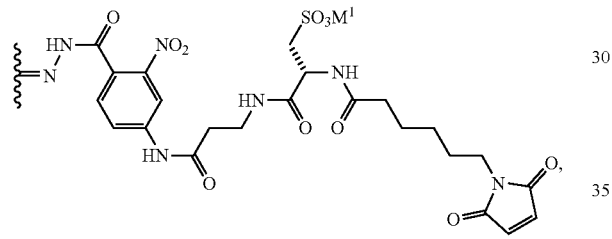
or a pharmaceutically acceptable salt, hydrate, or isomer thereof;
wherein $M^1$ is a pharmaceutically acceptable counter ion.
25. The compound of claim 24, wherein the compound is selected from:
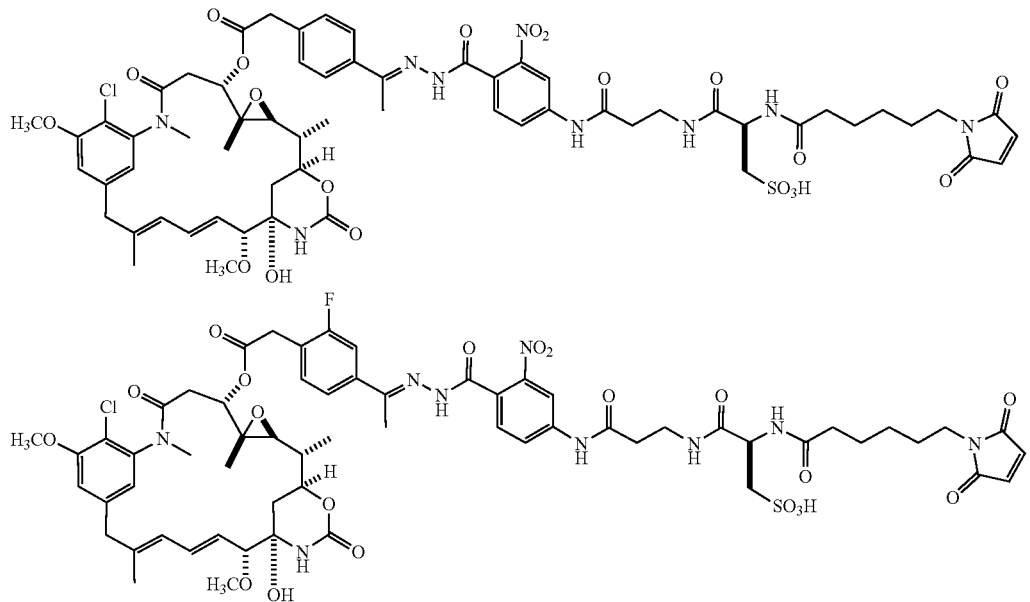

-continued

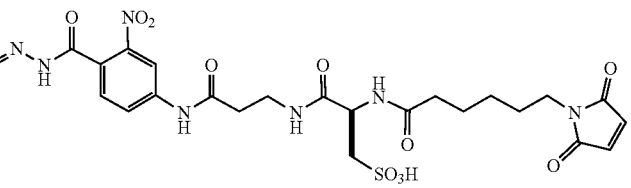
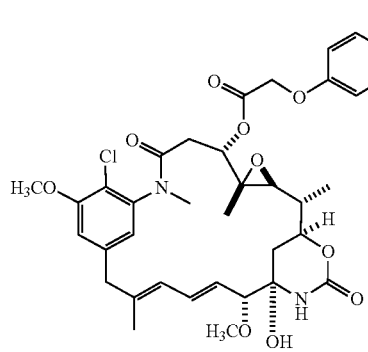

or a pharmaceutically acceptable salt, hydrate, or isomer thereof.

26. The compound of claim 14, wherein R' is:

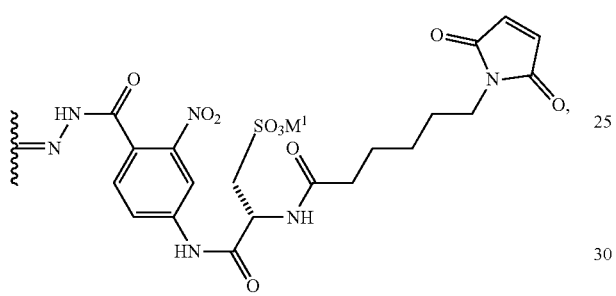

or a pharmaceutically acceptable salt, hydrate, or isomer thereof;

wherein $M^1$ is a pharmaceutically acceptable counter ion.

27. The compound of claim 26, wherein the compound is:

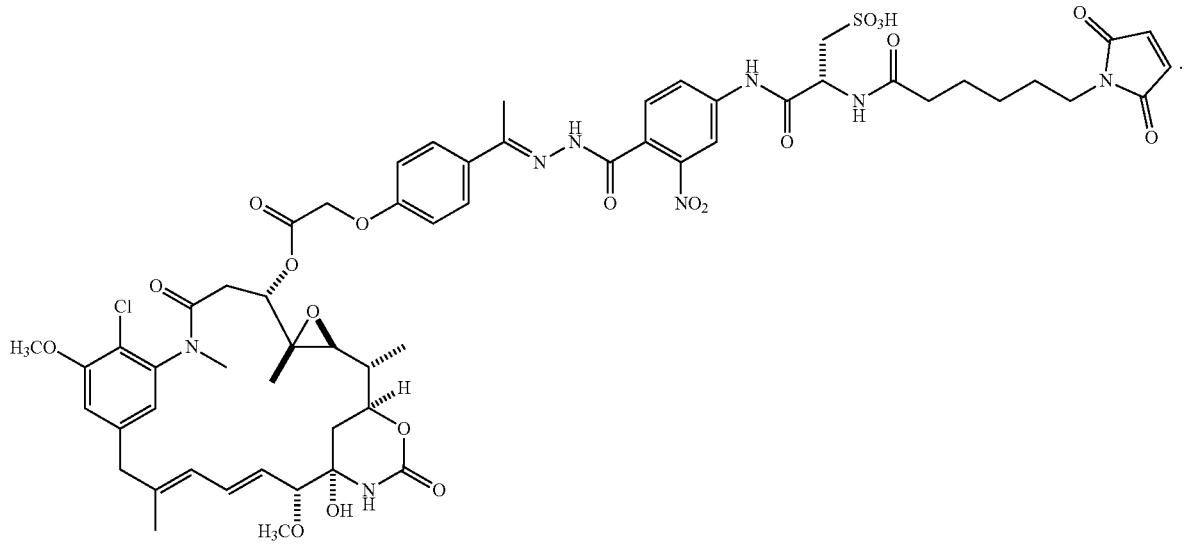 [SMILES: COc1cc2cc(c1Cl)N(C)C(=O)C[C@H](OC(=O)COc1ccc(/C(C)=N/NC(=O)c3ccc(NC(=O)[C@H](CS(=O)(=O)O)NC(=O)CCCCCN4C(=O)C=CC4=O)cc3[N+](=O)[O-])cc1)[C@]1(C)O[C@H]1[C@H](C)[C@@H]1C[C@@](O)(NC(=O)O1)[C@H](OC)/C=C/C=C(\C)C2]

28. A pharmaceutical composition comprising the compound of claim 1, and a pharmaceutically acceptable carrier.

29. A method for treating cancer, comprising administering to a patient in need thereof a therapeutically effective amount of the compound according to claim 1 or the pharmaceutical composition according to claim 28, wherein the cancer is selected from the group consisting of pancreatic cancer, breast cancer, colon cancer, ovarian cancer, head/neck tumors, liver cancer, and non-small cell lung cancer.

* * * * *